United States Patent
Page et al.

(10) Patent No.: US 8,404,690 B2
(45) Date of Patent: *Mar. 26, 2013

(54) PIPERAZINE-2-CARBOXAMIDE DERIVATIVES

(75) Inventors: Patrick Page, Saint-Julien-en-Genevois (FR); Catherine Jorand-Lebrun, Contamine-Sarzin (FR); Russell J. Thomas, Siena (IT); Matthias Schwarz, Geneva (CH)

(73) Assignee: Merck Serono SA, Coinsins (CH)

( * ) Notice: Subject to any disclaimer, the term of this patent is extended or adjusted under 35 U.S.C. 154(b) by 1280 days.

This patent is subject to a terminal disclaimer.

(21) Appl. No.: 10/545,296

(22) PCT Filed: Feb. 6, 2004

(86) PCT No.: PCT/EP2004/050093
§ 371 (c)(1), (2), (4) Date: Jan. 17, 2007

(87) PCT Pub. No.: WO2004/071390
PCT Pub. Date: Aug. 26, 2004

(65) Prior Publication Data
US 2007/0142391 A1   Jun. 21, 2007

(30) Foreign Application Priority Data

Feb. 14, 2003 (EP) .................................... 03003422

(51) Int. Cl.
*A61K 31/497* (2006.01)
*C07D 401/00* (2006.01)
(52) U.S. Cl. ............... 514/253.06; 514/252.13; 544/363
(58) Field of Classification Search .................. None
See application file for complete search history.

(56) References Cited

U.S. PATENT DOCUMENTS

| 5,612,484 A | 3/1997 | Askin et al. |
| 6,153,757 A * | 11/2000 | Zook et al. .................... 546/301 |
| 6,271,201 B1 | 8/2001 | Siler-Khodr |

FOREIGN PATENT DOCUMENTS

| JP | 64-50818 | | 2/1989 |
| WO | 95/21162 | | 8/1995 |
| WO | WO 00/39119 | * | 7/2000 |
| WO | 00/77519 | | 12/2000 |
| WO | WO 02/26720 | * | 4/2002 |
| WO | 02/058546 | | 8/2002 |
| WO | 2004/031182 | | 4/2004 |
| WO | WO 2004/031182 | * | 4/2004 |

OTHER PUBLICATIONS

Bigge et al. "New Preparations of the N-Methyl-D-Aspartate Receptor Antagonist, 4-(3-Phosphonopropyl)-2-Piperazinecarboxylic Acid (CPP)", Tetrahedron Letters, vol. 30, No. 39, pp. 5193-5196 1989.
Breitenbucher et al. "Generation of a Piperazine-2-carboxamide Library: A Practical Application of the Phenol-Sulfide React and Release Linker", Tetrahedron Letters, vol. 39, pp. 1295-1298 1998.
Cheng et al. "Design and Synthesis of Piperazine-Based Matrix Metalloproteinase Inhibitors", J. Med Chem., vol. 43, pp. 369-380 2000.
Chinery et al. "Antioxidants Reduce Cyclooxygenase-2 Expression, Prostaglandin Production, and Proliferation in Colorectal Cancer Cells", Cancer Research, vol. 58, pp. 2323-2327 1998.
Collins. "The impact of population pressure on conservation and development", Research in Reproduction, vol. 16, pp. 1-2 1984.
Mattos et al. "Effects of dietary fatty acids on reproduction in ruminants", Reviews of Reproduction, vol. 5, pp. 38-45 2000.
Qiao et al. "Selected eicosanoids increase the proliferation rate of human colon carcinoma cell lines and mouse colonocytes in vivo", Biochimica et Biophysica Acta, vol. 1258, pp. 215-223 1995.
Russell et al. "Sex, parturition and motherhood without oxytocin?", Journal of Endocrinology, vol. 157, pp. 343-359 1998.
Sugimoto et al. "Failure of Parturition in Mice Lacking the Prostaglandin F Receptor", Science, vol. 277, pp. 681-683 1997.
Takanami-Ohnishi et al. "Possible Involvement of p38 Mitogen-Activated Protein Kinase in Decidual Function in Parturition", Biochemical and Biophysical Research Communications, vol. 288, pp. 1155-1161 2001.
Williams et al. "Effect of sodium cloprostenol and flunixin meglumine on luteolysis and the timing of birth in bitches", Journal of Reproduction and Fertility, vol. 116, pp. 103-111 1999.
Amar Chatterjee, "The Possible Mode of Action of Prostaglandins, XII, Differentiall Effects of Prostaglandin F2a in inducing Premature Evacuation of Conceptus in the Intact and Castrated Pregnant Rat", Prostaglandins, vol. 12, No. 6, pp. 1053-1059 (Dec. 1976).

* cited by examiner

*Primary Examiner* — Bong-Sook Baek
(74) *Attorney, Agent, or Firm* — Oblon, Spivak, McClelland, Maier & Neustadt, L.L.P.

(57) ABSTRACT

The present invention is related to piperazine-2-carboxamide derivatives of formula (I) for the treatment and/or prophylaxis of preterm labor, premature birth, dysmenorrhea and for stopping labor prior to cesarean delivery. Wherein A, X, Y, $R^1$ and $R^2$ are as defined in the description.

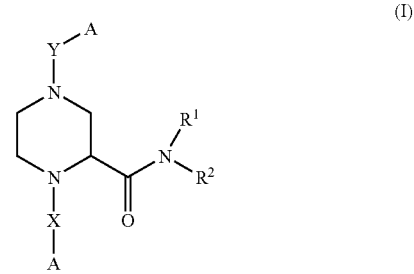

(I)

10 Claims, No Drawings

PIPERAZINE-2-CARBOXAMIDE DERIVATIVES

CROSS-REFERENCE TO RELATED APPLICATIONS

This application is a 371 of PCT/EP04/50093 filed Feb. 6, 2004 and claims the benefit of EP 03003422.7 filed Feb. 14, 2003.

FIELD OF THE INVENTION

The present invention is related to piperazine-2-carboxamide derivatives of formula (I) for the treatment and/or prophylaxis of preterm labor, premature birth, dysmenorrhea and for stopping labor prior to cesarean delivery. Also, the present invention is related to novel piperazine-2-carboxamide derivatives of formulae (II) and (III).

BACKGROUND OF THE INVENTION

In the field of obstetrics, one of the most important problems is the management of preterm labor and premature birth as they represent a major cause of perinatal morbidity and mortality.

In recent years, strong evidence has accumulated indicating that the hormone oxytocin plays a major role in initiating labor in mammals, notably in humans. Thereby, it is assumed that oxytocin exerts said effect in a direct as well as an indirect way, by contracting the uterine myometrium and by enhancing the synthesis and release of contractile prostaglandins from the uterine endometrium/decidua. These prostaglandins may furthermore play a role in the cervical ripening process.

In parturition, the high circulating concentrations of progesterone induce uterine quiescence while the uterus acquires contractile ability. Shortly before term, plasma progesterone concentrations fall, oxytocin receptor expression in the uterus increases markedly, and uterine contractile activity increases. At term, the contractions rise to a crescendo, resulting in delivery as a result of two interacting positive feedback loop. The first is a local uterine loop: within the uterus itself prostaglandins and other uterotonic factors are produced and released in response to uterine contractions. The second loop involves the hypothalamus: in response to uterine contractions and vaginal and cervical distension, magnocellular oxytocin neurons in the hypothalamus increase their activity resulting in the release of oxytocin from their axon terminals in the posterior pituitary; the released oxytocin acts upon the uterus both to stimulate the further production of prostaglandins and to contribute further to the contractions of the uterus. (*Journal of Endocrinology* 157, p. 343-359 (1998) by J. A Russell and al.).

For the treatment of preterm labor, several approaches have been considered such as the use of magnesium sulfate, ethanol or therapeutic agents acting as $\alpha_2$ adrenergic agonists or oxytocin antagonists:

With the use of magnesium sulfate, it has been observed that plasma concentrations above the therapeutic range of 4 to 8 mg/dL can cause inhibition of cardiac conduction and neuromuscular transmission, respiratory depression and cardiac arrest, thus making this agent unsuitable notably when the renal function is impaired.

Ethanol is effective in preventing premature labor, but it does not produce a corresponding reduction in the incidence of fetal respiratory distress. Also, ethanol is assumed to have a negative impact on the fetus.

The $\beta_2$-adrenergic receptor generally causes an inhibitory action within the cells wherein it is expressed (muscles, heart, uterus etc). $\beta_2$-adrenergic agonists are used to activate said inhibitory action of the receptor. Hence, $\beta_2$-adrenergic agonists are sympathomimetics which—among others—inhibit uterine contractility. Known $\beta_2$-adrenergic agonists for the treatment of preterm labor are Ritodrine, Terbutaline and Albuterol.

Oxytocin antagonists: Oxytocin (OT) is a peptide hormone causing the contraction of the uterus of mammals during labor. Oxytocin (OT) receptors increase dramatically during the course of pregnancy. The concentration of OT receptors has been shown to correlate with spontaneous uterine activity. In the last few years, a number of papers have suggested that the hormone oxytocin may be a physiological initiator of labor in several mammalian species including humans. Furthermore, oxytocin is believed to exert this effect in two different parts, either by directly contracting the uterine myometrium and by enhancing the synthesis and release of contractile prostaglandins from the uterine endometrium/decidua. Therefore, by blocking oxytocin, the direct (contractile) and indirect (enhanced prostaglandin synthesis) effects of oxytocin on the uterus may be achieved.

Prostaglandins (PGs), more particularly prostaglandin $F_{2\alpha}$ ($PGF_{2\alpha}$), play a key role in the normal physiology of several tissues including ovary, oviduct, uterus, testis, lung and possibly eye and heart and is implicated in reproductive functions such as ovulation, luteolysis and parturition. It is well known that parturition is initiated when prostaglandin $F_{2\alpha}$ interacts with FP (Prostaglandin F receptor) in ovarian luteal cells of the pregnant mice to induce luteolysis. (*Science* vol. 277, p. 681-687 (1997) by Yuhihiko Sugimoto et al). Actions of $PGF_{2\alpha}$ are mediated by the PGF receptor (FP), which is a heterotrimeric guanosine triphosphate—binding protein (G protein)—coupled rhodopsin type receptor specific to this PG (*Science* vol. 277, p. 681-83 (1998) by Yuhihiko Sugimoto et al.).

These prostaglandins belong to a group of eicosanoids that are produced by the enzymatic activity of cyclooxygenase. Together with the thromboxanes, prostaglandins constitute the prostanoid subgroup of the eicosanoids. Prostaglandins (PGs) mediate various physiological processes such as fever generation and inflammation. Aspirin and related drugs act through inhibition of PG biosynthesis.

$PGF_{2\alpha}$ is synthesized, to varying degrees, by almost every tissue in the body and is a stimulant of several different types of physiological functions including granulose lutein cell death, myometrial smooth muscle contraction, Leydig cell testosterone synthesis regulation, regulation of oviductal cilia beating, bronchoconstriction, and bone metabolism. They are synthesized in fetal and maternal membranes and act to ripen the cervix and contract the myometrium. $PGF_{2\alpha}$ is a major prostaglandin for enhancing uterine contractility.

Specific prostaglandin receptors ($EP_1$, $EP_2$, $EP_4$ and FP) are expressed in the human myometrium Activation of $EP_2$ and $EP_4$ receptors results in smooth muscle relaxation whereas activation of the $PGF_{2\alpha}$-selective receptor (FP receptor) results in contraction. Indeed, the prostaglandin $F_{2\alpha}$ receptor acts via a G protein-coupled receptor, coupled to activation of phospholipase C and increases in $IP_3$ that release $Ca^{2+}$ from intracellular stores. The increases in intracellular calcium that ensue lead to increased contraction of smooth muscle via activation of myosin light chain kinase. Also, it is known that mice lacking the FP receptor have normal fertility but no labor at term. However healthy pups were delivered by cesarean cut. One of the most important roles of $PGF_{2\alpha}$ is in reproductive biology as a luteolytic agent. In the non-pregnant state, at the end of the luteal phase, increased pulsatile serum levels of PGF$_{2\alpha}$ (of uterine origin) cause apoptotic cell death of the granulosam lutein cells (*Res. Reprod.* 16:1-2 (1984) by McCracken).

There is recent evidence for up-regulation of the contractile FP receptor with the onset and during progression of labor. Also, recent reports indicate that oxytocin induces production of PGs in human myometrial cells via upregulation of COX-2. Such a mechanism may explain the sustained release of PGs in uterine tissue, promoting labor. Therefore, there is strong evidence that interfering with the prostaglandin pathway by blocking selectively the contractile FP receptor will delay the progression of labor. A compound able to block the interaction between PGF$_{2\alpha}$ and its receptor, i.e. a PGF$_{2\alpha}$-receptor antagonist, is therefore assumed to be more efficacious for treating preterm labor than current regimens.

Because of the involvement of PGF$_{2\alpha}$ in birth initiation, several approaches have already been performed to test new PGF$_{2\alpha}$ inhibitors. Indomethacin is a well known prostaglandin inhibitor and has already been tested to study the possible mode of action of prostaglandins (*Prostaglandins*, 12(6) p. 1053-9 (1976) by Chatterjee A.). In *J. Reprod. Fertil.*, 116(1), p. 103-111 (1999) Williams B. J. et al observed that flunixin meglumin disrupted the normal 13,14-dihydro-15-keto prostaglandin F$_{2\alpha}$ profile but did not abolish prostaglandin synthesis completely or delay the onset of labor in treated animals. Mattos R. et al (*Rev. Reprod.*, 5(1), p. 3845 (2000) use polyunsaturated fatty acids such as linoleic, linolenic, eicosapentaenoic and docosahexaenoic acids which may inhibit prostaglandin F$_{2\alpha}$.

Recently, a phenol derivative known as p38 inhibitor (4-[5-(4-fluorophenyl)-4-(4-pyridyl)-imidazol-2-yl]phenol) has been tested and it has been observed that said compound inhibited both prostaglandin F$_{2\alpha}$ production and COX-2 expression induced by stimulation with IL-1β (*Biochem. Biophys. Res. Common.*, 288(5), p. 1155-1161 (2001) by Chuo-ku Chiba).

Tsumura & Co proposed prostaglandin F$_{2\alpha}$ inhibitor active to relax the smooth muscle of uterine and effective for the remedy of abdominal pain caused by abortion, premature labor and dysfunction, by using a phtalide derivative as an active component (JP-01050818).

In their patent (U.S. Pat. No. 6,271,201), Board of Regents, the University of Texas System discloses a method for regulating placental cell production of thromboxane and PGF$_{2\alpha}$ comprising treating placenta cells with a pharmacologically effective amount of insulin-like growth factor I sufficient to inhibit thromboxane and prostaglandin F$_{2\alpha}$ production without affecting prostacyclin or prostaglandin E$_2$ production.

Furthermore, literature suggests that prostaglandins stimulate the proliferation of human colon carcinoma cells in vitro (*Biochemica at Biophysica Acta* 1258/2, p. 215-223 (1995)). It is known that increased expression of cyclooxygenase (COX) and over-production of prostaglandins (PGs) have been implicated in the development and progression of colorectal cancer (*Cancer Research*, Vol 58, Issue 11 p. 2323-2327). It has been disclosed in the patent literature that a decrease in a specific prostanoid metabolite, PGF2α, could account for the beneficial effects of NSAIDS in the prevention and treatment of colorectal cancer (WO 02/058546 filed by The Arizona Board of Regents).

SUMMARY OF THE INVENTION

The present invention relates to the use of piperazine-2-carboxamide derivatives of formula (I)

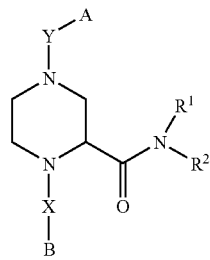

(I)

as well as pharmaceutically acceptable salts thereof for the preparation of medicament for the treatment and/or prevention of preterm labor, premature birth, dysmenorrhea, and for stopping labor prior to cesarean delivery. In one embodiment, the compounds of this invention are antagonists of prostaglandin receptors, particularly of the prostaglandin F$_{2\alpha}$ receptor (FP).

Further, the present invention relates to novel piperazine-2-carboxamide derivatives of formulae (II) and (III)

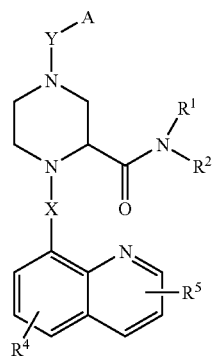

(II)

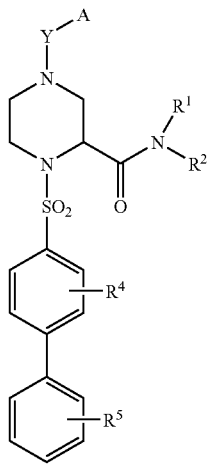

(III)

DETAILED DESCRIPTION OF THE INVENTION

It has been found that compounds of the present invention are modulators of the Prostaglandin receptor. According to one embodiment they are antagonists of the Prostaglandin F$_{2\alpha}$ receptor (FP) function. When the Prostaglandin F$_{2\alpha}$ receptor (FP) is bound by the compounds of the present invention, PGF$_{2\alpha}$ is antagonized by being blocked from its receptor and thus being unable to exert its biological or pharmacological effects. The compounds of the present invention are therefore useful in the treatment and prevention of preterm labor, premature birth and for stopping labor prior to cesarean delivery.

The compounds of the present invention are useful in the treatment of dysmenorrhea which may be defined as a cyclic pain associated with menses during ovulatory cycles. The pain is thought to result from uterine contractions and ischemia, probably mediated by the effect of prostaglandins produced in the secretory endometrium. By blocking both the effects of prostaglandin F$_{2\alpha}$ on the uterus, a FP antagonist is more efficacious for treating dysmenorrhea than current regimens.

In particular, compounds of the present invention are useful in the treatment and prevention of prostaglandin related disorders of mammals and especially humans. It is a purpose of this invention to provide a method to down-regulate, or to antagonize the function of prostaglandins, particularly prostaglandin F$_{2\alpha}$, in disease states in mammals. It is another purpose of this invention to develop a method of preventing or treating prostaglandin F$_{2\alpha}$ related disorders by antagonizing the binding of said prostaglandin to its receptor.

The following paragraphs provide definitions of the various chemical moieties that make up the compounds according to the invention and are intended to apply uniformly through-out the specification and claims unless an otherwise expressly set out definition provides a broader definition.

"C$_1$-C$_6$-alkyl" refers to monovalent alkyl groups having 1 to 6 carbon atoms. This term is exemplified by groups such as methyl, ethyl n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenantrenyl and the like.

"C$_1$-C$_6$-alkyl aryl" refers to C$_1$-C$_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, phthalazinyl quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"C$_1$-C$_6$-alkyl heteroaryl" refers to C$_1$-C$_6$alkyl groups having a heteroaryl substituent, including 2-furylmethyl, 2-thienylmethyl, 2-(1H-indol-3-yl)ethyl and the like.

"C$_2$-C$_6$-alkenyl" refers to alkenyl groups preferably having from 2 to 6 carbon atoms and having at least 1 or 2 sites of alkenyl unsaturation. Preferable alkenyl groups include ethenyl (—CH═CH$_2$), n-2-propenyl (allyl, —CH$_2$CH═CH$_2$) and the like.

"C$_2$-C$_6$-alkenyl aryl" refers to C$_2$-C$_6$-alkenyl groups having an aryl substituent, including 2-phenylvinyl and the like.

"C$_2$-C$_6$-alkenyl heteroaryl" refers to C$_2$-C$_6$-alkenyl groups having a heteroaryl substituent, including 2-(3-pyridinyl)vinyl and the like.

"C$_2$-C$_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—CH$_2$C≡CH), and the like.

"C$_2$-C$_6$-alkynyl aryl" refers to C$_2$-C$_6$-alkynyl groups having an aryl substituent, including phenylethynyl and the like.

"C$_2$-C$_6$-alkynyl heteroaryl" refers to C$_2$-C$_6$-alkynyl groups having a heteroaryl substituent, including 2-thienylethynyl and the like.

"C$_3$-C$_8$-cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

"C$_1$-C$_6$-alkyl cycloalkyl" refers to C$_1$-C$_6$-alkyl groups having a cycloalkyl substituent, including cyclohexylmethyl, cyclopentylpropyl, and the like.

"heterocycloalkyl" refers to a C$_3$-C$_8$-cycloalkyl group according to the definition above, in which 1 to 3 carbon atoms are replaced by heteroatoms chosen from the group consisting of O, S, NR, R being defined as hydrogen or C$_1$-C$_6$ alkyl. Preferred heterocycloalkyl include pyrrolidine, piperidine, piperazine, 1-methylpiperazine, morpholine, and the like.

"C$_1$-C$_6$-alkyl heterocycloalkyl" refers to C$_1$-C$_6$-alkyl groups having a heterocycloalkyl substituent, including 2-(1-pyrrolidinyl)ethyl, 4-morpholinylmethyl, (1-methyl-4-piperidinyl)methyl and the like.

"Carboxy" refers to the group —C(O)OH.

"C$_1$-C$_6$-alkyl carboxy" refers to C$_1$-C$_6$-alkyl groups having a carboxy substituent, including 2-carboxyethyl and the like.

"Acyl" refers to the group —C(O)R where R includes H, "C$_1$-C$_6$-allyl", "C$_2$-C$_6$-alkenyl", "C$_2$-C$_6$-alkynyl", "C$_3$-C$_8$-cycloalkyl", heterocycloalkyl "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-allyl acyl" refers to C$_1$-C$_6$-alkyl groups having an acyl substituent, including 2-acetylethyl and the like.

"Aryl acyl" refers to aryl groups having an acyl substituent, including 2-acetylphenyl and the like.

"Heteroaryl acyl" refers to heteroaryl groups having an acyl substituent, including 2-acetylpyridyl and the like.

"C$_3$-C$_8$-(hetero)cycloalkyl acyl" refers to 3 to 8 membered cycloalkyl or heterocycloalkyl groups having an acyl substituent.

"Acyloxy" refers to the group —OC(O)R where R includes H, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl acyloxy" refers to C$_1$-C$_6$-alkyl groups having an acyloxy substituent, including 2-(acetyloxy)ethyl and the like.

"Alkoxy" refers to the group —O—R where R includes "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl alkoxy" refers to $C_1$-$C_6$-alkyl groups having an alkoxy substituent, including 2-ethoxyethyl and the like.

"Alkoxycarbonyl" refers to the group —C(O)OR where R includes "$C_1$-$C_6$-alkyl", "$C_2$-$C_6$-alkenyl", "$C_2$-$C_6$-alkynyl", "$C_3$-$C_6$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl alkoxycarbonyl" refers to $C_1$-$C_6$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen, "$C_1$-$C_6$-alkyl", "$C_1$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl aminocarbonyl" refers to $C_1$-$C_6$-alkyl groups having an aminocarbonyl substituent, including 2-(dimethylaminocarbonyl)ethyl and the like.

"Acylamino" refers to the group —NRC(O)R' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acylamino" refers to $C_1$-$C_6$-alkyl groups having an acylamino substituent, including 2-(propionylamino)ethyl and the like.

"Ureido" refers to the group —NRC(O)NR'R" where each R, R', R'" is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-allyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocloalkyl", and where R' and R", together with the nitrogen atom to which they are attached, can optionally form a 3-8-membered heterocycloalkyl ring.

"$C_1$-$C_6$-alkyl ureido" refers to $C_1$-$C_6$-allyl groups having an ureido substituent, including 2-(N'-methylureido)ethyl and the like.

"Carbamate" refers to the group —NRC(O)OR' where each R, R' is independently hydrogen, "$C_1$-$C_6$-alkyl", "$C_2$-$C_6$-alkynyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Amino" refers to the group —NRR' where each R, R' is independently hydrogen, "$C_1$-$C_6$-alkyl", "$C_2$-$C_6$-alkenyl", "$C_2$-$C_6$-alkynyl", "$C_3$-$C_8$cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R and R', together with the nitrogen atom to which they are attached, can optionally form a 3-8-membered heterocycloalkyl ring.

"$C_1$-$C_6$-alkyl amino" refers to $C_1$-$C_6$-alkyl groups having an amino substituent, including 2-(1-pyrrolidinyl)ethyl and the like.

"Ammonium" refers to a positively charged group —N$^+$RR'R", where each R, R', R" is independently, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R and R', together with the nitrogen atom to which they are attached, can optionally form a 3-8-membered heterocycloalkyl ring.

"$C_1$-$C_6$-alkyl ammonium" refers to $C_1$-$C_6$-alkyl groups having an ammonium substituent, including 2-(1-pyrrolidinyl)ethyl and the like.

"Halogen" refers to fluoro, chloro, bromo and iodo atoms.

"Sulfonyloxy" refers to a group —SO$_2$—R wherein R is selected from H, "$C_1$-$C_1$-alkyl", "$C_1$-$C_6$-alkyl" substituted with halogens, e.g., an —OSO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonyloxy" refers to $C_1$-$C_6$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "$C_1$-$C_6$-alkyl", "$C_1$-$C_6$-alkyl" substituted with halogens, e.g. an —SO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonyl" refers to $C_1$-$C_6$-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl" substituted with halogens, e.g., an —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfinyl" refers to $C_1$-$C_6$-alkyl groups having a sulfinyl substituent, including 2-(methylsulfinyl)ethyl and the like.

"Sulfinyl" refers to groups —S—R where R includes H, "$C_1$-$C_6$-alkyl", "$C_1$-$C_6$-alkyl" substituted with halogens, e.g., an —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl". "$C_1$-$C_6$-alkyl heterocycloalkyl". Preferred sulfinyl groups include methylsulfanyl, ethylsulfanyl, and the like.

"$C_1$-$C_6$-alkyl sulfanyl" refers to $C_1$-$C_6$-alkyl groups having a sulfanyl substituent, including 2-(ethylsulfanyl)ethyl and the like.

"Sulfonylamino" refers to a group —NRSO$_2$R' where each R, R' includes independently hydrogen, "$C_1$-$C_6$-alkyl", "$C_2$-$C_6$-alkenyl", "$C_2$-$C_6$alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonylamino" refers to $C_1$-$C_6$-alkyl groups having a sulfonylamino substituent, including 2-(ethylsulfonylamino)ethyl and the like.

"Aminosulfonyl" refers to a group —SO$_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl aminosulfonyl" refers to $C_1$-$C_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "$C_1$-$C_6$-alkyl aryl", "$C_1$-$C_6$-alkyl heteroaryl", "$C_1$-$C_6$ alkyl cycloalkyl", "$C_1$-$C_6$-alkyl heterocycloalkyl", "amino", "ammonium", "acyl", "acyloxy", "acylamino", "aminocarbonyl", "alkoxycarbonyl", "ureido", "carbamate", "aryl", "heteroaryl", "sulfinyl", "sulfonyl", "alkoxy", "sulfanyl", "halogen", "carboxy", trihalomethyl, cyano, hydroxy, mercapto, nitro, and the like. Alternatively said substitution could also comprise situations where neighbouring substituents have undergone ring closure, notably when vicinal functional substituents are involved, thus forming, e.g., lactams, lactons, cyclic anhydrides, but also acetals, thioacetals, aminals formed by ring closure for instance in an effort to obtain a protective group.

"Pharmaceutically acceptable salts or complexes" refers to salts or complexes of the below-identified compounds of formulae (I), (II) and (III) that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, methanesulfonic acid and poly-galacturonic acid. Said compounds can also be administered as pharmaceutically acceptable quaternary salts known by a person skilled in the art, which specifically include the quarternary ammonium salt of the formula —NR,R',R"$^+$Z$^-$; wherein R, R', R" is independently hydrogen, alkyl, or benzyl, $C_1$-$C_6$-alkyl, $C_2$-$C_6$-alkenyl, $C_2$-$C_6$-alkynyl, $C_1$-$C_6$alkyl aryl, $C_1$-$C_6$-alkyl heteroaryl, cycloalkyl, heterocycloalkyl, and Z is a counterion, including chloride, bromide, iodide, —O— alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein.

"Enantiomeric excess" (ee) refers to the products that are obtained by an asymmetric synthesis, i.e. a synthesis involving non-racemic starting materials and/or reagents or a synthesis comprising at least one enantioselective step or to products that have been purified using chiral techniques, whereby a surplus of one enantiomer in the order of at least about 52% ee is yielded.

A first aspect of the present invention consists in the use of compounds of formula (I)

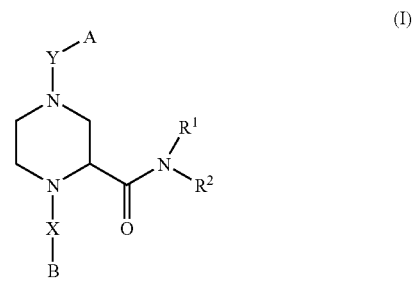

(I)

as well as its tautomers, its geometrical isomers, its optically active forms as enantiomers, diastereomers and its racemate forms, as well as pharmaceutically acceptable salts and pharmaceutically active derivatives thereon for the preparation of a medicament for the treatment and/or prevention of preterm labor, premature birth, dysmenorrhea, and for stopping labor prior to cesarean delivery. The primary symmetric center of the compounds according to formula (I) is the one in position 2 of the piperazine-2-carboxamide, thus providing either R or S enantiomers. Such enantiomers may be obtained from the pure R or S precursors or by separation of the racemate e.g. using chiral techniques known by a person skilled in the art.

Preferred pharmaceutically acceptable salts of the formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

The substituents within formula (I) are defined as follows:

A and B are each independently from each other selected from the group consisting of straight or branched substituted or unsubstituted $C_1$-$C_6$ alkyl, substituted or unsubstituted $C_2$-$C_6$-alkenyl, substituted or unsubstituted $C_2$-$C_6$-alkynyl, substituted or unsubstituted $C_3$-$C_8$-cycloalkyl, substituted or unsubstituted 3-8 membered heterocycloalkyl, straight or branched substituted or unsubstituted $C_1$-$C_6$-alkyl-(3-8 membered)heterocycloalkyl, substituted or unsubstituted aryl, straight or branched substituted or unsubstituted ($C_1$-$C_6$) alkyl-aryl, substituted or unsubstituted $C_2$-$C_6$-alkenyl-aryl, substituted or unsubstituted $C_2$-$C_6$-alkynyl-aryl, substituted or unsubstituted heteroaryl, straight or branched substituted or unsubstituted $C_1$-$C_6$-alkyl-heteroaryl group, substituted or unsubstituted $C_2$-$C_6$-alkenyl-heteroaryl, substituted or unsubstituted $C_2$-$C_6$-alkynyl-heteroaryl, an acyl, $C_1$-$C_6$-alkoxy, wherein said cycloalkyl, heterocycloalkyl, aryl or heteroaryl may be fused with cycloalkyl, aryl or heteroaryl groups.

X is selected from the group consisting of —CO— or —SO$_2$—, preferably —SO$_2$—.

Y is selected in the group consisting of —SO$_2$—, —CO—, —CO—NR$^3$ wherein R$^3$ is H or a straight or branched substituted or unsubstituted C$_1$-C$_6$-alkyl.

R$^1$ and R$^2$ are each independently from each other selected from the group consisting of hydrogen, hydroxy, sulfonyl, amino, substituted or unsubstituted C$_1$-C$_6$-alkyl, substituted or unsubstituted C$_2$-C$_6$-alkenyl, substituted or unsubstituted C$_2$-C$_6$-alkynyl wherein said alkyl, alkenyl or alkynyl chains may be interrupted by a heteroatom selected from N, O or S, substituted or unsubstituted aryl, substituted or unsubstituted heteroaryl, substituted or unsubstituted 3-8-membered cycloalkyl, substituted or unsubstituted heterocycloalkyl, wherein said cycloalkyl, heterocycloalkyl, aryl or heteroaryl groups may be fused with 1-2 further substituted or unsubstituted cycloalkyl, substituted or unsubstituted heterocycloalkyl, substituted or unsubstituted aryl or substituted or unsubstituted heteroaryl group, an acyl moiety, substituted or unsubstituted C$_1$-C$_6$-alkyl aryl, substituted or unsubstituted C$_1$-C$_6$-alkyl heteroaryl, substituted or unsubstituted C$_2$-C$_6$-alkenyl aryl, substituted or unsubstituted C$_2$-C$_6$-alkenyl heteroaryl, substituted or unsubstituted C$_2$-C$_6$-alkynyl aryl, substituted or unsubstituted C$_2$-C$_6$-alkynyl heteroaryl, substituted C$_1$-C$_6$-alkyl cycloalkyl, substituted or unsubstituted C$_1$-C$_6$-alkyl heterocycloalkyl, substituted or unsubstituted C$_2$-C$_6$-alkenyl cycloalkyl, substituted or unsubstituted C$_2$-C$_6$-alkenyl heterocycloalkyl, substituted or unsubstituted C$_2$-C$_6$-alkynyl cycloalkyl, substituted or unsubstituted C$_2$-C$_6$-alkynyl heterocycloalkyl, substituted or unsubstituted C$_1$-C$_6$alkyl carboxy, substituted or unsubstituted C$_1$-C$_6$-alkyl acyl, substituted or unsubstituted aryl acyl, substituted or unsubstituted heteroaryl acyl, substituted or unsubstituted C$_3$-C$_8$-(hetero)cycloalkyl acyl, substituted or unsubstituted C$_1$-C$_6$-alkyl acyloxy, substituted or unsubstituted C$_1$-C$_6$-alkyl alkoxy, substituted or unsubstituted C$_1$-C$_6$-alkyl alkoxycarbonyl, substituted or unsubstituted C$_1$-C$_6$-alkyl aminocarbonyl, substituted or unsubstituted C$_1$-C$_6$-alkyl acylamino, acylamino, substituted or unsubstituted C$_1$-C$_6$-alkyl ureido, substituted or unsubstituted C$_1$-C$_6$-alkyl carbamate, substituted or unsubstituted C$_1$-C$_6$alkyl amino, substituted or unsubstituted C$_1$-C$_6$-alkyl ammonium, substituted or unsubstituted C$_1$-C$_6$-alkyl sulfonyloxy, substituted or unsubstituted C$_1$-C$_6$-alkyl sulfonyl, substituted or unsubstituted C$_1$-C$_6$alkyl sulfinyl, substituted or unsubstituted C$_1$-C$_6$-alkyl sulfanyl, substituted or unsubstituted C$_1$-C$_6$-alkyl sulfonylamino or substituted or unsubstituted C$_1$-C$_6$-alkyl aminosulfonyl and R$^1$ and R$^2$ may form together a substituted or unsubstituted 3-8 membered heterocycle optionally comprising a heteroatom selected from O, N or S;

In a specific embodiment, A and B are each independently from each other a substituted or unsubstituted aryl or a substituted or unsubstituted heteroaryl (e.g. a substituted or unsubstituted phenyl, like a biphenyl moiety, a substituted or unsubstituted thienyl, a substituted or unsubstituted quinolyl).

In still a further embodiment when X and Y are each independently from each other —SO$_2$— or —CO— and A and B are each independently from each other selected from substituted or unsubstituted aryl or substituted or unsubstituted heteroaryl (e.g. a substituted or unsubstituted phenyl, a substituted or unsubstituted thienyl, a substituted or unsubstituted quinolyl).

Specific examples of compounds of formula (I) include those specified in the Examples 1 to 178 below.

A further aspect of the invention consists in novel quinoline piperazine-2-carboxamide derivatives of formula (II),

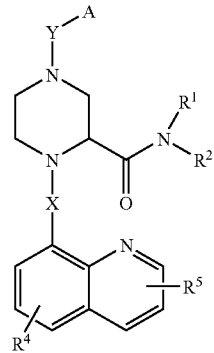

(II)

as well as its geometrical isomers, its optically active forms as enantiomers, diastereomers and its racemate forms, as well as pharmaceutically acceptable salts and pharmaceutically active derivatives thereof wherein A, X, Y, R$^1$, R$^2$ are as above-mentioned.

R$^4$ and R$^5$ are each independently from each other selected from the group consisting of straight or branched substituted or unsubstituted C$_1$-C$_6$-alkyl, substituted or unsubstituted C$_2$-C$_6$-alkenyl, substituted or unsubstituted C$_2$-C$_6$-alkynyl, substituted or unsubstituted aryl, substituted or unsubstituted heteroaryl, substituted or unsubstituted C$_3$-C$_8$-cycloalkyl or substituted or unsubstituted heterocycloalkyl, substituted or unsubstituted C$_1$-C$_6$-alkyl aryl, substituted or unsubstituted C$_1$-C$_6$-alkyl heteroaryl, substituted or unsubstituted C$_1$-C$_6$-alkyl cycloalkyl, substituted or unsubstituted C$_1$-C$_6$-alkyl heterocycloalkyl, substituted or unsubstituted C$_2$-C$_6$-alkenyl-aryl or -heteroaryl, substituted or unsubstituted C$_2$-C$_6$-alkynyl aryl or -heteroaryl, carboxy, cyano, halogen, hydroxy, substituted or unsubstituted C$_1$-C$_6$-alkoxy, amino, C$_1$-C$_6$-alkylamino, nitro, acylamino, ureido, sulfonylamino, sulfanyl or sulfonyl.

In one embodiment, X is —SO$_2$—, Y is —SO$_2$—, —CO— or —CO—NR$^3$— wherein R$^3$ is H or a straight or branched substituted or unsubstituted (C$_1$-C$_6$)-alkyl (e.g. a methyl group), A is substituted or unsubstituted aryl or substituted or unsubstituted heteroaryl, R$^1$ is H or —CH$_3$, R$^2$ is straight or branched substituted or unsubstituted (C$_1$-C$_6$)-alkyl, substituted or unsubstituted (C$_2$-C$_6$)-alkenyl (e.g. a propenyl or a butenyl moiety), substituted or unsubstituted aryl, substituted or unsubstituted (C$_1$-C$_6$)-alkyl aryl, substituted or unsubstituted heteroaryl, substituted or unsubstituted (C$_1$-C$_6$)-alkyl-heteroaryl, substituted or unsubstituted cycloalkyl, substituted or unsubstituted (C$_1$-C$_6$)-alkyl-cycloalkyl, substituted or unsubstituted 3-8-membered heterocycloalkyl, substituted or unsubstituted (C$_1$-C$_6$)-3-8-membered heterocycloalkyl.

Alternatively, R$^1$ and R$^2$ may form together with the nitrogen to which they are bound, or without the nitrogen to which they are bound, a substituted or unsubstituted 3-8-membered cylcoalkyl or heterocycle moiety. In a specific embodiment, R$^1$ is H or —CH$_3$.

In a specific embodiment R$^4$ and R$^5$ are both H.

In a more specific embodiment, X is —SO$_2$—, Y is —CO—, —CONH—, —SO$_2$—, A is a substituted or unsubstituted phenyl (e.g. a phenoxyphenyl, benzyloxyphenyl, 4-tert-butylphenyl, biphenyl, halogenated phenyl), a substituted or unsubstituted C$_1$-C$_6$ alkyl (diphenylmethyl).

In still another embodiment R² is selected from the following moieties: hydroxyethyl, substituted or unsubstituted propen-2-enyl, substituted or unsubstituted 3-hydroxy-1-phenyl propyl, substituted or unsubstituted 2-hydroxy-1-phenyl ethyl, substituted or unsubstituted prop-2-enyl, substituted or unsubstituted methoxyphenyl, substituted or unsubstituted 2-hydroxy-2-phenyl ethyl, substituted or unsubstituted 2,2 diphenylethyl, 1-ethyl pyrrolidin1-2-yl, substituted or unsubstituted 1,3 benzodioxol-5-yl-methyl, substituted or unsubstituted 2-furylmethyl, substituted or unsubstituted benzyl, substituted or unsubstituted pyridin-4yl-methyl, substituted or unsubstituted 2-(hydroxymethyl)piperidin-1-yl, substituted or unsubstituted 2-hydroxyethyl, substituted or unsubstituted 2-hydroxy-2-phenyl ethyl or substituted or unsubstituted cyclopropyl.

Alternatively, R¹ and R² together may form with the nitrogen to which they are bound a substituted or unsubstituted piperidine.

Specific piperazine-2-carboxamide derivatives according to formula (II) comprise the following:

(2S)-4-[(4-tert-butylphenyl)sulfonyl]-N-(2-hydroxyethyl)-1-(quinolin-8-yl-sulfonyl)piperazine-2-carboxamide;

(2R)-4-[(4-tert-butylphenyl)sulfonyl]-N-(2-hydroxyethyl)-1-(quinolin-8-yl-sulfonyl)piperazine-2-carboxamide;

(2S)-4-[(4-tert-butylphenyl)sulfonyl]-N-prop-2-enyl-1-(quinolin-8-yl-sulfonyl)piperazine-2-carboxamide;

(2R)-4-[(4-tert-butylphenyl)sulfonyl]-N-prop-2-enyl-1-(quinolin-8-yl-sulfonyl)piperazine-2-carboxamide;

(2R)-4-[(4-tert-butylphenyl)sulfonyl]-N-[(1S)-3-hydroxy-1-phenylpropyl]-1-(quinolin-8-yl-sulfonyl)piperazine-2-carboxamide;

(2R)-4-[(4-tert-butylphenyl)sulfonyl]-N-[(1R)-3-hydroxy-1-phenylpropyl]-1-(quinolin-8-yl-sulfonyl)piperazine-2-carboxamide;

(2R)-4-[(4-tert-butylphenyl)sulfonyl]-N-[(1R)-2-hydroxy-1-phenylethyl]-1-quinolin-8-yl-sulfonyl)piperazine-2-carboxamide;

(2R)-4-[(4-tert-butylphenyl)sulfonyl]-N-[(1S)-2-hydroxy-1-phenylethyl]-1-(quinolin-8yl-sulfonyl)piperazine-2carboxamide;

4-(diphenylacetyl)-N-(2-furylmethyl)-1-(quinolin-8-ylsulfonyl)piperazine-2-carboxamide;

4-Diphenylacetyl-1-(quinolin-8-sulfonyl)-piperazine-2-carboxylic acid (pyridin-4-ylmethyl)-amide;

4-Diphenylacetyl-1-(quinoline-8-sulfonyl)-piperazine-2-carboxylic acid benzylamide;

4-Diphenylacetyl-1-(quinoline-8-sulfonyl)-piperazine-2-carboxylic acid (thiophen-2-ylmethyl)-amide;

4-Diphenylacetyl-1-(quinoline-8-sulfonyl)-piperazine-2-carboxylic acid (pyridin-2-ylmethyl)-amide;

(R)—N~1~-biphenyl-2-yl-N~3~-[3-(1H-imidazol-1-yl)propyl]-4-(quinolin-8-ylsulfonyl)piperazine-1,3-dicarboxamide;

(S)—N~1~-biphenyl-2-yl-N~3~-[3-(1H-imidazol-1-yl)propyl]-4-(quinolin-8-ylsulfonyl)piperazine-1,3-dicarboxamide;

N~1~-biphenyl-2-yl-N~3~-(2,3-dihydro-1H-inden-1-yl)-4-quinolin-8-ylsulfonyl)piperazine-1,3-dicarboxamide;

N~1~-biphenyl-2-yl-N~3~-(2-phenylpropyl)-4-(quinolin-8-ylsulfonyl)piperazine-1,3-dicarboxamide;

N~3~-(4-methoxyphenyl)-N~1~-phenyl-4-(quinolin-8-ylsulfonyl)piperazine-1,3-dicarboxamide;

N~3~-(2-hydroxy-2-phenylethyl)-N~3~-methyl-N~1~-(4-phenoxyphenyl)-4-(quinolin-8-ylsulfonyl)piperazine-1,3-dicarboxamide;

4-benzoyl-N-(diphenylmethyl)-1-(quinolin-8-ylsulfonyl)piperazine-2-carboxamide;

N-(diphenylmethyl)-4-(pyridin-2-ylcarbonyl)-1-(quinolin-8-ylsulfonyl)piperazine-2-carboxamide;

N-(diphenylmethyl)-4-(3-piperidin-1-ylpropanoyl)-1-(quinolin-8-ylsulfonyl)piperazine-2-carboxamide;

N-(diphenylmethyl)-4-(phenoxyacetyl)-1-(quinolin-8-ylsulfonyl)piperazine-2-carboxamide;

N-(diphenylmethyl)-4-[(4-methoxyphenyl)acetyl]-1-(quinolin-8-ylsulfonyl)piperazine-2-carboxamide;

4-[4-(dimethylamino)benzoyl]-N-(diphenylmethyl)-1-(quinolin-8-ylsulfonyl)piperazine-2-carboxamide;

4-(cyclohexylcarbonyl)-N-(diphenylmethyl)-1-(quinolin-8-ylsulfonyl)piperazine-2-carboxamide;

4-acetyl-N-(2,4-dichlorobenzyl)-1-(quinolin-8-ylsulfonyl)piperazine-2-carboxamide;

4-benzoyl-N-(2,4-dichlorobenzyl)-1-(quinolin-8-ylsulfonyl)piperazine-2-carboxamide;

N-(2,4-dichlorobenzyl)-4-(pyridin-2-ylcarbonyl)-1-(quinolin-8-ylsulfonyl)piperazine-2-carboxamide;

N-(2,4-dichlorobenzyl)-4-(3-piperidin-1-ylpropanoyl)-1-(quinolin-8-ylsulfonyl)piperazine-2-carboxamide;

N-(2,4-dichlorobenzyl)-4-(phenoxyacetyl)-1-(quinolin-8-ylsulfonyl)piperazine-2-carboxamide;

N-(2,4-dichlorobenzyl)-4-[(2-oxo-6-pentyl-2H-pyran-3-yl)carbonyl]-1-(quinolin-8-ylsulfonyl)piperazine-2-carboxamide;

N-(2,4-dichlorobenzyl)-4-(diphenylacetyl)-1-(quinolin-8-ylsulfonyl)piperazine-2-carboxamide;

N-(2,4-dichlorobenzyl)-4-[(4-methoxyphenyl)acetyl]-1-(quinolin-8-ylsulfonyl)piperazine-2-carboxamide;

N-(2,4-dichlorobenzyl)-4-[4-(dimethylamino)benzoyl]-1-quinolin-8-ylsulfonyl)piperazine-2-carboxamide;

4-benzoyl-N-(2,2-diphenylethyl)-1-(quinolin-8-ylsulfonyl)piperazine-2-carboxamide;

N-(2,2-diphenylethyl)-4-(pyridin-2-ylcarbonyl)-1-(quinolin-8-ylsulfonyl)piperazine-2-carboxamide;

N-(2,2-diphenylethyl)-4-(3-piperidin-1-ylpropanoyl)-1-quinolin-8-ylsulfonyl)piperazine-2-carboxamide;

N-(2,2-diphenylethyl)-4-[(4-methoxyphenyl)acetyl]-1-(quinolin-8-ylsulfonyl)piperazine-2-carboxamide;

4-[4-(dimethylamino)benzoyl]-N-(2,2-diphenylethyl)-1-(quinolin-8-ylsulfonyl)piperazine-2-carboxamide;

4-(diphenylacetyl)-N-[(1-ethylpyrrolidin-2-yl)methyl]-1-(quinolin-8-ylsulfonyl)piperazine-2-carboxamide;

N-allyl-4-(diphenylacetyl)-1-quinolin-8-ylsulfonyl)piperazine-2-carboxamide;

N-(1,3-benzodioxol-5-ylmethyl)-4-[(2E)-3-phenylprop-2-enoyl]-1-(quinolin-8-ylsulfonyl)piperazine-2-carboxamide;

N-(1,3-benzodioxol-5-ylmethyl)-4-(diphenylacetyl)-1-(quinolin-8-ylsulfonyl)piperazine-2-carboxamide;

N-(1,3-benzodioxol-5-ylmethyl)-4-[4-(dimethylamino)benzoyl]-1-quinolin-8-ylsulfonyl)piperazine-2-carboxamide;

4-(diphenylacetyl)-N-(3-ethoxypropyl)-1-(quinolin-8-ylsulfonyl)piperazine-2-carboxamide;

N-(2-furylmethyl)-4-[(2-oxo-6-pentyl-2H-pyran-3-yl)carbonyl]-1-(quinolin-8-ylsulfonyl)piperazine-2-carboxamide;

N-benzyl-4-(phenoxyacetyl)-1-(quinolin-8-ylsulfonyl)piperazine-2-carboxamide;

N-benzyl-4-[(2-oxo-6-pentyl-2H-pyran-3-yl)carbonyl]-1-quinolin-8-ylsulfonyl)piperazine-2-carboxamide;

N-benzyl-4-[4-(dimethylamino)benzoyl]-1-(quinolin-8-ylsulfonyl)piperazine-2-carboxamide;

3-{[3-{[2-(hydroxymethyl)piperidin-1-yl]carbonyl}-4-(quinolin-8-ylsulfonyl)piperazine-1-yl]carbonyl}-6-pentyl-2H-pyran-2-one;

4-(diphenylacetyl)-N-[4-(hydroxymethyl)phenyl]-1-(quinolin-8-ylsulfonyl)piperazine-2-carboxamide;

4-(diphenylacetyl)-N-(4-fluorobenzyl)-1-(quinolin-8-ylsulfonyl)piperazine-2-carboxamide;

4-(diphenylacetyl)-N-(2-phenylpropyl)-1-(quinolin-8-ylsulfonyl)piperazine-2-carboxamide;

4-[(4-methoxyphenyl)acetyl]-N-(2-phenylpropyl)-1-(quinolin-8-ylsulfonyl)piperazine-2-carboxamide;

N~1~-biphenyl-2-yl-N~3~-(4-fluorobenzyl)-4-(quinolin-8-ylsulfonyl)piperazine-1,3-dicarboxamide;

1-(3-chlorobenzoyl)-N-(diphenylmethyl)-4-(quinolin-8-ylsulfonyl)piperazine-2-carboxamide;

1-(3-chlorobenzoyl)-N-(2-phenylpropyl)-4-(quinolin-8-ylsulfonyl)piperazine-2-carboxamide;

N-allyl-4-[(4-tert-butylphenyl)sulfonyl]-1-(quinolin-8-ylsulfonyl)piperazine-2-carboxamide;

N-allyl-4-(biphenyl-4-ylsulfonyl)-1-(quinolin-8-ylsulfonyl)piperazine-2-carboxamide;

4-[(4-tert-butylphenyl)sulfonyl]-N-(2-hydroxyethyl)-1-(quinolin-8-ylsulfonyl)piperazine-2-carboxamide;

4-[(4-tert-butylphenyl)sulfonyl]-N-(2-furylmethyl)-1-(quinolin-8-ylsulfonyl)piperazine-2-carboxamide;

4-[(4-tert-butylphenyl)sulfonyl]-N-(pyridin-4-ylmethyl)-1-(quinolin-8-ylsulfonyl)piperazine-2-carboxamide;

N-(2-phenylpropyl)-4-(phenylsulfonyl)-1-(quinolin-8-ylsulfonyl)piperazine-2-carboxamide;

N-(2-phenylpropyl)-1,4-bis(quinolin-8-ylsulfonyl)piperazine-2-carboxamide;

4-[(4-methoxyphenyl)sulfonyl]-N-(2-phenylpropyl)-1-(quinolin-8-ylsulfonyl)piperazine-2-carboxamide;

4-[(3,4-dimethoxyphenyl)sulfonyl]-N-2-phenylpropyl)-1-(quinolin-8-ylsulfonyl)piperazine-2-carboxamide;

4-[(4-methylphenyl)sulfonyl]-N-(2-phenylpropyl)-1-(quinolin-8-ylsulfonyl)piperazine-2-carboxamide;

4-[(4-nitrophenyl)sulfonyl]-N-(2-phenylpropyl)-1-(quinolin-8-ylsulfonyl)piperazine-2-carboxamide;

4-(biphenyl-4-ylsulfonyl)-N-(2-hydroxy-2-phenylethyl)-1-(quinolin-8-ylsulfonyl)piperazine-2-carboxamide;

4-[(4-tert-butylphenyl)sulfonyl]-N-cyopropyl-1-(quinolin-8-ylsulfonyl)piperazine-2-carboxamide;

N~1~-(2-cyanophenyl)-N~3~-(diphenylmethyl)-4-(quinolin-8-ylsulfonyl)piperazine-1,3-dicarboxamide;

N~1~-biphenyl-2-yl-N~3~-(2-furylmethyl)-4-(quinolin-8-ylsulfonyl)piperazine-1,3-dicarboxamide;

N~3~-benzyl-N~1~-biphenyl-2-yl-4-(quinolin-8-ylsulfonyl)piperazine-1,3-dicarboxamide;

N~1~-biphenyl-2-yl-4-(quinolin-8-ylsulfonyl)-N~3~-(2-thienylmethyl)piperazine-1,3-dicarboxamide;

4-(diphenylacetyl)-N-(pyridin-3-ylmethyl)-1-(quinolin-8-ylsulfonyl)piperazine-2-carboxamide.

A further aspect of the invention consists in novel biphenyl piperazine-2-carboxamide derivatives of formula (III),

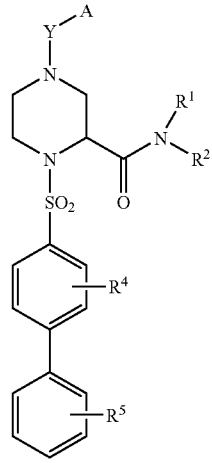

(III)

as well as its geometrical isomers, its optically active forms as enantiomers, diastereomers and its racemate forms, as well as pharmaceutically acceptable salts and pharmaceutically active derivatives thereof, wherein A, Y, $R^1$, $R^2$, $R^3$, $R^4$ and $R^5$ are as above-defined.

In one embodiment, A is a substituted or unsubstituted phenyl (e.g. a biphenyl), substituted or unsubstituted thienyl, Y is —$SO_2$— or —$CONR^3$— wherein $R^3$ is H or a straight or branched substituted or unsubstituted ($C_1$-$C_6$)-alkyl, $R^1$ is H or a straight or branched substituted or unsubstituted ($C_1$-$C_6$)-alkyl, $R^2$ is a straight or branched substituted or unsubstituted ($C_1$-$C_6$)-alkyl, substituted or unsubstituted ($C_1$-$C_6$)-alkyl-heterocycle or -heteroaryl, or alternatively $R^1$ and $R^2$ may form together with the nitrogen to which they are bound a substituted or unsubstituted 3-8-membered heterocycle (e.g. a piperazine).

In another embodiment, $R^4$ and $R^5$ are both hydrogen.

Specific piperazine-2-carboxamide derivatives according to formula (I) are:

4-(2'-Methyl-biphenyl-4-sulfonyl)-piperazine-1,3-dicarboxylic acid 3-[(1-ethyl-pyrrolidin-2-ylmethyl)-amide]1-[(4-phenoxy-phenyl)amide]

(3R)-4-(Biphenyl-4-sulfonyl)-piperazine-1,3-dicarboxylic acid 1-[(4-benzyloxy-phenyl)-amide]-3-{(2R)[1-ethyl-pyrrolidin-2-ylmethyl]-amide}

(3R)-4-(Biphenyl-4-sulfonyl)-piperazine-1,3-dicarboxylic acid 1-[(4-benzyloxy-phenyl)-amide]-3-{(2S)[1-ethyl-pyrrolidin-2-ylmethyl]-amide}

(3S)-4-(Biphenyl-4-sulfonyl)-piperazine-1,3-dicarboxylic acid 1-[(4-benzyloxy-phenyl)-amide]-3-{(2S)[1-ethyl-pyrrolidin-2-ylmethyl]-amide}

(3S)-4-(Biphenyl-4-sulfonyl)-piperazine-1,3-dicarboxylic acid 1-[(4-benzyloxy-phenyl)-amide]-3-{(2R)[1-ethyl-pyrrolidin-2-ylmethyl]-amide}

4-(Biphenyl-4sulfonyl)-piperazine-1,3-dicarboxylic acid 1-[(4-benzyloxy-phenyl)-amide]3-[(2-dimethylamino-ethyl)-amide]

4-(Biphenyl-4-sulfonyl)-piperazine-1,3-dicarboxylic acid 3-[(2-dimethylamino-ethyl)-amide]1-[(4-phenoxy-phenyl)-amide]

4-(Biphenyl-4-sulfonyl)-piperazine-1,3-dicarboxylic acid 1-[(3,4-dichloro-phenyl)-amide]3-[(1-ethyl-pyrrolidin-2-ylmethyl)-amide]

4-(Biphenyl-4-sulfonyl)-piperazine-1,3-dicarboxylic acid 3-[(1-ethyl-pyrrolidin-2-ylmethyl)-amide]1-[(4-phenoxy-phenyl)-amide]

4-(Biphenyl-4-sulfonyl)-piperazine-1,3-dicarboxylic acid 1-[(3,4-dichloro-phenyl)-amide]3-[(2-diethylamino-ethyl)-amide]

4-(Biphenyl-4-sulfonyl)-piperazine-1,3-dicarboxylic acid 1-[(4-benzyloxy-phenyl)-amide]3-[(2-diethylamino-ethyl)-amide]

4-(Biphenyl-4-sulfonyl)-piperazine-1,3-dicarboxylic acid 3-[(2-diethylamino-ethyl)-amide]1-[(4-phenoxy-phenyl)-amide]

N-1,1'-biphenyl-2-yl-4-(1,1'-biphenyl-4-ylsulfonyl)-3-{[2-hydroxymethyl)piperidin-1-yl]carbonyl}piperazine-1-carboxamide N~1~-biphenyl-2-yl-4-(biphenyl-4-ylsulfonyl)-N~3~-[2-(diethylamino)ethyl]piperazine-1,3-dicarboxamide 1-(biphenyl-4-ylsulfonyl)-4-[(4-tert-butylphenyl)sulfonyl]-N-[(1-ethylpyrrolidin-2-yl)methyl]piperazine-2-carboxamide 1-(biphenyl-4-ylsulfonyl)-4-[(5-{[(4-chlorobenzoyl)amino]methyl}-2-thienyl)sulfonyl]-N-[(1-ethylpyrrolidin-2-yl)methyl]piperazine-2-carboxamide 1-(biphenyl-4-ylsulfonyl)-N-[(1-ethylpyrrolidin-2-yl)methyl]-4-(4-phenoxybenzoyl)-piperazine-2-carboxamide Further novel compounds of formula (I) are:

1-benzoyl-4-[(4-tert-butylphenyl)sulfonyl]-N-(2-furylmethyl)piperazine-2-carboxamide 1-benzoyl-4-(biphenyl-4-ylsulfonyl)-N-(2-furylmethyl)piperazine-2-carboxamide 1-benzoyl-N-benzyl-4-[(4-tert-butylphenyl)sulfonyl]piperazine-2-carboxamide N-2,3-dihydro-1H-inden-1-yl)-4-(diphenylacetyl)-1-(phenylsulfonyl)piperazine-2-carboxamide N-(2-hydroxy-2-phenylethyl)-4-(phenoxyacetyl)-1-(phenylsulfonyl)piperazine-2-carboxamide 1-benzoyl-N-(diphenylmethyl)-4-(quinolin-8-ylsulfonyl)piperazine-2-carboxamide 1-benzoyl-4-(diphenylacetyl)-N-(diphenylmethyl)piperazine-2-carboxamide 1-benzoyl-N-(diphenylmethyl)-4-[(4-methoxyphenyl)acetyl]piperazine-2-carboxamide 1-benzoyl-N-(4-fluorobenzyl)-4-(4-phenoxybenzoyl)piperazine-2-carboxamide 1-benzoyl-4-(diphenylacetyl)-N-(4-fluorobenzyl)piperazine-2-carboxamide 1-benzoyl-4-(diphenylacetyl)-N-(1-naphthylmethyl)piperazine-2-carboxamide 1-benzoyl-4-[(4-methoxyphenyl)acetyl]-N-(1-naphthylmethyl)piperazine-2-carboxamide 1-benzoyl-4-(cyclohexylcarbonyl)-N-(1-naphthylmethyl)piperazine-2-carboxamide 1-benzoyl-N-(2,3-dihydro-1H-inden-1-yl)-4-(diphenylacetyl)piperazine-2-carboxamide 1-benzoyl-4-(diphenylacetyl)-N-(2-phenylpropyl)piperazine-2-carboxamide 1-benzoyl-4-(diphenylacetyl)-N-(4-methoxyphenyl)piperazine-2-carboxamide 4-acetyl-N-(1,3-benzodioxol-5-ylmethyl)-1-phenylsulfonyl)piperazine-2-carboxamide 4-(diphenylacetyl)-N-(2-furylmethyl)-1-(phenylsulfonyl)piperazine-2-carboxamide 4-acetyl-N-benzyl-1-(phenylsulfonyl)piperazine-2-carboxamide 4-benzoyl-N-benzyl-1-(phenylsulfonyl)piperazine-2-carboxamide N-benzyl-4-(diphenylacetyl)-1-(phenylsulfonyl)piperazine-2-carboxamide 4-acetyl-1-(phenylsulfonyl)-N-(2-thienylmethyl)piperazine-2-carboxamide 4-(diphenylacetyl)-1-(phenylsulfonyl)-N-(2-thienylmethyl)piperazine-2-carboxamide N~1~-(2-cyanophenyl)-N~3~-(1-naphthylmethyl)-4-(phenylsulfonyl)piperazine-1,3-dicarboxamide N-(2,3-dihydro-1H-inden-1-yl)-4-[(4-methoxyphenyl)sulfonyl]-1-(2-thienylsulfonyl)piperazine-2-carboxamide (1-{[4-(diphenylacetyl)-1-(2-thienylsulfonyl)piperazine-2-yl]carbonyl}piperidin-2-yl)methanol 4-(diphenylacetyl)-N-[4-(hydroxymethyl)phenyl]-1-(2-thienylsulfonyl)piperazine-2-carboxamide 4-(diphenylacetyl)-N-(4-fluorobenzyl)-1-(2-thienylsulfonyl)piperazine-2-carboxamide 1-benzoyl-4-[(3,4-dimethoxyphenyl)sulfonyl]-N-(2-phenylpropyl)piperazine-2-carboxamide 1-benzoyl-4-[(4-nitrophenyl)sulfonyl]-N-(2-phenylpropyl)piperazine-2-carboxamide N~1~,4-dibenzoyl-N~3~-(diphenylmethyl)piperazine-1,3-dicarboxamide 4-benzoyl-N~3~-(2,2-diphenylethyl)-N~1~-(3-methoxyphenyl)piperazine-1,3-dicarboxamide N~1~-benzoyl-N~3~-(diphenylmethyl)-4-(phenylsulfonyl)piperazine-1,3-dicarboxamide N~1~-(3,4-dichlorophenyl)-N~3~-(2-hydroxy-2-phenylethyl)-N~3~-methyl-4-(phenylsulfonyl)piperazine-1,3-dicarboxamide N~3~-(2-hydroxy-2-phenylethyl)-N~3~-methyl-N~1~-(4-phenoxyphenyl)-4-(phenylsulfonyl)piperazine-1,3-dicarboxamide N~3~-[1,1-bis(hydroxymethyl)propyl]-N~1~-(2-cyanophenyl)-4-(2-thienylsulfonyl)piperazine-1,3-dicarboxamide N~1~-[4-(benzyloxy)phenyl]-N~3~-(2-hydroxy-2-phenylethyl)-N~3~-methyl-4-(2-thienylsulfonyl)piperazine-1,3-dicarboxamide N~3~-(2-hydroxy-2-phenylethyl)-N~3~-methyl-N~1~-(4-phenoxyphenyl)-4-(2-thienylsulfonyl)piperazine-1,3-dicarboxamide N-butyl-4-diphenylacetyl-1-(2-thienylsulfonyl)piperazine-2-carboxamide 4-(diphenylacetyl)-N-(2-furylmethyl)-1-(2-thienylsulfonyl)piperazine-2-carboxamide N-benzyl-4-(diphenylacetyl)-1-(2-thienylsulfonyl)piperazine-2-carboxamide 4-(diphenylacetyl)-N-(2-thienylmethyl)-1-(2-thienylsulfonyl)piperazine-2-carboxamide N-(2,3-dihydro-1H-inden-1-yl)-4-(diphenylacetyl)-1-(2-thienylsulfonyl)piperazine-2-carboxamide 4-(diphenylacetyl)-N-(2-phenylpropyl)-1-(2-thienylsulfonyl)piperazine-2-carboxamide N~3~-(2-furylmethyl)-~1~-pentyl-4-(phenylsulfonyl)piperazine-1,3-dicarboxamide 4-(biphenyl-4-ylsulfonyl)-N~3~-[(1-ethylpyrrolidin-2-yl)methyl]-N~1~-(3-methoxyphenyl)piperazine-1,3-dicarboxamide N~1~-[4-(benzyloxy)phenyl]-4-(biphenyl-4-ylsulfonyl)-N~3~-[(1-ethylpyrrolidin-2-yl)methyl]piperazine-1,3-dicarboxamide N~3~-(4-methoxyphenyl)-N~1~-phenyl-4-(quinolin-8-ylsulfonyl)piperazine-1,3-dicarboxamide N~3~-(2-hydroxy-2-phenylethyl)-N~3~-methyl-N~1~-(4-phenoxyphenyl)-4-(quinolin-8-ylsulfonyl)piperazine-1,3 dicarboxamide 3-{[3-{[2-(hydroxymethyl)piperidin-1-yl]carbonyl}-4-(quinolin-8-ylsulfonyl)piperazine-1-yl]carbonyl}-6-pentyl-2H-pyran-2-one 1-(3-chlorobenzoyl)-N-(diphenylmethyl)-4-(quinolin-8-ylsulfonyl)piperazine-2-carboxamide 1-(3-chlorobenzoyl)-N-(2-phenylpropyl)-4-(quinolin-8-yl-sulfonyl)piperazine-2-carboxamide 4-(3-chlorobenzoyl)-N~1~-(3,4-dichlorophenyl)-N~3~-(2,3-dihydro-1H-inden-1-yl)piperazine-1,3-dicarboxamide 4-(3-chlorobenzoyl)-N~3~-(2,3-dihydro-1H-inden-1-yl)-N~1~-(3-methoxyphenyl)piperazine-1,3-dicarboxamide 4-(3-chlorobenzoyl)-N~1~-(3,4-dichlorophenyl)-N~3~-(2-phenylpropyl)piperazine-1,3-dicarboxamide 4-(3-chlorobenzoyl)-N~1~-(2-cyanophenyl)-N~3~-(2-phenylpropyl)piperazine-1,3-dicarboxamide 4-benzoyl-1-(3-chlorobenzoyl)-N-(diphenylmethyl)piperazine-2-carboxamide 1-(3-chlorobenzoyl)-N-(diphenylmethyl)-4-(3-piperidin-1-ylpropanoyl)piperazine-2-carboxamide 1-(3-chlorobenzoyl)-N-(diphenylmethyl)-4-(phenoxyacetyl)piperazine-2-carboxamide 1-(3-chlorobenzoyl)-N-(diphenylmethyl)-4-[(4-methoxyphenyl)acetyl]piperazine-2-carboxamide 1-(3-chlorobenzoyl)-4-(cyclohexylcarbonyl)-N-(diphenylmethyl)piperazine-2-carboxamide 1-(3-chlorobenzoyl)-4-(diphenylacetyl)-N-(2,2-diphenylethyl)piperazine-2-carboxamide N-(2,4-dichlorobenzyl)-4-[(3,4-dimethoxyphenyl)sulfonyl]-1-(2-thienylsulfonyl)-piperazine-2-carboxamide N-biphenyl-2-yl-4-(biphenyl-4-ylsulfonyl)-3-{[2-hydroxymethyl)piperidin-1-yl]carbonyl}piperazine-1-carboxamide N~1~-[4-(benzyloxy)phenyl]-4-(biphenyl-4-ylsulfonyl)-N~3~-(2-morpholin-4-ylethyl)piperazine-1,3-dicarboxamide 4-(biphenyl-4-ylsulfonyl)-N~3~-(2-morpholin-4-ylethyl)-N~1~-(4-phenoxyphenyl)-piperazine-1,3-dicarboxamide N~1~-[4-benzyloxy)phenyl]-4-(biphenyl-4-ylsulfonyl)-N~3~-[3-(1H-imidazol-1-yl)propyl]piperazine-1,3-dicarboxamide 4-(biphenyl-4-ylsulfonyl)-N~3~-[3-(1H-imidazol-1-yl)propyl]-N~1~-(4-phenoxyphenyl)-piperazine-1,3-dicarboxamide N-allyl-4-[(4-tert-butylphenyl)sulfonyl]-1-(quinolin-8-ylsulfonyl)piperazine-2-carboxamide N~1~-(2-cyanophenyl)-N~3~-(diphenylmethyl)-4-(quinolin-8-ylsulfonyl)piperazine-1,3-dicarboxamide 4-(biphenyl-4-ylsulfonyl)-N~1~-(3,4-dichlorophenyl)-N~3~-[2-(dimethylamino)ethyl]-piperazine-1,3-dicarboxamide N~1~-biphenyl-2-yl-N~3~-(2,3-dihydro-1H-inden-1-yl)-4-(phenylsulfonyl)piperazine-1,3-dicarboxamide N~1~-biphenyl-2-yl-N~3~-(3-ethoxypropyl)-4-(phenylsulfonyl)piperazine-1,3-dicarboxamide A further aspect of the present invention is related to the use of the piperazine-2-carboxamide derivatives according to formulae (II) and (III) as a medicament in particular for the preparation of a medicament for the prophylaxis and/or treatment and/or preterm labor, premature birth, for stopping labor prior to cesarean delivery and dysmenorrhea. Also, the compounds of the present invention may used in the treatment of cancer, e.g. colorectal cancer.

Preferably, the compounds according to formula (II) are suitable for the modulation of the prostaglandin receptor, thus specifically allowing the treatment and/or prevention of disorders mediated by the prostaglandin receptor. Said treatment involves the modulation—notably the down regulation or the antagonisation—of the prostaglandin receptor.

Still a further object of the present invention is a process for preparing piperazine-2-carboxamide derivatives according to formula (I).

The herein exemplified piperazine-2-carboxamide derivatives may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

Generally, the piperazine-2-carboxamide derivatives according to the general formula (I) could be obtained by several synthetic approaches, using both solution-phase and solid-phase chemistry protocols.

According to one process, piperazines of general formula (Ia)—whereby the substituents $R^1$, $R^2$, X, A and B are defined as above and Y is $SO_2$ or CO— may be prepared from 2-carboxypiperazine using solution-phase chemistry protocols such as described in the below Examples and illustrated by Scheme 1, below. 2-carboxypiperazine (which is a commercial compound) is first reacted with sulfonyl chlorides or acid chlorides (IV) using well known standard solution phase chemistry protocols such as e.g. Schotten-Bauman conditions affording intermediates of general formula (V). The latter is subsequently reacted with sulfonyl chlorides or acid chlorides (VI) under similar conditions, affording carboxylic acids of general formula (VII) whereby Y, A, X and B are defined as for compounds of general formula (I). Finally, intermediates (VII) may be reacted with amines (VIII) whereby $R^1$ and $R^2$ are defined as above, using standard amide coupling conditions well known to the practitioner skilled in the art (EDC/HOBt or TBTU/base as for example) to yield product of general formula (I).

Scheme 1

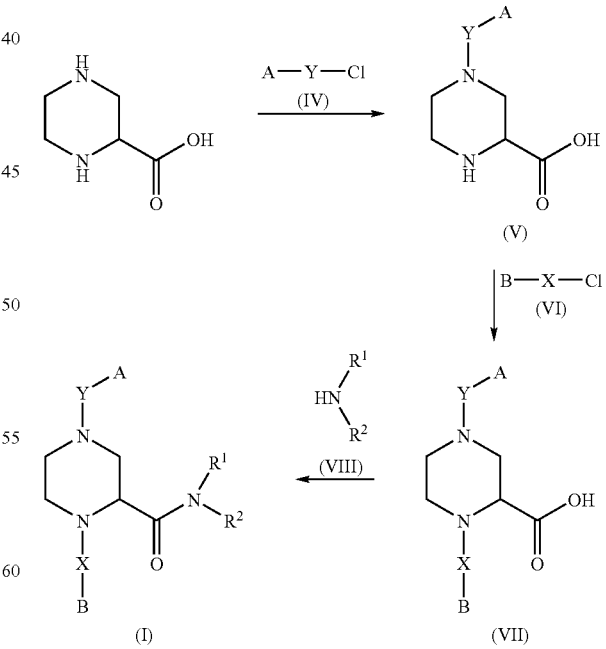

According to a further approach, compounds of general formula (I)—whereby the substituents A, B, X, $R^1$ and $R^2$ are as above defined and Y is CO, $SO_2$ or $CONR^3$—may be obtained from protected 2-carboxypiperazines of general formula (IX) whereby $P_1$ and $P_2$ are suitable N-protective groups, preferably, but not limited to, Boc for $P_1$ and Fmoc for $P_2$ as outlined in scheme 2. Such derivatives may be obtained from commercial sources or prepared using standard conditions as described in Tetrahedron Letters, 30 (39), p. 5193-96 (1989) for example. They are first reacted with amines (VIII) whereby $R^1$ and $R^2$ are as above defined using conditions and methods well known to those skilled in the art to prepare an amide from an amine and a carboxylic acid or a carboxylic acid derivatives, using standard peptide coupling agents such as EDC, HATU, DIC, TBTU or others, to yield compounds of general formula (X) whereby $P_1$, $P_2$, $R^1$ and $R^2$ are as above defined. From intermediate compound (X), the functionalisation of either of the piperazine nitrogens may be performed by selective deprotection of the corresponding N-protective group (e.g. TFA where $P_1$ is Boc or piperidine when $P_2$ is Fmoc), followed by reaction with the reagent of formula B—X-LG (XVII) or A-Y-LG (XVIII), with A, B and X being as above defined and Y is CO or $SO_2$ while LG is any appropriate leaving group. The leaving group LG is in a preferred embodiment a chlorine atom. The reagents B—X—Cl or A-Y—Cl are preferably used in conjunction with a tertiary amine, but where moieties X or Y are a carbonyl (CO), the leaving group LG may also be an hydroxy group. In such case the moieties B—COOH or A-COOH are preferably used in conjunction with a peptide coupling agent, e.g. from the above mentioned groups. In the case where the moiety Y is an amide $CONR^3$—with $R^3$ being as above defined—the functionalisation of the piperazine nitrogen is performed by reaction with the appropriate isocyanate of the formula A-N=C=O (XIX). Thereby, A is as above defined. Alternatively, the functionalisation of the piperazine nitrogen may be performed using the an amine of general formula $ANHR^3$ (XX)—with $R^3$ being as above defined—in conjunction with $LG_1COLG_2$ (XXI) whereby $LG_1$ and $LG_2$ are suitable leaving groups (e.g. phosgene or triphosgene). Intermediates (XII) and (XV) obtained by said deprotection/fonctionalisation steps are then subjected to a second deprotection/fonctionalisation step using similar conditions and appropriate reagents to yield product of general formula (I) whereby A, B, X, Y, $R^1$ and $R^2$ are as above defined.

Scheme 2

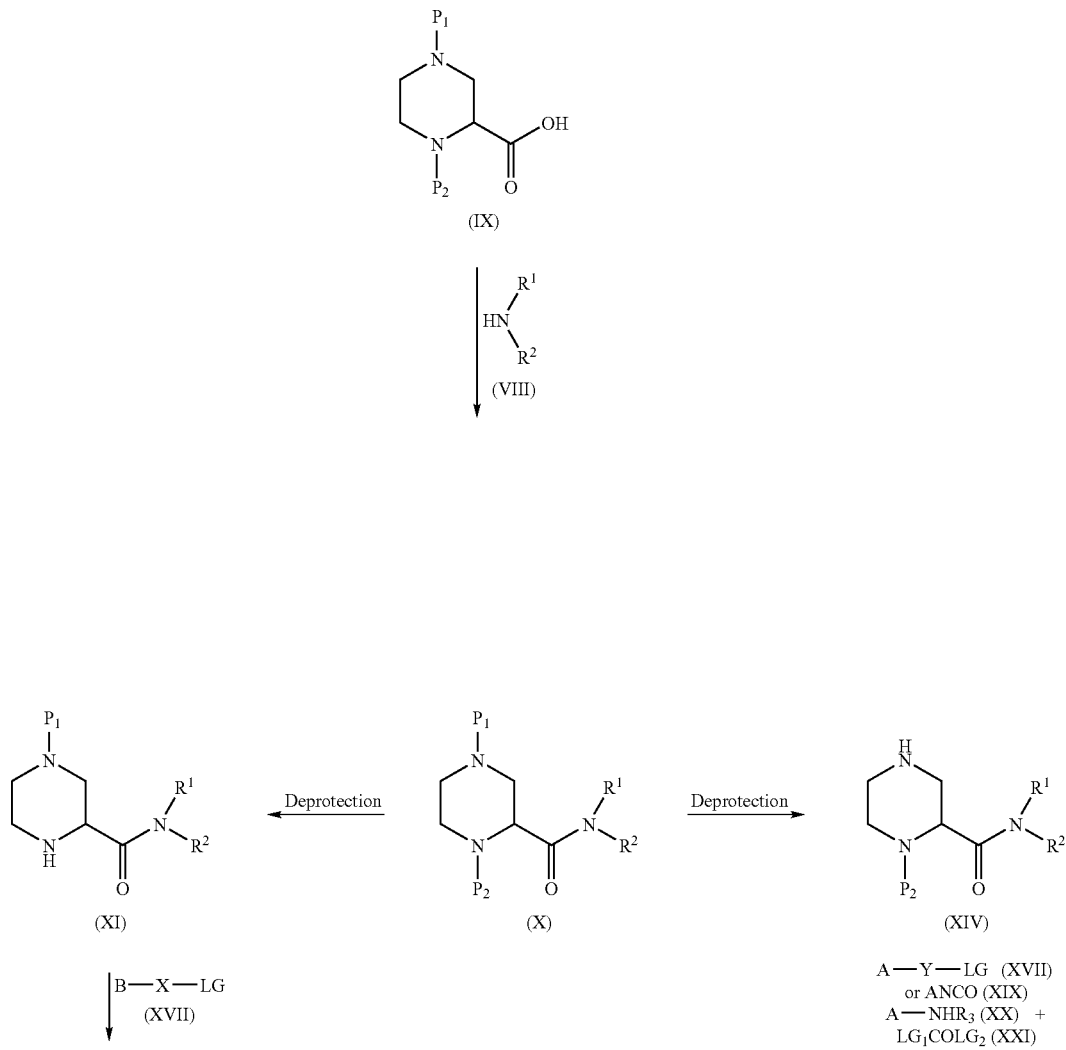

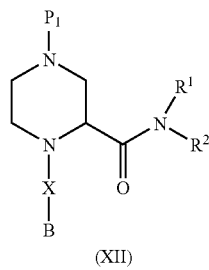

(XII)

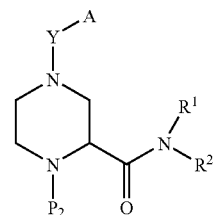

(XV)

|Deprotection

|Deprotection

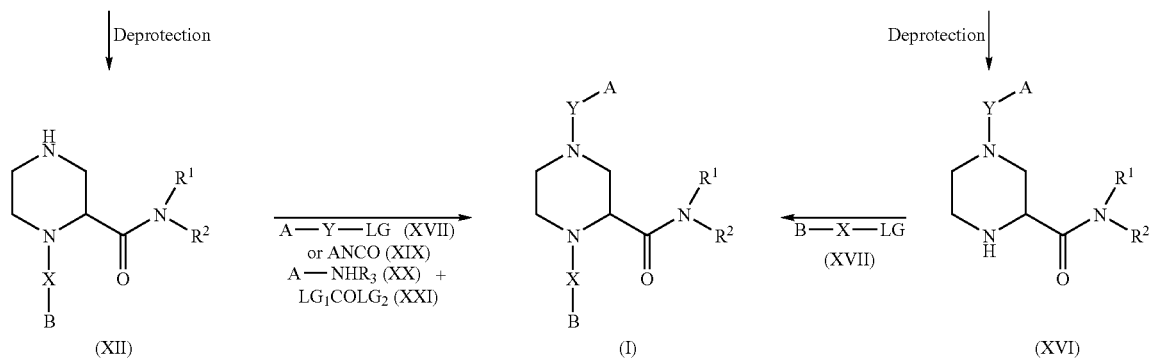

(XII)　　　　　　　　　(I)　　　　　　　　　(XVI)

According to still a further approach, intermediates of general formula (XII), whereby $P_1$, X, B, $R^1$ and $R^2$ are as above defined, may be alternatively obtained from 4-monoprotected 2-carboxypiperazines of general formula (XXII) as outlined in Scheme 3 below. Such piperazines may be obtained from commercial sources or are prepared using well known process as described in J. Med. Chem, 43(3), p. 369 (2000) for example. Reaction of (XXII) with the appropriate reagent B—X—Cl whereby B and X are as above defined using well known standard solution phase chemistry protocols such as e.g. Schotten-Bauman conditions or those described in Tetrahedron Letters, 39, p. 1295-98 (1998) for example affords intermediates of general formula (XXIII). The latter may be reacted then with amines of general formula $NHR^1R^2$ (VIII) whereby $R^1$ and $R^2$ are as above defined using standard peptide coupling agent as described above to yield intermediates of general formula (XII) whereby $P_1$, X, B, $R^1$ and $R^2$ are as above defined.

Scheme 3

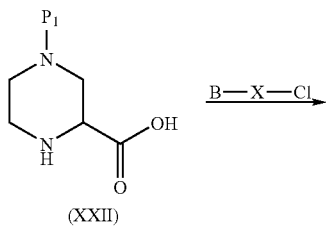

(XXII)

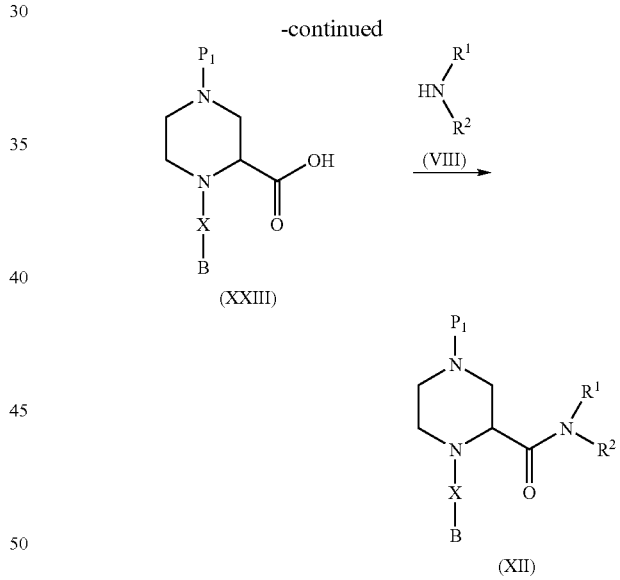

(XXIII)

(XII)

Similarly intermediates of general formula (XV) whereby A, Y, $P_2$, $R^1$ and $R^2$ are as above defined may be obtained from intermediates of general formula (V) whereby A, Y, $P_2$, $R^1$ and $R^2$ are as above defined in a two steps process as outlined in scheme 4 below. The free amino function in intermediate (V) may be first protected with any appropriated N-protective group using standard conditions well known from those skilled in the art to give intermediate of general formula (XXIV) whereby A and Y are as above defined and $P_2$ is any appropriate N-protective group, preferably a Boc. A standard coupling step of the carboxylic acid derivative (XXIV) with an amine of general formula $HNR^1R^2$ (VIII) whereby $R^1$ and $R^2$ are as above defined under conditions described above yields to intermediates of general formula (XV) whereby A, Y, $P_2$, $R^1$ and $R^2$ are as above defined.

Scheme 4

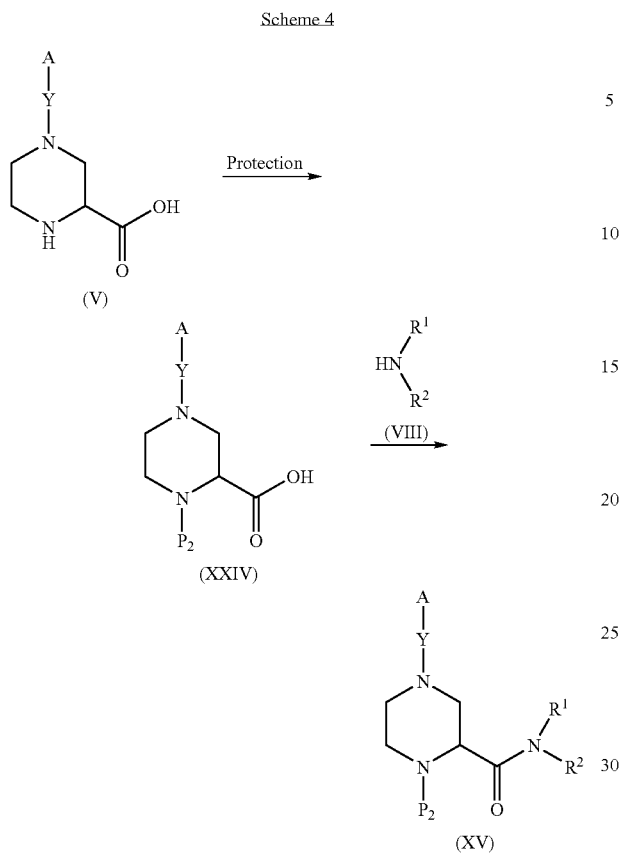

Scheme 5

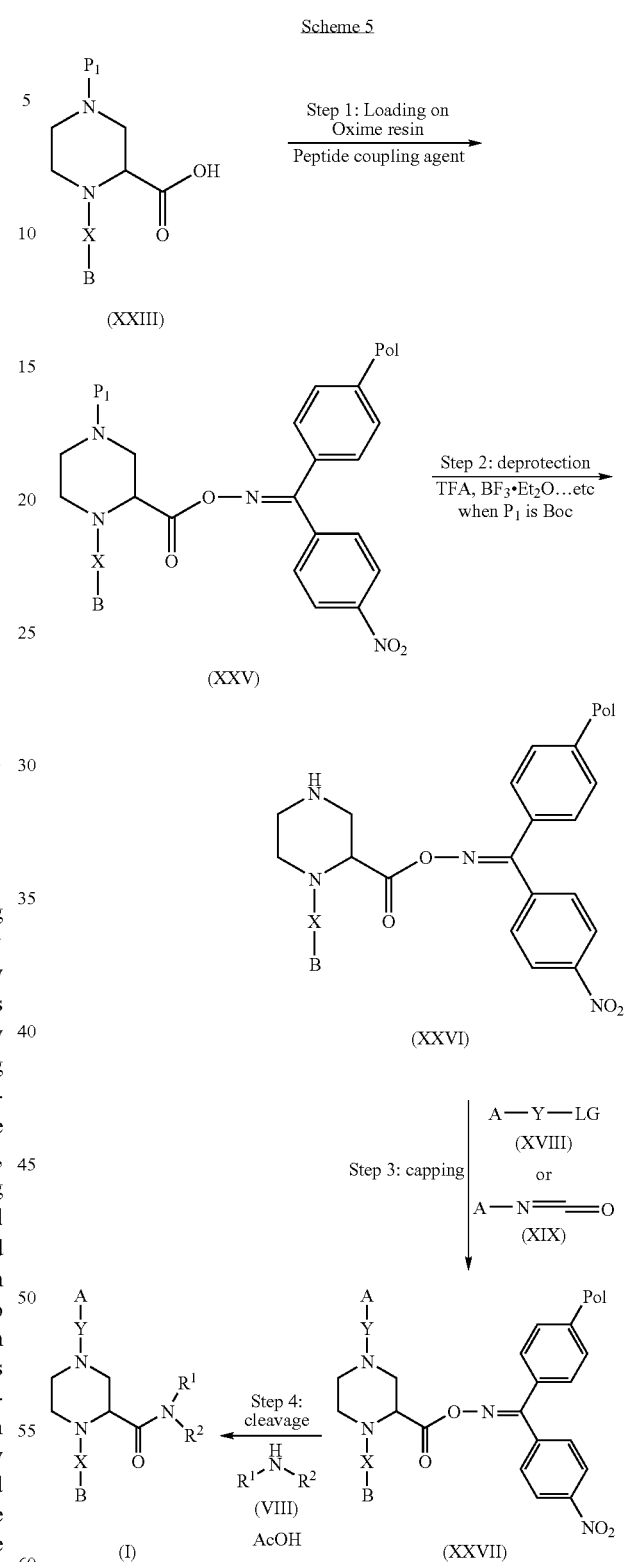

According to yet another approach, derivatives according to the general formula I, whereby the substituents A, B, X, $R^1$ and $R^2$ are as above defined and Y is CO, $SO_2$ or $CONR^3$, may be prepared using solid phase protocols. Said approach is illustrated by the below Schemes 5 and 6 wherein the moiety "Pol" symbolizes the resin beads to which the corresponding compounds are linked during the solid phase synthesis. Carboxypiperazine intermediate (XXIII) whereby B and X are defined as above and $P_1$ is any suitable protective group, preferably a Boc, is reacted e.g. with Kaiser oxime resin using standard carbodiimide-mediated coupling conditions well known to the practitioner skilled in the art (step 1), followed by N-deprotection with dilute TFA in DCM, or with $BF_3.OEt_2$ in dilute HOAc in DCM when $P_1$ is Boc (step 2), to give compound (XXVI). The latter compound can be then treated with the suitable agent A-Y-LG (XVIII) whereby A is as above defined and Y is CO or $SO_2$ while LG is any appropriate leaving group (step 3). LG is preferably a chlorine atom and in that case A-Y—Cl is used in conjunction with a tertiary amine, but where Y is CO, LG may be an hydroxy group and in that case A-COOH is used in conjunction with a peptide coupling agent, e.g. from the above mentioned groups. In the case where Y is $CONR^3$ whereby $R^3$ is as above defined intermediate (XXVI) is reacted with the corresponding isocyanate A-N=C=O (XIX) whereby A is as above defined. In order to obtain the final compounds of general formula I, the linkage to the resin is cleaved by prolonged treatment with amines of general formulae (VIII) and low percentages of a weak acid, such as HOAc (step 4).

According to yet another process, compounds of general formula (I) whereby A, B, X, Y, $R^1$ and $R^2$ are as above defined may be obtained from intermediates of general formula (XXV) whereby A and Y are as above defined and $P_2$ is any appropriate N-protective group, preferably a Boc following a similar solid-phase process as outlined in scheme 6 below. Intermediate (XXIV) is first loaded on Kaiser oxime resin (step 1) and the $P_2$ protective group is removed (step 2) using conditions described above. The so-called capping step (step 3) is performed in this case by reaction of the deprotected resin (XXIX) with B—X-LG whereby B and X are as above defined and LG is any appropriate leaving group. LG is preferably a chlorine atom and in that case B—X—Cl is used in conjunction with a tertiary amine, but when X is CO, LG may be an hydroxy group and in that case B—COOH is used in conjunction with a peptide coupling agent, e.g. from the above mentioned groups. The final compounds of general formula (I) are obtained by cleavage of the resin linkage with amines of general formula (VIII) as previously described (step 4).

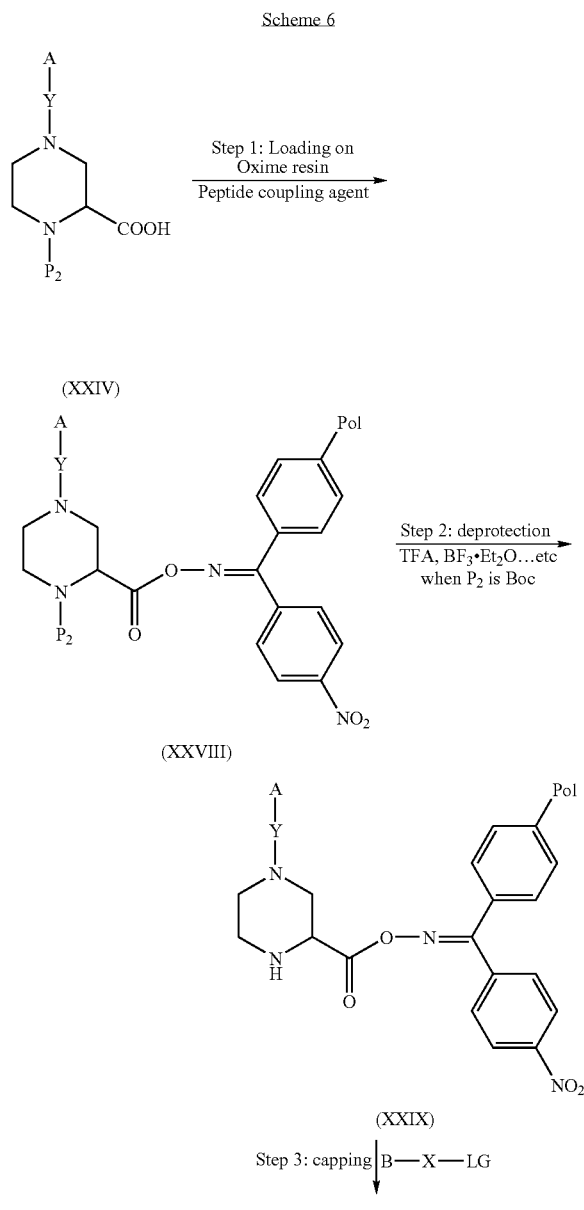

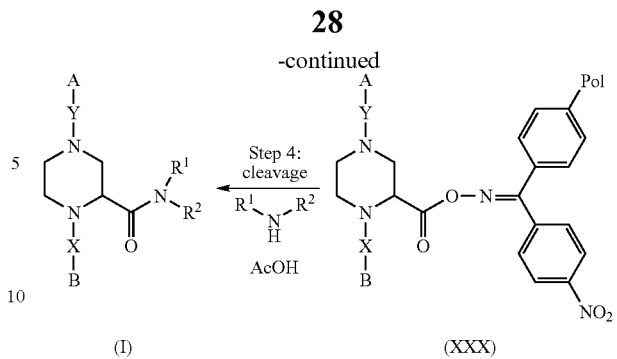

Other derivatives of formula I may be prepared using known modifications to, or variations of, the Schemes 5 and 6 reaction sequence. Further to the above mentioned Kaiser oxime resin, other suitable reagents, notably resins, known to a person skilled in the art, could be employed for the solid-phase synthesis of compounds of general formula I.

Chiral compounds may be obtained following any of the above described methods starting from corresponding enantiomerically pure or enriched starting materials.

If the above set out general synthetic methods are not applicable to obtaining compounds according to formula (I) and/or to necessary intermediates for the synthesis of compounds of formula (I), suitable methods of preparation known by a person skilled on the art should be used. In general, the synthesis pathways for any individual compound of formula (I) will depend on the specific substitutents of each molecule and upon the ready availability of intermediates necessary; again such factors being appreciated by those of ordinary skill in the art. For all the protection and deprotection methods, see Philip J. Kocienski, in "*Protecting Groups*", Georg Thieme Verlag Stuttgart, New York 1994 and, Theodora W. Greene and Peter G. M. Wuts in "*Protective Groups in Organic Synthesis*", Wiley-Interscience, 1991.

A final aspect of the present invention consists in the intermediate compounds of formulae (VII), (XVI) and (XIII) selected from the group consisting of:

4-(tert-butoxycarbonyl)-1-(benzenesulfonyl)piperazine-2-carboxylic acid 4-(tert-butoxycarbonyl)-1-(quinolin-8-ylsulfonyl)piperazine-2-carboxylic acid (2R)-4-(tert-butoxycarbonyl)-1-(quinolin-8-ylsulfonyl)-piperazine-2-carboxylic hydrochloride 4-(tert-butoxycarbonyl)-1-(biphenyl-4-sulfonyl)piperazine-2-carboxylic acid 4-(tert-butoxycarbonyl)-1-(thien-2-ylsulfonyl)piperazine-2-carboxylic acid 4-(tert-butoxycarbonyl)-1-benzoylpiperazine-2-carboxylic acid 4-(tert-butoxycarbonyl)-1-(3-chloro-benzoyl)piperazine-2-carboxylic acid 1-(tert-butoxycarbonyl)-4-(4-tert-butylphenylsulfonyl)piperazine-2-carboxylic acid (2R)-4-(quinolin-8-ylsulfonyl)piperazine-2-carboxylic acid (2S)-4-[(4-tert-butylphenyl)sulfonyl]-1-(quinolin-8-ylsulfonyl)piperazine-2-carboxylic acid (2R)-4-[(4-tert-butylphenyl)sulfonyl]-1-(quinolin-8-ylsulfonyl)piperazine-2-carboxylic acid (2R)-1-[(4-tert-butylphenyl)sulfonyl]-4-(quinolin-8-ylsulfonyl)piperazine-2-carboxylic acid tert-butyl (3R)-3-[(prop-2-enylamino)carbonyl]-4-(quinolin-8-ylsulfonyl)piperazine-1-carboxylate (2R)—N-prop-2-enyl-1-(quinolin-8-ylsulfonyl)piperazine-2-carboxamide hydrochloride 4-tert-butyl 1-(9H-fluoren-9-ylmethyl) 2-({[(1-ethylpyrrolidin-2-yl)methyl]amino}-carbonyl)piperazine-1,4-dicarboxylate N~3~-[(1-ethylpyrrolidin-2-yl)methyl]-N~1~-(4-phenoxyphenyl)-piperazine-1,3-dicarboxamide When employed as pharmaceuticals, piperazine-2-carboxamide derivatives of the present invention are typically administered in the form of a pharmaceutical composition. Hence, pharmaceutical compositions comprising a compound of formulae (I), (II) or (III) and a pharmaceutically acceptable carrier, diluent or excipient are also within the scope of the present invention. A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing piperazine-2-carboxamide derivatives of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, transdermal, subcutaneous, intravenous, intramuscular, and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the piperazine-2-carboxamide derivative is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the piperazine-2-carboxamide derivatives of formulae (I), (II) or (III) in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 5 of *Remington's Pharmaceutical Sciences*, 20<sup>th</sup> Edition, 2000, Marck Publishing Company, Easton, Pa. which is incorporated herein by reference.

The compounds of this invention can also be administered in sustained release forms or from sustained release drug delivery systems. A description of representative sustained release materials can also be found in the incorporated materials in *Remington's Pharmaceutical Sciences*.

In the following the present invention shall be illustrated by means of some examples which are not construed to be viewed as limiting the scope of the invention. The following abbreviations are hereinafter used in the accompanying examples: min (minute), hr (hour), g (gram), mmol (millimole), m.p. (melting point), eq (equivalents), ml (milliliter), μl (microliters), ACN (acetonitrile), Boc (tert-butoxycarbonyl), cHex (cyclohexanes), CSA (camphorsulphonic acid), DCM (dichloromethane), DIC (diisopropyl carbodiimide), DIEA (diisopropyl ethylamine), DMAP (4-dimethylaminopyridine), DMF (dimethylformamide), DMSO (dimethylsulfoxide), DMSO-d$_6$ (deuterated dimethylsulfoxide), EDC (1-(3-dimethylaminopropyl)-3-ethylcarbodiimide hydrochloride), EtOAc (ethyl acetate), Et$_2$O (diethyl ether), Fmoc (9-fluorenylmethoxycarbonyl), HATU (O-(7-azabenzotriazol-1-yl-N,N,',N'-tetramethyluroniumhexafluorophosphonate), HOBt (1-hydroxybenzotriazole), MeOH (methanol), MsCl (methylsulfonyl chloride), nBuLi (n-butyllithium), NMM (N-methyl morpholine), PE (petroleum ether), rt (room temperature), TBME (tert-butyl methyl ether), TBTU (O-benzotriazolyl-N,N,N',N'-tetramethyluronium-tetrafluoroborate), TEA (triethyl amine), TFA (trifluoroacetic acid), THF (tetrahydrofuran), tlc (thin layer chromatography), TosCl (toluenesulfonyl chloride).

Intermediate 1: 4-(tert-butoxycarbonyl)-1-(benzenesulfonyl)piperazine-2-carboxylic acid (Scheme 3, compound XXIII)

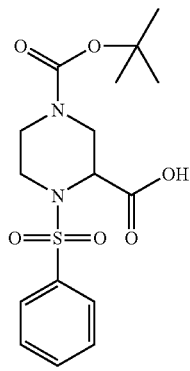 [SMILES: CC(C)(C)OC(=O)N1CCN(S(=O)(=O)c2ccccc2)C(C(=O)O)C1]

To a suspension of 2-carboxypiperazine dihydrochloride (3 g, 14.77 mmol) in dioxane/water, 2:1, 45 ml) was slowly added a solution of NaOH (1.18 g, 29.54 mmol in 1.2 ml of water) followed by di-tert-butyl-di-carbonate (3.54 g, 16.25 mmol). The reaction was stirred at room temperature for 5 h then triethylamine (4.11 ml, 19.54 mmol), DMAP (0.18 g, 1.48 mmol) and phenylsulfonylchloride (2.6 g, 14.77 mmol), were successively added. The reaction was stirred overnight at room temperature. The solvents were removed in vacuo, EtOAc (10 ml) was added and organic phase washed with HCl 1M. The aqueous layer was extracted with EtOAc and the combined organic phases were washed with brine, dried over magnesium sulfate, filtered and concentrated to afford the desired sulfonamide which was used without further purification.

$^1$H NMR (CDCl$_3$): 1.40 (s, 9H, Boc); 2.75-2.86 (m, 1H); 3.01-3.09 (m, 1H); 3.29-3.39 (m, 1H); 3.59-3.63 (m, 1H); 3.96-4.09 (m, 1H); 4.48-4.68 (m, 2H); 7.43-7.48 (m, 2H); 7.52-7.56 (m, 1H); 7.73-7.76 (m, 2H).

Intermediate 2: 4-tert-butoxycarbonyl)-1-(quinolin-8-ylsulfonyl)piperazine-2-carboxylic acid (Scheme 3, compound XXIII)

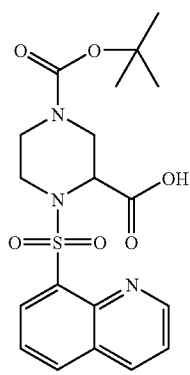 [SMILES: CC(C)(C)OC(=O)N1CCN(S(=O)(=O)c2cccc3cccnc23)C(C(=O)O)C1]

Intermediate 2 was obtained following the procedure described for intermediate 1 from 2-carboxypiperazine dihydrochloride and quinolin-8-ylsulfonylchloride.

$^1$H NMR (CDCl$_3$): 1.45 (s, 9H, Boc); 2.83-2.98 (m, 1H); 3.12-3.20 (m, 2H); 3.55-3.69 (m, 1H); 3.92-4.08 (m, 1H); 4.69-4.80 (m, 1H); 5.23-5.32 (m, 1H); 7.59-7.75 (m, 2H); 8.10-8.19 (m, 1H); 8.29-8.39 (m, 1H); 8.56-8.62 (m, 1H); 8.99-9.03 (m, 1H).

Intermediate 3: (2R)-4-(tert-butoxycarbonyl)-1-quinolin-8-ylsulfonyl)-piperazine-2-carboxylic hydrochloride (Scheme 3, compound XXIII)

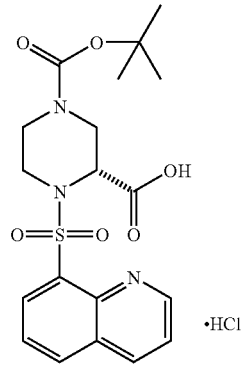 [SMILES: CC(C)(C)OC(=O)N1CCN(S(=O)(=O)c2cccc3cccnc23)[C@@H](C(=O)O)C1 ; Cl]

(2R)-piperazine-2-carboxylic acid.2CSA (9.492 g, 15.96 mmol) was dissolved in dioxane/water 1:1 (60 ml) and concentrated sodium hydroxide was added until the pH reached 9-10. Di-tert-butyl-dicarbonate (3.755 g, 17.55 mmol) was then added and the mixture was stirred 6 h at room temperature. A white precipitate appeared, the pH dropped to 7 and was brought back to 9 by the addition of concentrated NaOH. 8-quinoline sulfonylchloride (3.63 g, 15.64 mmol) and triethylamine (4.33 ml, 31.28 mmol) were slowly added and the mixture was stirred overnight at room temperature. The solution was made acidic by the addition of HCl 1N and the white precipitate thus obtained was filtered and dried to give the desired compound.

Yield: 93% (6.3 g), LC/MS: ESI (+): 422 (M+1); ESI (−): 420 (M−1); HPLC purity: 91.7%

$^1$H NMR (CDCl$_3$): 1.43 (s, 9H), 3.01 (m, 1H), 3.13 (m, 2H), 3.45 (m, 1H), 3.94 (m, 1H), 4.75 (d, J=13.5 Hz, 1H), 5.24 (s, 1H), 7.63 (dd, J=4.5 and 8.3 Hz, 1H), 7.70 (t, J=7.91 Hz, 1H), 8.14 (d, J=7.5 Hz, 1H), 8.36 (d, J=7.5 Hz, 1H, 8.61 (d, J=7.5 Hz, 1H), 9.01 (dd, J=1.7 and 4.3 Hz, 1H).

Intermediate 4: 4-(tert-butoxycarbonyl)-1-(biphenyl-4-sulfonyl)piperazine-2-carboxylic acid (Scheme 3, compound XXIII)

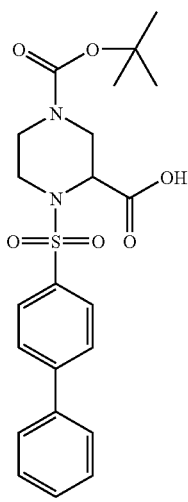 [SMILES: CC(C)(C)OC(=O)N1CCN(S(=O)(=O)c2ccc(-c3ccccc3)cc2)C(C(=O)O)C1]

Intermediate 4 was obtained following the procedure described for intermediate 1 from 2-carboxypiperazine dihydrochloride and biphenyl-4-sulfonylchloride.

$^1$H NMR (CDCl$_3$): 1.38 (s, 9H, Boc); 2.77-2.94 (m, 1H); 3.02-3.15 (m, 1H); 3.29-3.41 (m, 1H); 3.60-3.69 (m, 1H); 3.95-4.10 (m, 1H); 4.48-4.55 (m, 1H); 4.59-4.64 (m, 1H); 7.37-7.51 (m, 3H); 7.59-7.63 (m, 2H); 7.69-7.72 (m, 2H); 7.79-7.83 (m, 2H).

Intermediate 5: 4-(tert-butoxycarbonyl)-1-(thien-2-ylsulfonyl)piperazine-2-carboxylic acid (Scheme 3, compound XXIII)

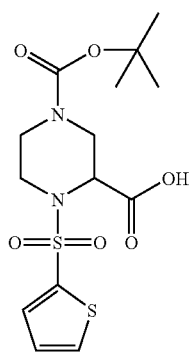 [SMILES: CC(C)(C)OC(=O)N1CCN(S(=O)(=O)c2cccs2)C(C(=O)O)C1]

Intermediate 5 was obtained following the procedure described for intermediate 1 from 2-carboxypiperazine dihydrochloride and thien-2-ylsulfonylchloride.

$^1$H NMR (CDCl$_3$): 1.53 (s, 9H, Boc); 2.94-3.11 (m, 1H); 3.21-3.33 (m, 1H); 3.52-3.68 (m, 1H); 3.79-3.87 (m, 1H); 4.11-4.32 (m, 1H); 4.64-4.72 (m, 1H); 4.74-4.78 (m, 1H); 7.21-7.23 (m, 1H); 7.68-7.70 (m, 1H); 7.74-7.75 (m, 1H).

Intermediate 6: 4-(tert-butoxycarbonyl)-1-benzoylpiperazine-2-carboxylic acid (Scheme 3, compound XXIII)

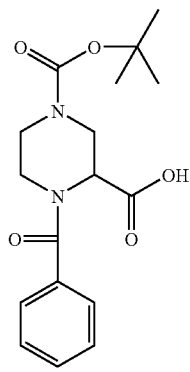 [SMILES: CC(C)(C)OC(=O)N1CCN(C(=O)c2ccccc2)C(C(=O)O)C1]

To a suspension of 2-carboxypiperazine dihydrochloride (3 g, 14.77 mmol) in dioxane/water, 2:1, 45 ml) was slowly added a solution of NaOH (1.18 g, 29.54 mmol in 1.2 ml of water) followed by di-tert-butyl-di-carbonate (3.54 g, 16.25 mmol). The reaction was stirred at room temperature for 5 h then the dioxane was evaporated and sodium hydroxide (1.2 g) in water (30 ml) was added followed by benzoyl chloride (1.86 g, 13.3 mmol) dissolved in DCM (40 ml). The mixture was stirred overnight at room temperature and the organic layer was separated. The aqueous phase was acidified to pH 2 with HCl 1M and extracted twice with EtOAc. Organic phases were combined, washed with brine, dried over magnesium sulfate, filtered and concentrated to afford the desired amidopiperazine which was used without further purification.

$^1$H NMR (CDCl$_3$): 1.47 (s, 9H, Boc); 2.81-2.97 (m, 1H); 3.20-3.28 (m, 1H); 3.48-3.67 (m, 2H); 3.92-4.01 (m, 1H); 4.55-4.76 (m, 2H); 7.42-7.52 (m, 5H).

Intermediate 7: 4-(tert-butoxycarbonyl)-1-(3-chlorobenzoyl)piperazine-2-carboxylic acid (Scheme 3, compound XXIII)

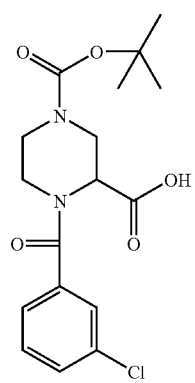 [SMILES: CC(C)(C)OC(=O)N1CCN(C(=O)c2cccc(Cl)c2)C(C(=O)O)C1]

Intermediate 7 was obtained following the procedure described for intermediate 6 from 2-carboxypiperazine dihydrochloride and 3-chlorobenzoylchlorid.

$^1$H NMR (CDCl$_3$): 1.46 (s, 9H, Boc); 2.81-2.95 (m, 1H); 3.12-3.24 (m, 1H); 3.49-3.61 (m, 2H); 3.99-4.09 (m, 1H); 4.51-4.76 (m, 2H); 7.34-7.46-7.72 (m, 4H).

Intermediate 8: 1-(tert-butoxycarbonyl)-4-(4-tert-butylphenylsulfonyl)piperazine-2-carboxylic acid (Scheme 4, compound XXIV)

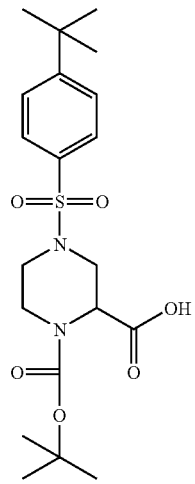 [SMILES: CC(C)(C)OC(=O)N1CCN(S(=O)(=O)c2ccc(C(C)(C)C)cc2)CC1C(=O)O]

To a suspension of piperazine-2-carboxylic acid dihydrochlorid (13.95 g, 68.70 mmol) in water/dioxane 1:1 (280 ml)

at 0° C., NaOH 5 N (48 ml) was added to achieve complete dissolution. 4-tert-butylbenzenesulfonylchloride (17.586 g, 75.57 mmol) in dioxane (140 ml) was then added dropwise at 2° C. In 1 h. The reaction mixture was stirred overnight at 2° C. and over the week-end at room temperature. Solvents were removed in vacuo and the residue obtained was crystallized in EtOH to give 17.3 g of crude 4-(4-tert-butylphenyl-sulfonyl)piperazine-2-carboxylic acid. This material was dissolved in DCM (340 ml) and triethylamine (23 ml, 158 mmol) followed by di-tert-butyl-dicarboxylate (11.5 g, 52.7 mmol) were added. The mixture was stirred at mom temperature overnight, washed with HCl 1N, and brine. Organic phase was then dried over magnesium sulfate, filtered and concentrated to give 23.5 g of a white solid. This crude was purified by flash chromatography using DCM/MeOH 95:5 then DCM/MeOH/AcOH 90:10:0.1.

Yield: 37% (10.86 g), LC/MS: ESI (+): 327 (MH+−100); ESI (−): 425 (M−1)

$^1$H NMR (CDCl$_3$): 1.33 (s, 18H), 2.03 (m, 1H), 2.21 (d, J=10.5 Hz, 1), 3.09-3.25 (m, 1H), 3.48 (m, 1H), 3.73 (d, J=14.1 Hz, 1H), 4.09 (d, J=10.4 Hz, 1H), 4.37 (m, 1H), 7.62 (m, 4H).

Intermediate 9: (2R)-4-(quinolin-8-ylsulfonyl)piperazine-2-carboxylic acid (Scheme 1, compound V)

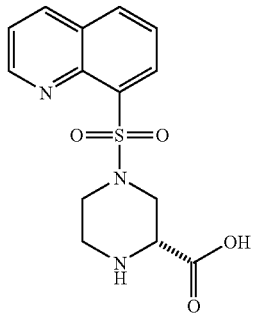 [SMILES: O=C(O)[C@H]1CN(S(=O)(=O)c2cccc3cccnc23)CCN1]

(2R)-piperazine-2-carboxylic acid.2CSA (3.717 g, 6.25 mmol) was dissolved in dioxane/water 1:1 (60 ml) and potassium carbonate (3.455 g, 25 mmol) was added. The pH was controlled (9-10) before the slow addition of a solution of 8-quinoline sulfonylchloride (1.707 g, 7.50 mmol) in dioxane (10 ml). The reaction mixture was then stirred overnight at room temperature and acidified to pH=1 with HCl 1 N. It was then washed twice with EtOAc, basified again and extracted with EtOAC. The organic phase was dried over magnesium sulfate, filtered and concentrated to give 437 mg of the disulfonylated side-product. Finally, the aqueous phase was lyophilised, treated with ACN/MeOH 3:1, filtrated and concentrated to give 4.69 g of a white solid which was used without further purification.

LC/MS: ESI (+): 322 (M+1); ESI (−): 422 (M−1)

Intermediate 10: (2S)-4-[4-tert-butylphenyl)sulfonyl]-1-quinolin-8-ylsulfonyl)piperazine-2-carboxylic acid (Scheme 1, compound VII)

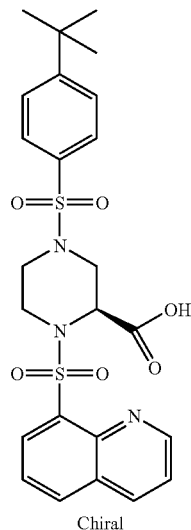 [SMILES: CC(C)(C)c1ccc(S(=O)(=O)N2CCN(S(=O)(=O)c3cccc4cccnc34)[C@H](C(=O)O)C2)cc1]

(2S)-piperazine-2-carboxylic acid.2CSA (4 g, 6.73 mmol) was dissolved in 60 ml of dioxane and 72 ml of Na$_2$CO$_3$ 1M. A solution of (4-tert-butylphenyl)sulfonyl chloride (1.65 g, 1.05 eq) in 12 mL dioxane was then slowly added over 30 mn at 0° C. and the mixture was stirred at room temperature overnight. It was acidified to pH 1 with 17 ml of HCl 6M and washed 5 times with 100 ml EtOAc/Hexane (1/1). The aqueous phase was then diluted with 27 ml dioxane and the pH adjusted to 11 with 9.5 ml of NaOH (10%) until the solution became clear. A further 50 ml of EtOAc/Hexane organic were removed. The solution was cooled to 0° C. and the solution was acidified to pH 6 with a few drops of HCl (6M). The precipitate was filtered, washed twice with water (10 ml) and dried to afford 1.6 g of (2S)-4-[(4-tert-butylphenyl)sulfonylpiperazine-2-carboxylic acid. The acid was directly engaged to the next step and dissolved in 90 ml of dioxane and 105 ml of Na$_2$CO$_3$ (1M). A solution quinolin-8-ylsulfonyl chloride (1.65 g, 1.05 eq) in 12 ml dioxane was then slowly added over 30 mn at 0° C. and the mixture was stirred at room temperature overnight. The solution was diluted with water (93 ml), acidified to pH 4.5 with of HCl 2M (82 ml) and stirred at room temperature for 1 h. The precipitate was filtered, washed twice with water (10 ml) and dried to afford the desired sulphonamide, (2S)-4-[(4-tert-butylphenyl)sulfonyl]-1-(quinolin-8-ylsulfonyl)piperazine-2-carboxylic acid.

Yield: 55% (1.92 g), MS: ESI (+): 518 (M+1); ESI (−): 516 (M−1)

$^1$H NMR (CDCl$_3$): 1.28 (s, 9H), 1.6 (m, 1), 2.2 (m, 1H), 3.54 (m, 2H), 3.8 (d, 1H), 4.08 (d, 1H), 5.1 (s, 1H), 7.5-7.7 (m, 6H), 8.2 (d, 1H), 8.3 (d, 1H), 8.4 (d, 1H), 8.82 (s, 1H).

HPLC purity: 96.5% ee>99.8% (Chirobotie V 250 mm×4.6, 5 microM/MeOH/0.1% TEA.AcOH)

Intermediate 11: (2R)-4-[(4-tert-butylphenyl)sulfonyl]-1-(quinolin-8-ylsulfonyl)-piperazine-2-carboxylic acid (Scheme 1, compound VII)

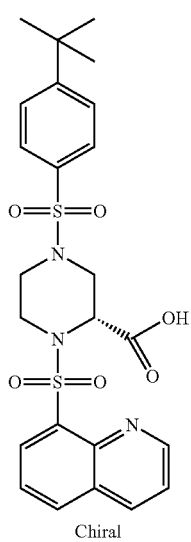 [SMILES: CC(C)(C)c1ccc(S(=O)(=O)N2CCN(S(=O)(=O)c3cccc4cccnc34)[C@@H](C(=O)O)C2)cc1]

Chiral

Intermediate 11 was obtained following the protocol described for example 10 starting from (2R)-piperazine-2-carboxylic acid.2CSA.

$^1$H NMR (CDCl$_3$): 1.28 (s, 9H), 1.6 (m, 1H), 2.2 (m, 1H), 3.54 (m, 2H), 3.8 (d, 1H), 4.08 (d, 1H), 5.1 (s, 1H), 7.5-7.7 (m, 6H), 8.2 (d, 1H), 8.3 (d, 1H), 8.4 (d, 1H), 8.82 (s, 1H).

MS: ESI (+): 518 (M+1); ESI (−): 516 (M−1); HPLC purity: 97.6% ee=50% (Chirobotic V 250 mm×4.6, 5 microM/MeOH/0.1% TEA.AcOH)

Intermediate 12: (2R)-1-[(4-tert-butylphenyl)sulfonyl]-4-(quinolin-8-ylsulfonyl)piperazine-2-carboxylic acid (Scheme 1, compound VII)

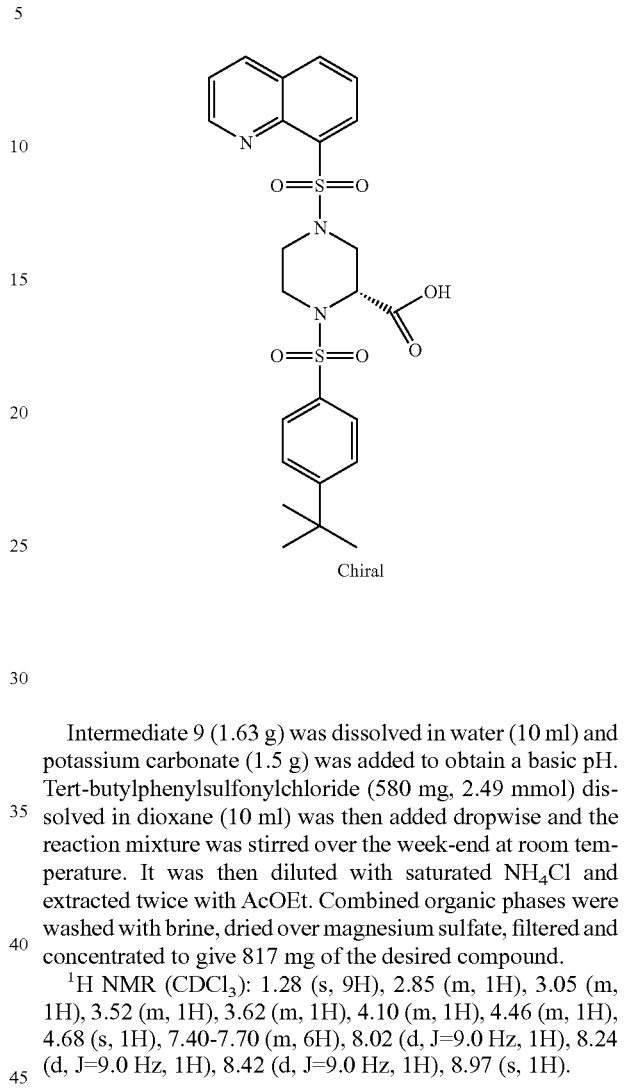

Chiral

Intermediate 9 (1.63 g) was dissolved in water (10 ml) and potassium carbonate (1.5 g) was added to obtain a basic pH. Tert-butylphenylsulfonylchloride (580 mg, 2.49 mmol) dissolved in dioxane (10 ml) was then added dropwise and the reaction mixture was stirred over the week-end at room temperature. It was then diluted with saturated NH$_4$Cl and extracted twice with AcOEt. Combined organic phases were washed with brine, dried over magnesium sulfate, filtered and concentrated to give 817 mg of the desired compound.

$^1$H NMR (CDCl$_3$): 1.28 (s, 9H), 2.85 (m, 1H), 3.05 (m, 1H), 3.52 (m, 1H), 3.62 (m, 1H), 4.10 (m, 1H), 4.46 (m, 1H), 4.68 (s, 1H), 7.40-7.70 (m, 6H), 8.02 (d, J=9.0 Hz, 1H), 8.24 (d, J=9.0 Hz, 1H), 8.42 (d, J=9.0 Hz, 1H), 8.97 (s, 1H).

Intermediate 13: tert-butyl (3R)-3-[(prop-2-enylamino)carbonyl]-4-(quinolin-8-ylsulfonyl)piperazine-1-carboxylate (Scheme 3, compound XII)

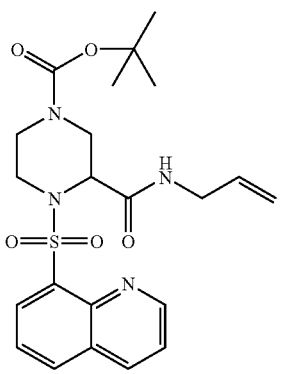 [SMILES: C=CCNC(=O)C1CN(C(=O)OC(C)(C)C)CCN1S(=O)(=O)c1cccc2cccnc12]

Intermediate 3, (2R)-4-(tert-butoxycarbonyl)-1-(quinolin-8-ylsulfonyl)piperazine-2-carboxylic hydrochloride (2.22 g, 5.28 mmol) was dissolved in DMF (60 ml) and stirred 15 mn at room temperature in presence of HOBt (856 mg, 6.33 mmol), EDC (1.214 mg, 6.33 mmol), and DIEA (2 ml, 13.2 mmol). Allylamine (436 □l, 5.80 mmol) was then added and the mixture was stirred at room temperature for 2 h. DMF was removed under reduced pressure and AcOEt was added to the oil thus obtained. The solution was washed with saturated NH₄Cl, saturated NaHCO₃ and with brine (twice). It was dried over magnesium sulfate, filtered and concentrated to give 1.9 g of crude material. Purification was performed by flash chromatography with cHex/AcOEt 50:50.

Yield: 79% (1.53 g of a nice white foam); MS: ESI (+): 460 (M+1)

¹H NMR (MeOD): 1.38 (s, 9H), 2.72 (m, 1H), 3.02 (d, J=12.8 Hz, 1H), 3.63 (m, 1H), 3.73 (s, 2), 3.81 (m, 2H), 4.45 (d, J=13.2 Hz, 1H), 5.06 (m, 3H), 5.74 (m, 1H), 7.68 (m, 2H), 8.23 (d, J=6.8 Hz, 1H), 8.45 (m, 2H), 9.03 (s, 1H).

HPLC purity: 98.8%

Intermediate 14: (2R)—N-prop-2-enyl-1-(quinolin-8-ylsulfonyl)piperazine-2-carboxamide hydrochloride (Scheme 2, compound XIII)

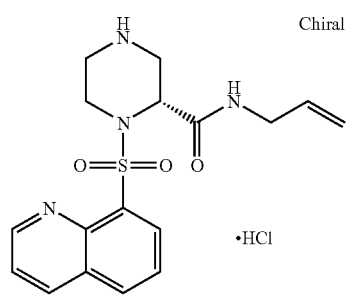 [SMILES: C=CCNC(=O)[C@H]1CNCCN1S(=O)(=O)c1cccc2cccnc12 ; Cl]

A solution of intermediate 13 (1.455 g, 3.16 mmol) in DCM (60 ml) was cooled to 0° C. under inert atmosphere. HCl (20 ml of a 4M solution in dioxane) was slowly added and the mixture was stirred at 0° C. for 3 h. To complete the reaction another 20 ml of HCl (solution 4M in dioxane) was added and the mixture was stirred at room temperature for 1 h. It was then concentrated under reduced pressure and the oil thus obtained was triturated in Et₂O to give a very hygroscopic white solid.

Yield: 75%; LC/MS: ESI (+): 361 (M+1); HPLC purity: 98.8%

¹H NMR (DMSO): 2.61 (m, 1H), 2.88 (m, 1H), 3.14 (d, J=12.1 Hz, 1H), 3.34-3.71 (m, 4H), 4.03 (d, J=13.6 Hz, 1H), 5.01-5.15 (m, 3H), 5.69 (m, 1H), 7.75 (m, 2H), 8.28 (t, J=5.5 Hz, 1H), 8.36 (d, J=8.3 Hz, 1H), 8.42 (d, J=6.4 Hz, 1H), 8.59 (m, 1H), 9.06 (m, 1H), 9.59 (m, 1H).

Intermediate 15: 4-tert-butyl 1-(9H-fluoren-9-ylmethyl) 2-({[(1-ethylpyrrolidin-2-yl)methyl]amino}carbonyl)piperazine-1,4-dicarboxylate (Scheme 2, compound X)

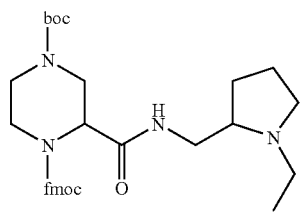

2-(R,S)-4-(tert-butoxycarbonyl)-1-(9H-fluoren-9-ylmethyl)piperazine-2-carboxylic acid (2 g, 4.42 mmol), (R,S)-2-aminomethyl)-1-ethylpyrrolidine (623 mg, 4.86 mmol), TBTU (1.56 g, 4.86 mmol) and DIEA (830 µl, 4.86 mmol) in DCM (80 ml) were stirred at room temperature under nitrogen atmosphere overnight. The reaction was monitored by tlc (AcOEt/PE 40:60) and stopped after 12 h. The mixture was washed with brine, dried over magnesium sulfate, filtered and concentrated. The crude (3.8 g) was purified by fast-plug with AcOEt/PE 60:40 then DCM/MeOH/NH₄OH 90:10:0.1.

yield: quantitative (3.2 g)

¹H NMR (DMSO): 0.87 (t, J=9.0 Hz, 3H), 1.18 (s, 9H), 1.32 (m, 1H), 1.36 (m, 2H), 1.48 (m, 1H), 2.20-2.8 (m, 7H), 3.20 (m, 2H), 3.55 (m, 2H), 4.08 (m, 4H), 4.10 (m, 1H), 4.25 (m, 1H), 7.05-7.25 (m, 4H), 7.34-7.39 (m, 2H), 7.46-7.69 (m, 2H), 7.80 (m, 1H)

Intermediate 16: N~3~-[(1-ethylpyrrolidin-2-yl)methyl]-N~1~-(4-phenoxyphenyl)-piperazine-1,3-dicarboxamide (Scheme 2, compound XVI)

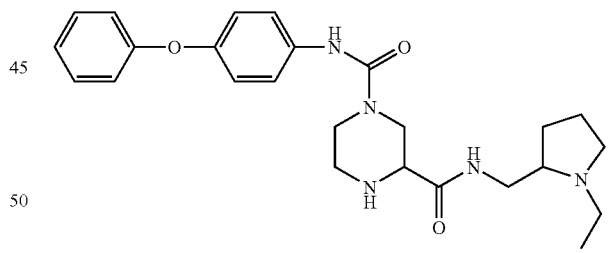

Intermediate 15 (200 mg, 0.36 mmol) was dissolved in DCM (8 ml) under nitrogen atmosphere. The solution was cooled to 0° C. and TFA (360 ml) was slowly added. After 20 min, the solution was brought back to room temperature and the reaction was monitored by tlc (DCM/MeOH/NH₄OH 90:10:0.1). After 6 h, the reaction was not completed, 300 ml TFA were added and the mixture stirred for another 12 h at room temperature. The solution was then concentrated, dried under reduced pressure and redissolved in DCM (8 ml). 4-phenoxyphenylisocyanate (114 mg, 0.54 mmol) dissolved in DCM (2 ml) and DIEA (120 µl, 0.72 mmol) were added. The new reaction mixture was stirred at room temperature for 18 h. In between, another equivalent of 4-phenoxyphenylisocyanate (114 mg) was added to complete the reaction. The solution was washed with brine, dried over magnesium sulfate, filtered and concentrated. The crude was purified by flash chromatography with DCM/MeOH 90:10 to give 108 mg (45%) of the Fmoc intermediate. It was redissolved in dry DCM (5 ml) and piperidine (60 μl, 0.57 mmol) was added. The mixture was stirred at room temperature for 18 h and washed with brine, dried over magnesium sulfate, filtered and concentrated. The crude thus obtained was purified by flash chromatography with DCM/MeOH/NH$_4$OH 90:10:0.1. Yield: 31% (50 mg)

$^1$H NMR (DMSO): 1.08 (t, J=6.8 Hz, 3H), 1.40-1.90 (m, 4H), 2.65 (m, 1H), 2.87 (d, J=12.8 Hz, 2H), 3.01 (m, 3H), 3.04-3.50 (m, 6H), 3.71 (d, J=12.0 Hz, 1H), 3.97 (d, J=10.5 Hz, 1H), 6.90 (m, 4H), 7.07 (t, J=7.3 Hz, 1H), 7.34 (m, 2H), 7.43 (d, J=9.0 Hz, 2H), 8.0 (m, 1H), 8.56 (s, 1H).

Example 1

4-(2'-Methyl-biphenyl-4-sulfonyl)-piperazine-1,3-dicarboxylic acid 3-[(1-ethyl-pyrrolidin-2-ylmethyl-amide]1-[(4-phenoxy-phenyl)-amide]fumarate (Scheme 2, compound I)

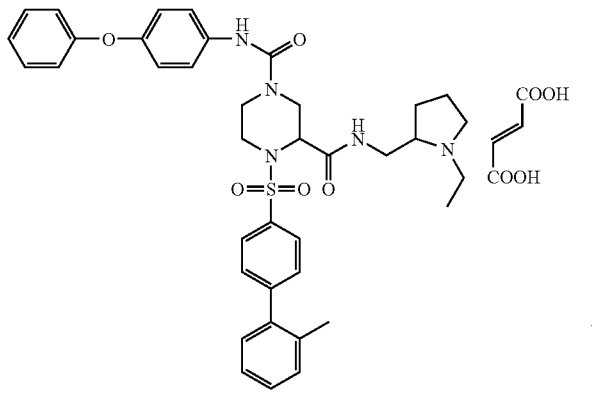

Intermediate 16 (50 mg, 0.11 mmol) and 2'-methylbiphenyl-4-sulfonylchloride (35 mg, 0.13 mmol) in DCM (4 ml) were stirred at room temperature in presence of DIEA (20 μl, 0.13 mmol). After 3 h, 2'-methylbiphenyl-4-sulfonylchloride (20 mg) and DIEA (20 ml) were added to complete the reaction and the mixture was heated under reflux for an additional 4 h. Finally, it was washed with saturated NaHCO$_3$ and brine, dried over magnesium sulfate, filtered and concentrated. The crude was purified by flash chromatography with DCM/MeOH 90:10. Yield: 97% (50 mg)

The fumarate salt was obtained by dissolving the compound in MeOH in presence of 0.9 eq. fumaric acid. The solution thus obtained was then concentrated and the resulting oil triturated in Et$_2$O to give a nice white solid which was filtrated and dried.

$^1$H NMR (DMSO): 1.02 (m, 3H), 1.41-1.81 (m, 4H), 2.21 (s, 3H), 2.25 (m, 2H), 2.72-3.14 (m, 7H), 3.68 (m, 2H), 4.00 (brd, J=11.7 Hz, 1H), 4.30 (brd, J=13.2 Hz, 1H), 4.45 (m, 1H), 6.57 (s, 2H), 6.85-6.91 (m, 4H), 7.06 (m, 1H), 7.18-7.35 (m, 8H), 7.53 (d, J=7.9 Hz, 2H), 7.83 (dd, J=8.3 and 3.0 Hz, 2H), 8.14 (m, 1H), 8.52 (d, J=3.0 Hz, 1H).

MS: (APCI-): 680 (M-1), 469; HPLC purity: 98.3%

Example 2

(3R)-4-(Biphenyl-4-sulfonyl)-piperazine-1,3-dicarboxylic acid 1-[(4-benzyloxy-phenyl)-amide]-3-{(2R)[1-ethyl-pyrrolidin-2-ylmethyl]-amide}trifluoroacetate. (Schemes 2 and 3, compound I)

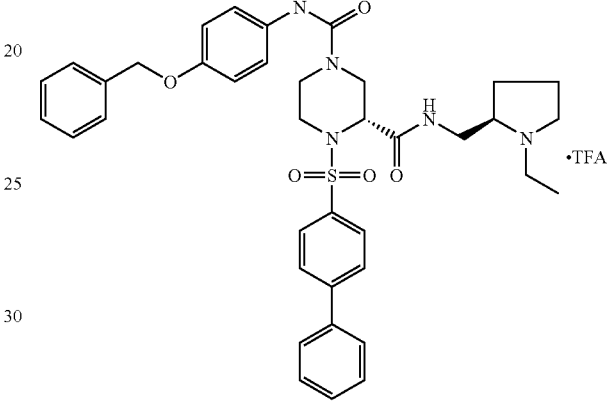

(2R)-4-(tert-butoxycarbonyl)-1-(biphenyl-4-sulfonyl)piperazine-2-carboxylic acid (429 g, 9.62 mmol) obtained following the procedure described for intermediate 4 but starting from the pure (R)-2-carboxypiperazine.2CSA was dissolved in DCM (50 ml). (2R)-1-ethyl-2-aminoethylpyrrolidine (1.54 g, 10.58 mmol), HATU (4.02 g, 10.58 mmol) and DIEA (3.68 ml, 21.15 mmol) were added and the mixture stirred overnight at room temperature. It was then washed with HCl 1N, saturated NaHCO$_3$ and brine, dried over magnesium sulfate, filtrated and concentrated. TFA (50 ml) was added to the oily solid thus obtained and the mixture was stirred in an ice bath for half hour and two hours at room temperature. TFA was then removed under reduced pressure and the oily solid obtained was coevaporated three time with DCM and dried under vacuum. It was redissolved in DCM (20 ml), 4-(benzyloxy)phenylisocyanate (4.32 g, 19.23 mmol) and DIEA (8.36 ml, 48 mmol) were added and the mixture stirred overnight at room temperature. The solution was washed with HCl 1N, saturated NaHCO$_3$ and brine, dried over magnesium sulfate, filtered and concentrated. About 10% of this crude was purified by preparative HPLC (Novapack column; 40-80% ACN/water-TFA 0.1% in 40 mn) and characterized:

$^1$H NMR (DMSO): 1.11 (t, J=7.2 Hz, 3H), 1.61 (m, 1H), 1.75 (m, 2H), 2.02 (m, 1H), 2.90 (m, 2), 3.05-3.18 (m, 7H), 3.64 (m, 2H), 3.95 (d, J=13.2 Hz, 1H), 4.32 (d, J=13.2 Hz,

1H), 4.42 (brs, 1H), 5.01 (s, 2H), 6.85 (d, J=9.0 HZ, 2H), 7.19 (d, J=9.0 Hz, 2H), 7.30-7.53 (m, 8H), 7.73 (d, J=7.2 Hz, 2H), 7.88 (s, 4H), 8.36 (s, 1H), 8.49 (t, J=5.8 Hz, 1H), 9.05 (brs, 1H).

MS (APCI+): 682 (M+1); (APCI−): 680 (M−1)

de=92% (determined by HPLC Waters symmetry C8 5 μM 4.6×250 mm; H$_2$O/ACN/TFA 60.40.01)

Example 3

(3R)-4-Biphenyl-4-sulfonyl)-piperazine-1,3-dicarboxylic acid 1-[(4-benzyl-oxyphenyl)-amide]-3-{(2S)[1-ethyl-pyrrolidin-2-ylmethyl]-amide}trifluoroacetate (Schemes 2 and 3, compound I)

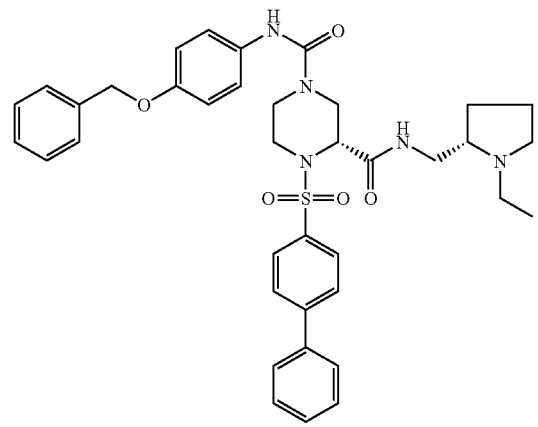

Example 3 was prepared following the procedure described for example 2 from (2R)-4-(tert-butoxycarbonyl)-1-(biphenyl-4-sulfonyl)piperazine-2-carboxylic acid and (2S)-1-ethyl-2-aminoethylpyrrolidine.

$^1$H NMR (DMSO): 0.90 (t, J=7.2 Hz, 3H), 1.79 (m, 3H), 2.01 (m, 1H), 2.86-3.39 (m, 9H), 3.65 (brs, 2H), 4.02 (d, J=13.2 Hz, 1H), 4.33 (d, J=13.6 Hz, 1H), 4.43 (s, 1H), 5.02 (s, 2H), 6.86 (d, J=9.0 Hz, 2H), 7.17 (d, J=9.0 Hz, 2H), 7.29-7.54 (m, 8H), 7.73 (d, J=6.8 Hz, 2H), 7.80 (m, 4H), 8.36 (m, 1H), 8.47 (s, 1H), 8.60 (t, J=4.7 Hz, 1H).

MS (APCI+): 682 (M+1); (APCI−): 680 (M−1)

de=92% (determined by HPLC Waters symmetry C8 5 μM 4.6×250 mm; H$_2$O/ACN/TFA 60.40.01)

Example 4

(3S)-4-(Biphenyl-4-sulfonyl)piperazine-1,3-dicarboxylic acid 1-[(4-benzyloxy-phenyl)-amide]-3-{(2S)[1-ethyl-pyrrolidin-2-ylmethyl]-amide}trifluoroacetate (Schemes 2 and 3, compound I)

Example 4 was prepared following the procedure described for example 2 from (2S)-tert-butoxycarbonyl-1-(biphenyl-4-sulfonyl)piperazine-2-carboxylic acid obtained following the procedure described for intermediate 4 but starting from the pure (S)-2-carboxypiperazine.2CSA and (2S)-1-ethyl-2-aminoethylpyrrolidine.

$^1$H NMR (DMSO): same as example 2. de=94%

Example 5

(3S)-4-(Biphenyl-4-sulfonyl)-piperazine-1,3-dicarboxylic acid 1-[(4-benzyloxy-phenyl)-amide]-3-{(2R)[1-ethyl-pyrrolidin-2-ylmethyl]-amide}trifluoroacetate (Schemes 2 and 3, compound I)

Example 5 was prepared following the procedure described for example 4 from (2S)-(tert-butoxycarbonyl)-1-(biphenyl-4-sulfonyl)piperazine-2-carboxylic acid and (2R)-1-ethyl-2-aminoethylpyrrolidine.

¹H NMR (DMSO): same as example 3. de=95.2%

Example 6

(2S)-4-[(4-tert-butylphenyl)sulfonyl]-N-(2-hydroxyethyl)-1-(quinolin-8-ylsulfonyl)piperazine-2-carboxamide (Scheme 1, compound I)

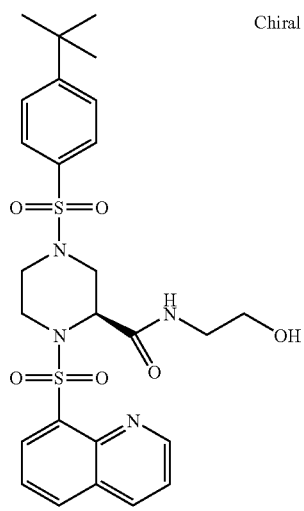 [SMILES: CC(C)(C)c1ccc(S(=O)(=O)N2CCN(S(=O)(=O)c3cccc4cccnc34)[C@H](C(=O)NCCO)C2)cc1]

A solution of intermediate 10 (600 mg, 1.16 mmol) and DIEA (445 µl, 2.55 mmol) in DMF (7 ml) was cooled to 6° C. TBTU (409 mg, 1.28 mmol) was then added and the mixture was stirred in an ice cold bath for 1 h. Finally, ethanolamine (140 µl, 2.32 mmol) was added. The reaction mixture was allowed to warm to room temperature and stirred overnight. Water (11 ml) was added to the solution and the solid thus obtained was filtered, washed three times with water and dried to afford the desired amide.

Yield: 65% (420 mg). LC/MS: ESI (+): 561 (M+1); ESI (−): 559(M−1); HPLC purity: 99.9%; ee>98% (Column CHIRALCELL OD-H, 4.6×250 mmm; hex/EtOH/TEA 70 30 0.1)

Example 7

(2R)-4-[(4-tert-butylphenyl)sulfonyl]-N-(2-hydroxyethyl)-1-(quinolin-8-ylsulfonyl)piperazine-2-carboxamide (Scheme 1, compound I)

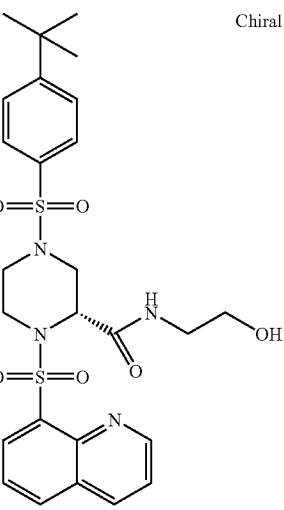

The title compound was obtained following the procedure described in example 6 starting from intermediate 11 and ethanolamine.

LC/MS: ESI (+): 561 (M+1); ESI (−): 559 (M−1); HPLC purity: 99.4% ee=26% (Column CHIRALCELL OD-H, 4.6×250 mmm; hex/EtOH/TEA 70 30 0.1)

Example 8

(2S)-4-[(4-tert-butylphenyl)sulfonyl]-N-Drop-2-enyl-1-(quinolin-8-ylsulfonyl)piperazine-2-carboxamide (Scheme 1, compound I)

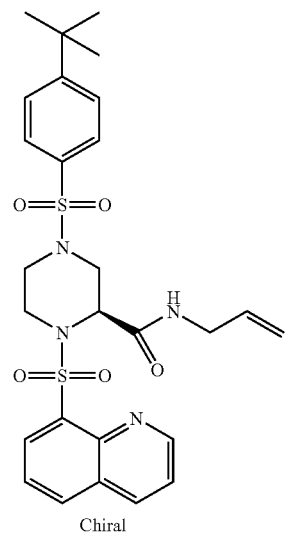 [SMILES: C=CCNC(=O)[C@@H]1CN(S(=O)(=O)c2ccc(C(C)(C)C)cc2)CCN1S(=O)(=O)c1cccc2cccnc12]

The title compound was obtained following the procedure described in example 6 starting from intermediate 10 and allylamine.

LC/MS: ESI (+): 557 (M+1); ESI (−): 555(M−1); HPLC purity: 99.3% ee>98% (Column CHIRALCELL OD-H, 4.6×250 mmm; hex/EtOH/TEA 70 30 0.1)

Example 9

(2R)-4-[(4-tert-butylphenyl)sulfonyl]-N-prop-2-enyl-1-(quinolin-8-ylsulfonyl)piperazine-2-carboxamide hydrochloride (Scheme 2, compound I)

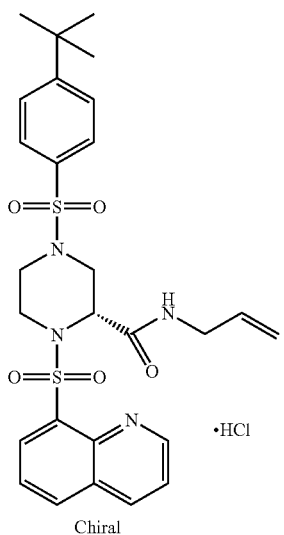 [SMILES: C=CCNC(=O)[C@H]1CN(S(=O)(=O)c2ccc(C(C)(C)C)cc2)CCN1S(=O)(=O)c1cccc2cccnc12 ; Cl]

A solution of intermediate 14 (previously desalinized, 852 mg, 2.36 mmol) and 4-tert-butylphenylsulfonylchloride (660 mg, 2.84 mmol) in presence of DIEA (603 μl, 3.55 mmol) in DCM (50 ml) was stirred at room temperature for 48 h. The mixture was then washed with saturated NH₄Cl solution, saturated NaHCO₃ solution and brine. It was dried over magnesium sulfate, filtered and concentrated. The crude (1.37 g) was purified by flash chromatography with AcOEt/cHex 50:50 to give a nice white foam. The hydrochloride salt was obtained by dissolving this foam in methanol and addition of 20 ml HCl 1N in MeOH. After evaporation of the MeOH, the oil was triturated in Et₂O and the white solid thus obtained was filtrated and dried. Yield: 57% (796 mg).

¹H NMR (DMSO): 1.27 (s, 9H), 1.71 (m, 1H), 2.07 (m, 1H), 3.44 (m, 1H), 3.58-3.71 (m, 4H), 4.02 (d, J=11.7 Hz, 1H), 4.98 (brs, 1H), 5.02 (d, J=10.5 Hz, 1H), 5.14 (d, J=15.4 Hz, 1H), 5.72 (m, 1H), 7.46 (d, J=8.7 Hz, 2H), 7.54 (d, J=8.3 Hz, 2H), 7.63 (m, 1H), 7.69 (d, J=7.9 Hz, 1H), 8.12 (t, J=5.7 Hz, 1H), 8.23 (d, J=7.2 Hz, 1H), 8.32 (d, J=7.5 Hz, 1H), 8.44 (d, J=7.15 Hz, 1H), 8.89 (d, J=3 Hz, 1H).

LC/MS: ESI (+): 557 (M+1); ESI (−): 555(M−1); HPLC purity: 99.4% ee=89% (Column CHIRALCELL OD-H, 4.6×250 mmm; hex/EtOH/TEA 70 30 0.1)

Melting point: 126-129° C.

Example 10

(2R)-4-[(4-tert-butylphenyl)sulfonyl]-N-[(1S)-3-hydroxy-1-phenylpropyl]-1-(quinolin-8-ylsulfonyl)piperazine-2-carboxamide (Scheme 1, compound I)

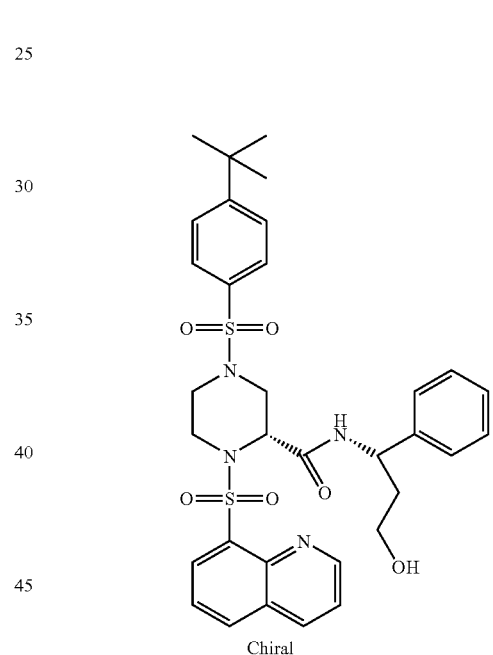

A solution of intermediate 11 (47 mg, 0.09 mmol) in THF (1 ml) was cooled to −10° C. before the addition of isobutylchloroformate (11 μl, 0.10 mmol) and NMM (15 μl, 0.14 mmol). The reaction mixture was stirred for 1 h at −40° C. and (S)-1-phenyl-3-propanolamine (15 mg, 0.10 mmol) solubilized in THF (1 ml) was added. It was allowed to warm to room temperature and stirred overnight. THF was evaporated under reduced pressure and the oil obtained was dissolved in AcOEt. The organic phase was washed with saturated NH₄Cl, saturated NaHCO₃ and brine, dried over magnesium sulfate, filtrated and concentrated. The crude was purified by flash chromatography with DCM/MeOH 94:6 to give the title compound. Yield: 30% (18 mg)

$^1$H NMR (CDCl$_3$): 1.34 (s, 9H), 1.87 (m, 1H), 2.41 (m, 3H), 3.18-3.40 (m, 2H), 3.63-3.74 (m, 2), 4.21 (d, J=15.0 Hz, 1H), 4.42 (d, J=12.0 Hz, 1H), 5.08 (m, 2H), 6.84 (m, 1H), 7.12 (m, 3H), 7.28 (m, 2H), 7.38 (m, 1H), 7.47 (m, 2H), 7.63 (m, 3H), 8.07 (d, J=9.4 Hz, 1H), 8.21 (d, J=8.7 Hz, 1H), 8.41 (d, J=8.7 Hz, 1H), 8.62 (brs, 1H).

MS: ESI+: 651 (M+1); ESI−: 649 (M−1); HPLC purity: 89%

Example 11

(2R)-4-[(4-tert-butylphenyl)sulfonyl]-N-[(1R)-3-hydroxy-1-phenylpropyl]-1-(quinolin-8-ylsulfonyl) piperazine-2-carboxamide (Scheme 1, compound I)

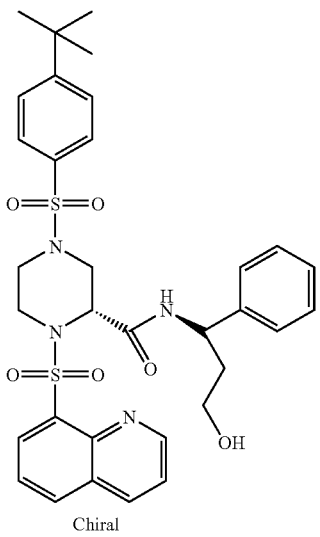

Chiral

The title compound was obtained following the procedure described in example 10 starting from intermediate 11 and (R)-1-phenyl-3-propanolamine.

$^1$H NMR (CDCl$_3$): 1.34 (s, 9H), 1.57 (m, 1H), 1.77-2.02 (m, 1H), 2.41-2.55 (m, 2H), 3.39-3.83 (m, 5H), 4.23 (d, J=14.3 Hz, 1H), 4.42 (d, J=11.7 Hz, 1H), 5.00 (m, 2H), 6.78 (m, 1H), 7.00-7.10 (m, 3H), 7.26 (m, 1H), 7.32 (m, 1H), 7.46 (d, J=8.7 Hz, 2H), 7.55-7.63 (m, 3H), 7.97 (d, J=8.3 Hz, 1H), 8.14 (d, J=8.7 Hz, 1H), 8.38 (d, J=7.1 Hz, 1H), 8.79 (d, J=4.1 Hz, 1H).

MS: ESI+: 651 (M+1); ESI−: 649 (M−1); HPLC purity: 98.2%

Example 12

(2R)-4-[(4-tert-butylphenyl)sulfonyl]-N-[(1S)-3-hydroxy-1-phenylpropyl]-1-(quinolin-8-ylsulfonyl) piperazine-2-carboxamide (Scheme 1, compound I)

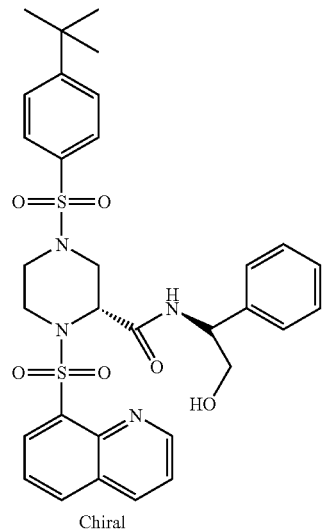

Chiral

The title compound was obtained following the procedure described in example 10 starting from intermediate 11 and (S)-1-phenyl-3-ethanolamine.

$^1$H NMR (CDCl$_3$): 1.35 (s, 9H), 2.56 (m, 2H), 3.39-3.72 (m, 4H), 3.84 (m, 1H), 4.27 (d, J=13.6 Hz, 1H), 4.47 (d, J=11.7 Hz, 1H), 4.71 (m, 1H), 4.87-4.99 (m, 1H), 6.60 (m, 1H), 7.02 (m, 4H), 7.21-7.39 (m, 2H), 7.45 (m, 2H), 7.60 (m, 2H), 8.01 (t, J=8.3 Hz, 1H), 8.17 (m, 1H), 8.41 (d, J=7.3 Hz, 1H), 8.69 (brs, 1H).

MS: ESI+: 637 (M+1); ESI−: 635 (M−1); HPLC purity: 98.2%

Example 13

(2R)-4-[(4-tert-butylphenyl)sulfonyl]-N-[(1R)-3-hydroxy-1-phenylpropyl]-1-(quinolin-8-ylsulfonyl) piperazine-2-carboxamide (Scheme 1, compound I)

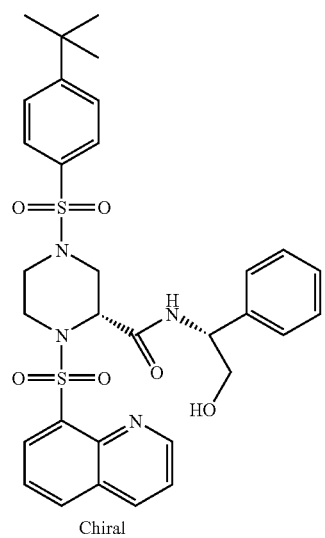 [SMILES: CC(C)(C)c1ccc(S(=O)(=O)N2CCN(S(=O)(=O)c3cccc4cccnc34)[C@@H](C(=O)N[C@@H](CO)c3ccccc3)C2)cc1]

Chiral

The title compound was obtained following the procedure described in example 10 starting from intermediate 11 and (R)-1-phenyl-3-ethanolamine.

$^1$H NMR (CDCl$_3$): 1.32 (s, 9H), 2.51 (m, 1H), 3.36-3.64 (m, 4H), 3.85 (m, 1H), 4.17 (d, J=14.3 Hz, 1H), 4.41 (d, J=11.7 Hz, 1H), 4.84 (m, 1H), 5.00 (m, 1H), 7.07 (m, 3H), 7.23 (m, 2H), 7.32 (m, 1H), 7.55 (m, 2H), 7.60 (m, 3H), 8.00 (dd, J=13 and 8.1 Hz, 1H), 8.16 (dd, J=1.5 and 8.3 Hz, 1H), 8.40 (dd, J=0 0.9 and 7.0 Hz, 1H), 8.70 (dd, J=1.5 and 4.1 Hz, 1H).

MS: ESI+: 637 (M+1); ESI−: 635 (M−1); HPLC purity: 96.1%

Example 14

(2R)-1-[(4-tert-butylphenyl)sulfonyl]-N-prop-2-enyl-4-(quinolin-8-ylsulfonyl)piperazine-2-carboxamide
(Scheme 1, compound I)

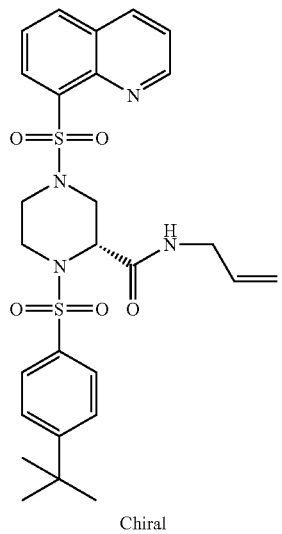 [SMILES: C=CCNC(=O)[C@H]1CN(S(=O)(=O)c2cccc3cccnc23)CCN1S(=O)(=O)c1ccc(C(C)(C)C)cc1]

Chiral

Intermediate 12 (260 mg, 0.50 mmol) was dissolved in DCM (10 ml) and stirred 15 mn at room temperature in presence of HOBt (81 mg, 0.60 mmol), EDC (116 mg, 0.60 mmol), and DIEA (190 µl, 1.26 mmol). Allylamine (42 µl, 0.55 mmol) was then added and the mixture was stirred at room temperature overnight. The solution was washed with saturated NH$_4$Cl, saturated NaHCO$_3$ and with brine (twice). It was dried over magnesium sulfate, filtered and concentrated to give 274 mg of crude material. Purification was performed by flash chromatography with cHex/AcOEt 50:50.

Yield: 50% (140 mg); LC/MS: ESI+: 557 (M+1); ESI−: 555(M−1); HPLC purity: 97%

$^1$H NMR (CDCl$_3$): 1.31 (s, 9H), 2.7 (m, 2H), 3.32-3.55 (m, 3H), 3.88 (d, J=14.3 Hz, 1H), 4.22 (d, J=13.2 Hz, 1H), 4.31 (d, J=12.4 Hz, 1H), 4.39 (brs, 1H), 4.97 (m, 2H), 5.47 (m, 1H), 6.45 (t, J=5.5 Hz, 1H), 7.49 (d, J=8.7 Hz, 2H), 7.65 (m, 1H), 7.71 (d, J=8.3 Hz, 2H), 7.76 (m, 1H), 8.14 (d, J=7.16 Hz, 1H), 8.44 (d, J=6.8 Hz, 1H), 8.53 (dd, J=1.5 and 7.5 Hz, 1H), 9.30 (d, J=4.5 Hz, 1H).

Example 15

General Protocol for the Solid-Phase Synthesis of Piperazine Derivatives of General Formula I
(Scheme 5)

a) Loading Step

Kaiser oxime resin (3 g, 6.28 mmol) was swollen in DCM (30 ml). The relevant acid (intermediates 1 to 8, 2 eq. and DIC (2 eq.) were slowly added and the resulting suspension was shaken overnight before filtering at the pump and washing sequentially with DCM, DMF (three times), TBME (twice) and dried in vacuo.

b) N-Deprotection Step

The resin obtained in the loading step (5 g) was shaken in a 25% solution of TFA in dichloromethane (50 ml) for 30 min prior to filtering at the pump and washing sequentially with DCM, DMF (three times) and TBME (twice). It was finally dried under vacuo at room temperature.

c) N-Capping Step

The resin from the previous step was transferred into a 96-well filter plate (approx. 50 mg of dry resin/well) and each well was treated with an N-derivatising reagent e.g. with either of the following solutions:

1—an acid (3 eq.) and DIC (3 eq.) in DCM (1 ml)

2—a sulfonyl chlorid (3 eq.) in DCM (1 ml)

3—an isocyanate (3 eq.) in DCM (1 ml)

The plate was then sealed and shaken overnight at ambient temperature. The resins were then filtrated and washed sequentially with aliquots of DCM, DMF (three times) and TBME (twice) before drying at room temperature under vacuo.

d) Cleavage Step

A solution of amine (0.9 eq. or 5 eq. if volatile) in 2% AcOH in DCM (1 ml) was added to each well containing the resin from the previous step. The plates were then sealed and shaken for two days at ambient temperature. The wells were then filtered into a collection plate and the solvent removed in a vacuum centrifuge to yield 2-3 mg of the corresponding products.

Example 16

(3R)—N~3~-(2-hydroxy-2-phenylethyl)-N~3~-methyl-N~1~-(4-phenoxy-phenyl)-4-(phenylsulfonyl)piperazine-1,3-dicarboxamide (Scheme 5, compound I)

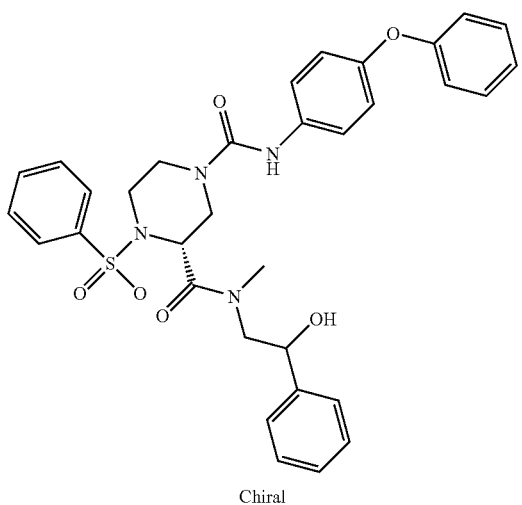

Chiral

The title compound was obtained following the general procedure described in example 15 starting from (2R)-4-(tert-butoxycarbonyl)-1-(benzenesulfonyl)piperazine-2-carboxylic acid obtained following the procedure described for intermediate 1 but starting from the pure (R)-2-carboxypiperazine.2CSA, 4-phenoxyphenylisocyanate and 2-methylamino-1-phenylethanol.

¹H NMR (CDCl₃): 2.86 (m, 1H), 3.14-3.36 (m, 5H), 3.71-4.42 (m, 5H), 4.90-4.98 (m, 2H), 6.86-6.98 (m, 4H), 7.07 (m, 1H), 7.22-7.56 (m; 10H), 7.83 (m, 3), 8.03 (m, 2H).

LC/MS: ESI+: 615 (M+1); ESI−: 613 (M−1); HPLC purity: 98.0%

Example 17

(3S)—N~3~-(2-hydroxy-2-phenylethyl)-N~3~-methyl-N~1~-(4-phenoxy-phenyl)-4-(phenylsulfonyl)piperazine-1,3-dicarboxamide (Scheme 5, compound I)

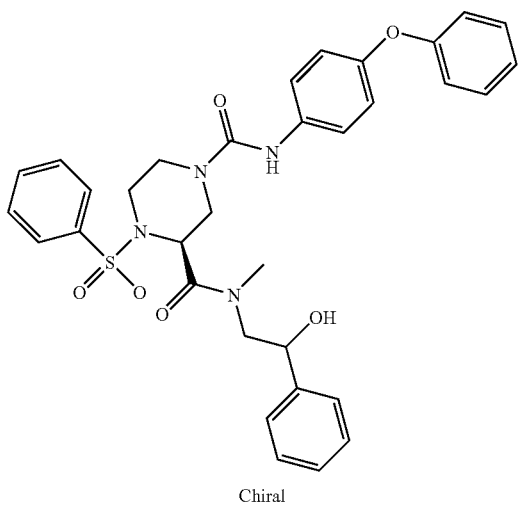

Chiral

The title compound was obtained following the general procedure described in example 15 starting from (2S)-4-(tert-butoxycarbonyl)-1-(benzenesulfonyl)piperazine-2-carboxylic acid obtained following the procedure described for intermediate 1 but starting from the pure (S)-2-carboxypiperazine.2CSA, 4-phenoxyphenylisocyanate and 2-methylamino-1-phenylethanol.

¹H NMR (CDCl₃): 2.78 (m, 1H), 3.03-3.28 (m, 5H), 3.62-4.33 (m, 5H), 4.81-4.90 (m, 2H), 6.77-6.88 (m, 4H), 6.97 (m, 1H), 7.12-7.47 (m, 10H), 7.73 (m, 3H), 7.93 (m, 2H).

LC/MS: ESI+: 615 (M+1); ESI−: 613 (M−1); HPLC purity: 99.5%

Example 18

(3R)-4-(3-chlorobenzoyl)-N~1~-(3,4-dichlorophenyl)-N~3~-[(1R)-2,3-dihydro-1H-inden-1-yl]piperazine-1,3-dicarboxamide (Scheme 5, compound I)

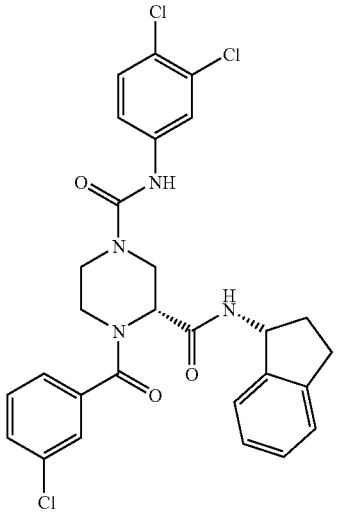

The title compound was obtained following the general procedure described in example 15 starting from (2R)-4-(tert-butoxycarbonyl)-1-(3-chloro-benzoyl)piperazine-2-carboxylic acid obtained following the procedure described for intermediate 7 but starting from the pure (R)-2-carboxypiperazine.2CSA, 3,4-dichlorophenylisocyanate and (R)-1-amino-indane.

¹H NMR (CDCl₃): 1.66 (m, 1H), 2.59 (m, 1H), 2.81-3.31 (m, 4H), 3.64 (d, J=13.4 Hz, 1H), 4.25 (d, J=12.5 Hz, 1H), 4.45 (d, 1H), 4.54 (d, J=14.8 Hz, 1H), 5.26 (s, 1H), 5.46 (m, 1H), 6.75 (m, 1H), 7.17-7.50 (m, 11H), 8.94 (s, 1H).

LC/MS: ESI+: 572 (M+1); ESI−: 570 (M−1); HPLC purity: 99.3%

Example 19

(3R)-4-(3-chlorobenzoyl-N~1~-(3,4-dichlorophenyl)-N~3~-[(1S)-2,3-dihydro-1H-inden-1-yl]piperazine-1,3-dicarboxamide (Scheme 5, compound I)

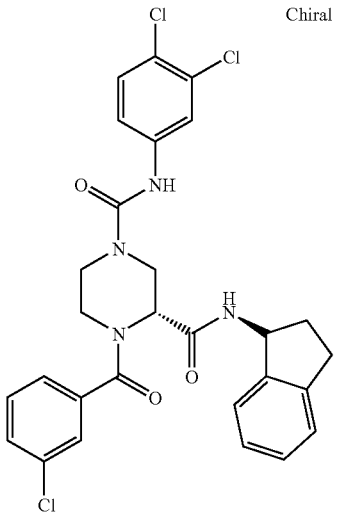

Chiral

The title compound was obtained following the general procedure described in example 15 starting from (2R)-4-(tert-butoxycarbonyl)-1-(3-chloro-benzoyl)piperazine-2-carboxylic acid obtained following the procedure described for intermediate 7 but starting from the pure (R)-2-carboxypiperazine.2CSA, 3,4-dichlorophenylisocyanate and (S)-1-aminoindane.

$^1$H NMR (CDCl$_3$): 1.84 (m, 1H), 2.65 (m, 1H), 2.81-3.01 (m, 4H), 3.23 (d, J=14.0 Hz, 1H), 3.67 (d, J=13.2 Hz, 1H), 4.28 (d, J=12.0 Hz, 1H), 4.54 (d, J=14.6 Hz, 1H), 5.24 (s, 1H), 5.46 (m, 1H), 6.72 (m, 1H), 7.16-7.98 (m, 1H), 8.85 (s, 1H).

LC/MS: ESI+: 572 (M+1); ESI−: 570 (M−1); HPLC purity: 97.9%

Example 20

(3S)-4-(3-chlorobenzoyl)-N~1~-(3,4-dichlorophenyl)-N~3~-[(1R)-2,3-dihydro-1H-inden-1-yl]piperazine-1,3-dicarboxamide (Scheme 5, compound I)

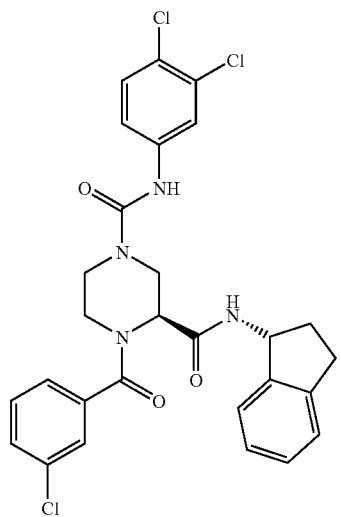

The title compound was obtained following the general procedure described in example 15 starting from (2S)-4-(tert-butoxycarbonyl)-1-(3-chloro-benzoyl)piperazine-2-carboxylic acid obtained following the procedure described for intermediate 7 but starting from the pure (S)-2-carboxypiperazine.2CSA, 3,4-dichlorophenylisocyanate and (R)-1-aminoindane.

$^1$H NMR (CDCl$_3$): same as for example 19; LC/MS: ESI+: 572 (M+1); ESI−: 570 (M−1)

HPLC purity: 99.3%

Example 21

(3S)-4-(3-chlorobenzoyl)-N~1~-(3,4-dichlorophenyl)-N~3~-[(1S)-2,3-dihydro-1H-inden-1-yl]piperazine-1,3-dicarboxamide (Scheme 5, compound I)

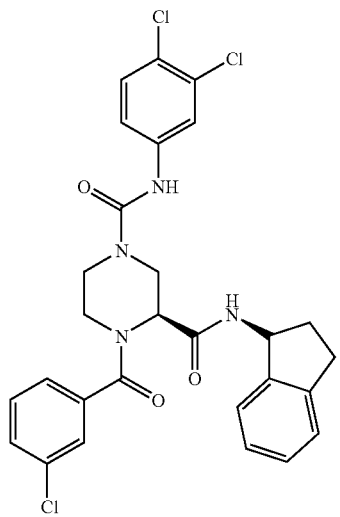

The title compound was obtained following the general procedure described in example 15 starting from (2S)-4-(tert-butoxycarbonyl)-1-(3-chloro-benzoyl)piperazine-2-carboxylic acid obtained following the procedure described for intermediate 7 but staring from the pure (S)-2-carboxypiperazine.2CSA, 3,4dichlorophenylisocyanate and (R)-1-aminoindane.

$^1$H NMR (CDCl$_3$): same as for example 18; LC/MS: ESI+: 572 (M+1); ESI−: 570 (M−1)

HPLC purity: 98.5%

Example 22

4-(Biphenyl-4-sulfonyl)-piperazine-1,3-dicarboxylic acid 1-[(4-benzyloxy-phenyl)-amide]3-[(2-dimethylamino-ethyl)-amide] (Scheme 5, compound I)

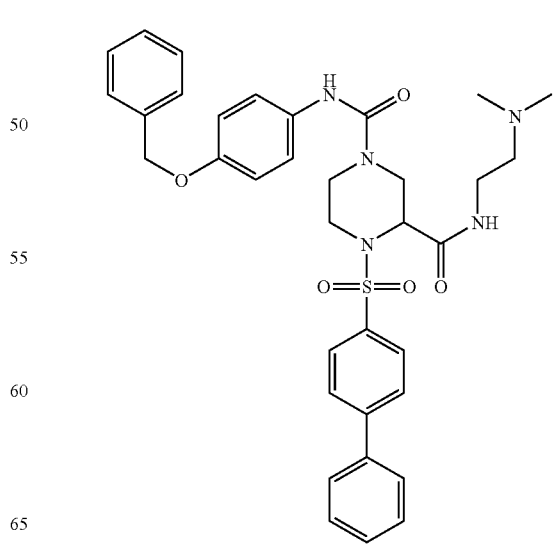

The title compound was obtained following the general procedure described in example 15 starting from intermediate 4,4-benzyloxyphenylisocyanate and 2dimethylaminoethylamine.

$^1$H NMR (CDCl$_3$): 2.4 (s, 6H), 2.6 (m, 2H), 2.73 (t, 1H), 3.0 (d, 1H), 3.34 (t, 1H), 3.5 (m, 2H), 4.1 (d, 1H), 4.3 (d, 1H), 4.62 (d, 1H), 4.8 (s, 1H), 5.2 (s, 2H), 7.0 (d, 2H), 7.4 (d, 2H), 7.45-7.7 (m, 10H), 7.8 (d, 2H), 7.95 (d, 2H), 8.12 (s, 2H).

LC/MS: ESI+: 642 (M+1); HPLC purity: 94%

Example 23

4-(Biphenyl-4-sulfonyl)-piperazine-1,3-dicarboxylic acid 3-[(2-dimethyl-amino-ethyl)-amide]1-[(4-phenoxy-phenyl)-amide] (Scheme 5, compound I)

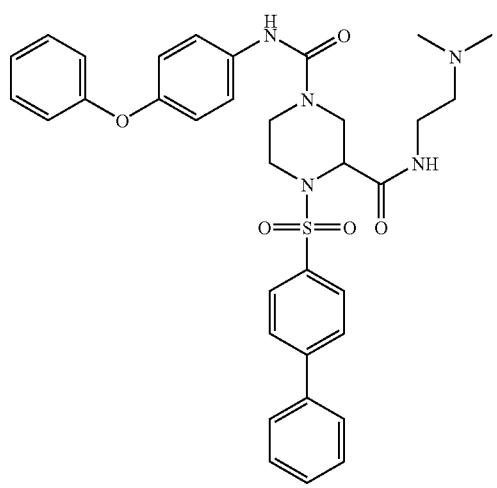 [SMILES: CN(C)CCNC(=O)C1CN(C(=O)Nc2ccc(Oc3ccccc3)cc2)CCN1S(=O)(=O)c1ccc(-c2ccccc2)cc1]

The title compound was obtained following the general procedure described in example 15 starting from intermediate 4,4-phenoxyphenylisocyanate and 2-dimethylaminoethylamine.

$^1$H NMR (CDCl$_3$): 2.15 (s, 6H), 2.33 (t, 2H), 2.50 (t, 1H), 2.75 (m, 1H), 3.08 (m, 1H), 3.3 (m, 2H), 3.82 (d, 1H), 4.08 (d, 1H), 4.4 (d, 1H), 4.55 (d, 1H), 6.85 (d, 4H), 6.95 (t, 1H), 7.2 (m, 4H), 7.4 (m, 3H), 7.55 (d, 2H), 7.7 (d, 2H), 7.88 (d, 2H), 8.03 (s, 1H).

LC/MS: ESI+: 628 (M+1); HPLC purity: 95%

Example 24

4-(Biphenyl-4-sulfonyl)-piperazine-1,3-dicarboxylic acid 1-[(3,4-dichloro-phenyl)-amide]3-[(1-ethyl-pyrrolidin-2-ylmethyl)-amide] (Scheme 5, compound I)

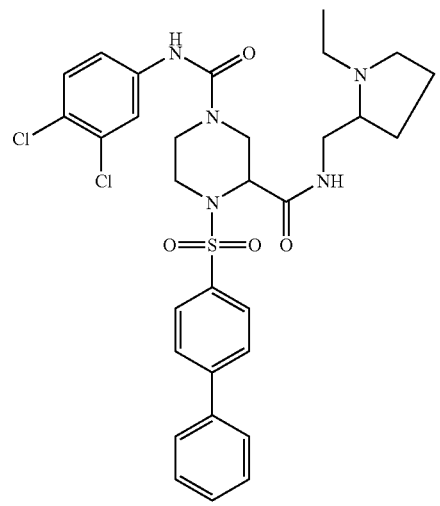 [SMILES: CCN1CCCC1CNC(=O)C1CN(C(=O)Nc2ccc(Cl)c(Cl)c2)CCN1S(=O)(=O)c1ccc(-c2ccccc2)cc1]

The title compound was obtained following the general procedure described in example 15 starting from intermediate 4,3,4-dichlorophenylisocyanate and 2-(aminomethyl)-1-ethylpyrrolidine.

$^1$H NMR (CDCl$_3$): 1.15-1.20 (m, 3H), 1.62-1.90 (m, 3H), 2.25 (m, 2H), 2.62 (m, 2H), 2.82 (m, 2H), 3.05-3.30 (m, 3H), 3.5 (m, 1H), 3.78 (t, 1H), 3.95 (d, 1H), 4.18 (d, 1H), 4.48 (d, 1H), 4.79 (s, 1H), 7.17 (d, 1H), 7.29 (d, 2H), 7.50 (m, 4H), 7.61 (d, 2H), 7.81 (d, 2H), 7.99 (d, 2H), 8.42 (s, 1H).

LC/MS: ESI+: 644 (M+1); HPLC purity: 93.8%

Example 25

4-(Biphenyl-4-sulfonyl)piperazine-1,3-dicarboxylic acid 3-[(1-ethyl-pyrrolidin-2-ylmethyl)-amide]1-[(4-phenoxy-phenyl)-amide] (Scheme 5, compound I)

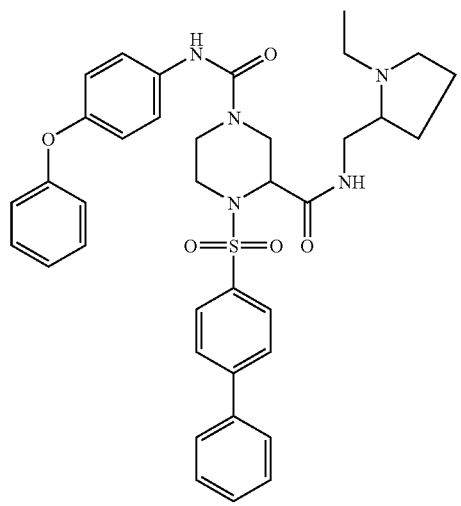 [SMILES: CCN1CCCC1CNC(=O)C1CN(C(=O)Nc2ccc(Oc3ccccc3)cc2)CCN1S(=O)(=O)c1ccc(-c2ccccc2)cc1]

The title compound was obtained following the general procedure described in example 15 starting from intermediate 4,4-phenoxyphenylisocyanate and 2-(aminomethyl)-1-ethyl-pyrrolidine.

$^1$H NMR (CDCl$_3$): 1.12 (m, 3H), 1.55 (m, 1H), 1.75 (m, 2H), 1.90 (m, 1H), 2.20 (m, 2H), 2.60 (m, 2H), 2.80 (m, 2H), 3.20 (m, 3H), 3.50 (m, 1H), 3.95 (d, 1H), 4.18 (d, 1H), 4.50 (d, 1H), 4.65 (s, 1H), 6.95 (d, 4H), 7.05 (t, 1H), 7.30 (m, 4H), 7.46 (m, 4H), 4.60 (d, 2H), 7.80 (d, 2H), 7.95 (d, 2H), 8.20 (s, 1H).

LC/MS: ESI+: 668 (M+1); HPLC purity 97.0%

Example 26

4-(Biphenyl-4-sulfonyl)-piperazine-1,3-dicarboxylic acid 1-[(3,4-dichloro-phenyl)-amide]3-[(2-diethy-lamino-ethyl)-amide] (Scheme 5, compound I)

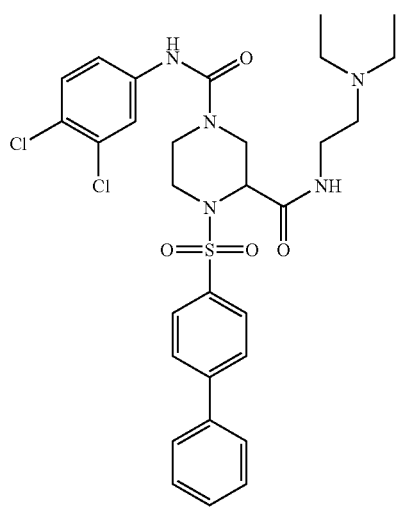 [SMILES: CCN(CC)CCNC(=O)C1CN(C(=O)Nc2ccc(Cl)c(Cl)c2)CCN1S(=O)(=O)c1ccc(-c2ccccc2)cc1]

The title compound was obtained following the general procedure described in example 15 starting from intermediate 4,3,4-dichlorophenylisocyanate and 2-diethyllaminoethy-lamine.

$^1$H NMR (CDCl$_3$): 1:00 (t, 6H), 2.57 (m, 7H), 2.78 (d, 1H), 3.19 (t, 1H), 3.36 (m, 1H), 3.42 (m, 1H), 4.00 (d, 1H), 4.12 (d, 1H), 4.46 (d, 1H), 4.49 (s, 1H), 7.20 (d, 1H), 7.31 (d, 1H), 7.52 (m, 4H), 7.63 (m, 3H), 7.82 (d, 2H), 8.00 (d, 2H), 8.46 (s, 1H).

LC/MS: ESI+: 632 (M+1); HPLC purity: 91.6%

Example 27

4-Diphenylacetyl-1-(quinoline-8-sulfonyl)-pipera-zine-2-carboxylic acid benzylamide (Scheme 5, compound I)

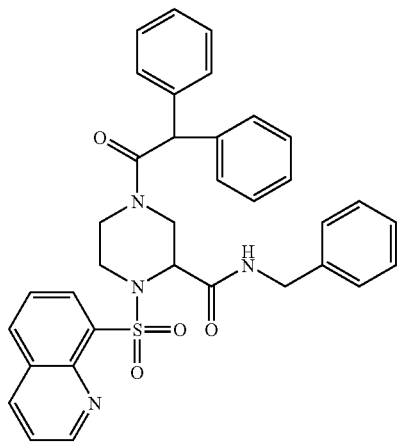 [SMILES: O=C(NCc1ccccc1)C1CN(C(=O)C(c2ccccc2)c2ccccc2)CCN1S(=O)(=O)c1cccc2cccnc12]

The title compound was obtained following the general procedure described in example 15 starting from intermediate 2, diphenylacetylchloride and benzylamine.

$^1$H NMR (CDCl$_3$): 2.82 (td, 1H), 2.98 (dd, 1H), 3.15 (td, 1H), 3.90 (d, 1H), 4.40 (dd, 1H), 4.52 (dd, 1H), 4.60 (d, 1H), 4.84 (d, 1H), 5.02 (s, 1H), 5.94 (s, 1H), 7.10 (m, 2H), 7.20-7.48 (m, 14H), 7.70 (t, 1H), 7.97 (d, 1H), 8.13 (d, 1H), 8.27 (d, 1H), 8.58 (d, 1H), 8.62 (d, 1H).

LC/MS: ESI+: 605 (M+1); HPLC purity: 98.0%

Example 28

4-(Biphenyl-4-sulfonyl)-piperazine-1,3-dicarboxylic acid 1-[(4-benzyloxy-phenyl)-amide]3-[(2-diethy-lamino-ethyl)-amide]

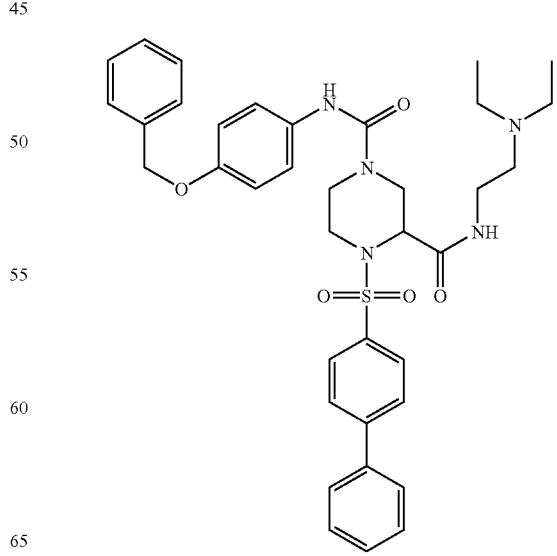

The title compound was obtained following the general procedure described in example 15 starting from intermediate 4,4-benzyloxyphenylisocyanate and 2-diethylaminoethylamine.

$^1$H NMR (CDCl$_3$): 1.10 (t, 6H), 2.60 (m, 7H), 2.80 (d, 1H), 3.20 (t, 1H), 3.37 (m, 1H), 4.44 (m, 1H), 4.00 (d, 1H), 4.18 (d, 1H), 4.50 (d, 1H), 4.65 (s, 1H), 5.08 (s, 2H), 6.90 (d, 2H), 7.28 (d, 2H), 7.33-7.60 (m, 10H), 7.69 (d, 1H), 7.82 (d, 2H), 8.00 (m, 3H).

LC/MS: ESI+: 670 (M+1); HPLC purity: 90.5%

Example 29

4-(Biphenyl-4-sulfonyl)-piperazine-1,3-dicarboxylic acid 3-[(2-diethylamino-ethyl)-amide]1-[(4-phenoxy-phenyl)amide] (Scheme 5, compound I)

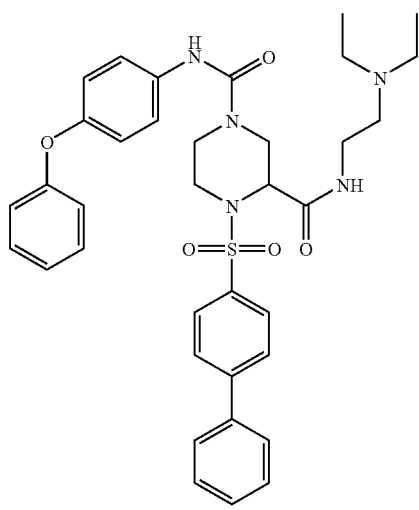 [SMILES: CCN(CC)CCNC(=O)C1CN(C(=O)Nc2ccc(Oc3ccccc3)cc2)CCN1S(=O)(=O)c1ccc(-c2ccccc2)cc1]

The title compound was obtained following the general procedure described in example 15 starting from intermediate 4,4-phenoxyphenylisocyanate and 2-diethylaminoethylamine.

$^1$H NMR (CDCl$_3$): 1.10 (t, 6H), 2.60 (m, 7H), 2.80 (d, 1H), 3.20 (t, 1H), 3.37 (m, 1H), 3.46 (m, 1H), 4.00 (d, 1H), 4.20 (d, 1H), 4.55 (d, 1H), 4.68 (s, 1H), 7.00 (d, 4H), 7.10 (t, 1H), 7.35 (m, 4H), 7.54 (m, 4H), 7.70 (d, 2H), 7.84 (d, 2H), 8.00 (d, 2H), 8.20 (s, 1H).

LC/MS: ESI+: 656 (M+1); HPLC purity: 92.7%

Example 30

4-Diphenylacetyl-1-(quinoline-8-sulfonyl)-piperazine-2-carboxylic acid (furan-2-ylmethyl)-amide (Scheme 5, compound I)

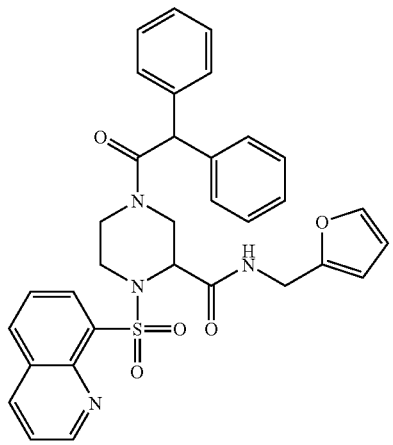 [SMILES: O=C(NCc1ccco1)C1CN(C(=O)C(c2ccccc2)c2ccccc2)CCN1S(=O)(=O)c1cccc2cccnc12]

The title compound was obtained following the general procedure described in example 15 starting from intermediate 2, diphenylacetylchloride and (2-furylmethyl)amine.

$^1$H NMR (CDCl$_3$): 2.83 (td, 1H), 2.95 (dd, 1H), 3.10 (td, 1H), 3.82 (d, 1H), 4.40 (dd, 1H), 4.50 (dd; 1H), 4.58 (d, 1H), 4.80 (d, 1H), 5.00 (s, 1H), 5.93 (s, 1H), 6.20 (s, 1H), 6.30 (s, 1H), 7.10-7.40 (m, 1H), 7.55 (m, 1H), 7.70 (t, 1H), 8.08 (t, 1H), 8.17 (d, 1H), 8.30 (d, 1H), 8.63 (d, 1H), 8.85 (d, 1H).

LC/MS: ESI+: 595 (M+1); HPLC purity: 97.4%

Example 31

4-Diphenylacetyl-1-(quinoline-8-sulfonyl)-piperazine-2-carboxylic acid (thiophen-2-ylmethyl)-amide (Scheme 5, compound I)

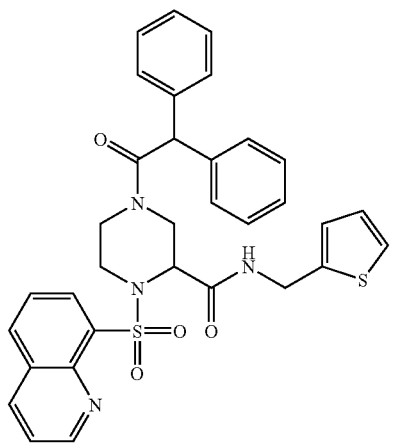 [SMILES: O=C(NCc1cccs1)C1CN(C(=O)C(c2ccccc2)c2ccccc2)CCN1S(=O)(=O)c1cccc2cccnc12]

The title compound was obtained following the general procedure described in example 15 starting from intermediate 2, diphenylacetylchloride and (2-thienylmethyl)amine.

¹H NMR (CDCl₃): 2.83 (td, 1H), 2.96 (dd, 1H), 3.11 (td, 1H), 3.89 (d, 1H), 4.60 (m, 3H), 4.82 (d, 1H), 5.00 (s, 1H), 5.90 (s, 1H), 6.82 (d, 1H), 6.92 (m, 1H), 7.14-7.41 (m, 11H), 7.50 (m, 1H), 7.70 (t, 1H), 8.10 (m, 2H), 8.28 (d, 1), 8.60 (d, 1H), 8.70 (d, 1H).

LC/MS: ESI+: 611 (M+1); HPLC purity: 98.6%

Example 32

4-Diphenylacetyl-1-(quinoline-8-sulfonyl)-piperazine-2-carboxylic acid (pyridin-4-ylmethyl)-amide (Scheme 5, compound I)

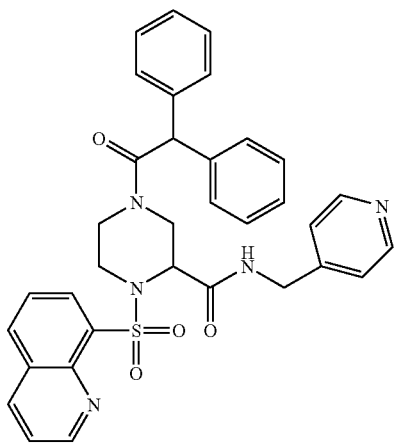 [SMILES: O=C(NCc1ccncc1)C1CN(C(=O)C(c2ccccc2)c2ccccc2)CCN1S(=O)(=O)c1cccc2cccnc12]

The title compound was obtained following the general procedure described in example 15 starting from intermediate 2, diphenylacetylchloride and pyridin-4-ylmethylamine.

¹H NMR (CDCl₃): 2.80 (td, 1H), 2.98 (dd, 1H), 3.20 (td, 1H), 3.91 (d, 1H), 4.40 (dd, 1H), 4.61 (m, 2H), 4.82 (d, 1H), 5.10 (s, 1H), 5.87 (s, 1H), 7.10 (d, 2H), 7.20-7.40 (m, 10H), 7.32 (m, 1H), 7.77 (t, 1H), 8.18 (m, 2H), 8.29 (d, 1H), 8.53 (d, 2H), 8.63 (d, 1H), 8.77 (d, 1H). LC/MS: ESI+: 606 (M+1); HPLC purity: 98.5%

Example 33

4-Diphenylacetyl-1-(thiophene-2-sulfonyl)-piperazine-2-carboxylic acid (3-imidazol-1-yl-propyl)-amide (Scheme 5, compound I)

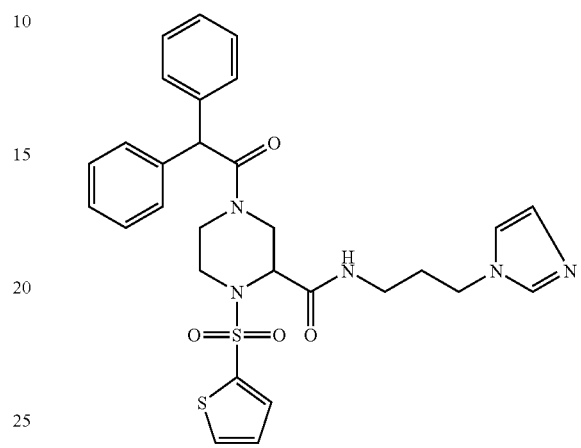

The title compound was obtained following the general procedure described in example 15 starting from intermediate 5, diphenylacetylchloride and 1-(3-aminopropyl)imidazole.

¹NMR (DMSO-d6, 120° C.): 1.91 (qt, 2H), 3.12 (m, 3H), 3.18 (m, 1H), 3.65 (m, 2H), 3.98 (t, 2H), 4.10 (brd, 1H), 4.46 (m, 1H), 4.53 (brd, 1H), 5.40 (s, 1H), 6.93 (s, 1H), 7.09 (s, 1H), 7.19-736 (m, 11H), 7.58 (s, 1H), 7.69 (dd, 1H), 7.78 (m, 1H), 7.94 (m, 1H).

LC/MS: ESI+: 578 (M+1); HPLC purity: 96.4%

Example 34

4-Diphenylacetyl-1-(quinoline-8-sulfonyl)-piperazine-2-carboxylic acid (pyridin-2-ylmethyl)-amide (Scheme 5, compound I)

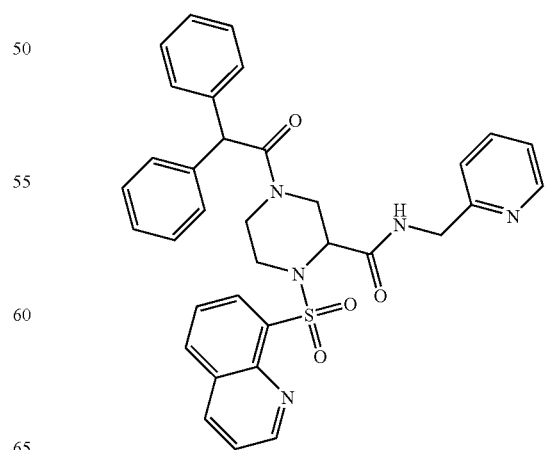

The title compound was obtained following the general procedure described in example 15 starting from intermediate 2, diphenylacetylchloride and pyridin-2-ylmethylamine.

$^1$H MNR (DMSO-d6): 2.50-2.75 (m, 2H), 3.20-3.47 (m, 1.5H), 3.70 (m, 1H), 3.98-4.20 (m, 3H), 4.70 (d, 0.5H), 4.90 (d, 1H), 5.20 (d, 1H), 6.70 (d, 1H), 6.88-7.31 (m, 11H), 7.55 (m, 3H), 8.08-8.49 (m, 4H), 8.55 (m, 1H), 8.82 (d, 1H).

LC/MS: ESI+: 606 (M+1); HPLC purity: 97.10%

Example 35

(R)—N~1~-biphenyl-2-yl-N~3~-[3-(1H-imidazol-1-yl)propyl]-4-(quinolin-8-ylsulfonyl)piperazine-1,3-dicarboxamide trifluoroacetate (Schemes 3 and 4, compound I)

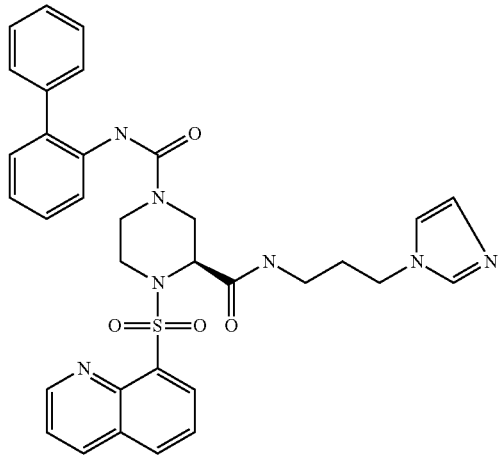

Chiral

The title compound was obtained allowing the general procedure described in example 2 from intermediate 3, 2-biphenylisocyanate and (3-aminopropyl)imidazole.

The final compound was purified by preparative HPLC using Acetonitrile/water; 0.1% TFA as mobile phase affording the TFA salt:

$^1$H MNR (DMSO-d6): 1.72 (m, 1H), 1.20 (m, 1H), 2.60 (m, 1H), 2.86 (m, 2H), 3.12 (m, 1H), 3.72 (m, 3H), 4.07 (t, J=7.3 Hz, 1H), 4.43 (d, J=13.6 Hz, 1H), 4.86 (d, J=2.6 Hz, 1H), 7.23 (m, 9H), 7.50 (d, J=13.9 Hz, 1H), 8.23 (t, J=5.8 Hz, 1H), 7.93 (s, 1H), 8.23 (t, J=5.8 Hz, 1H), 8.31 (dd, J=7.7 and 0.6 Hz, 1H), 8.36 (dd, J=6.6 and 0.6 Hz, 1H), 8.56 (dd, J=8.5 and 1.7 Hz, 1H), 8.83 (s, 1H), 8.96 (dd, J=4.1 and 1.9 Hz, 1H).

LC/MS: ESI+: 626 (M+1); ESI−: 624 (M−1); HPLC purity: 90.0%

Example 36

(S)—N~1~-biphenyl-2-yl-N~3~-[3-(1H-imidazol-1-yl)propyl]-4-(quinolin-8-ylsulfonyl)piperazine-1,3-dicarboxamide trifluoroacetate (Schemes 3 and 2, compound I)

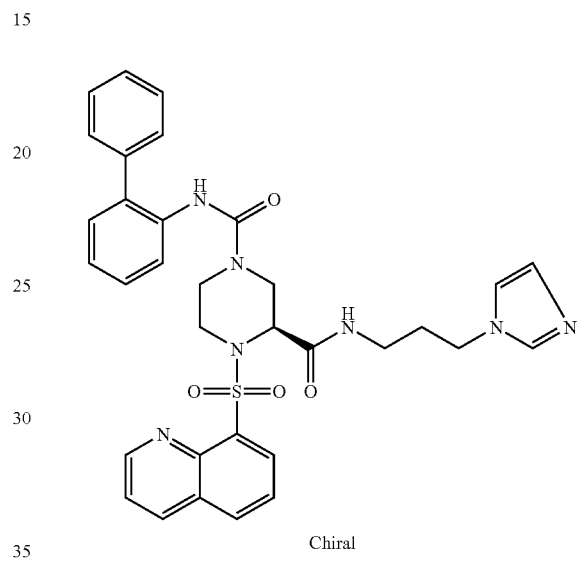

Chiral

The title compound was obtained following the general procedure described for example 35 from (2S)-4-(tert-butoxycarbonyl)-1-(quinolin-8-ylsulfonyl)piperazine-2-carboxylic hydrochloride obtained following the procedure described for intermediate 3 but starting from pure (S)-piperazine-2-carboxylic acid.2CSA, 2-biphenylisocyanate and (3-amino-propyl)imidazole.

$^1$H MNR (DMSO-d6): same as for example 35

LC/MS: ESI+: 626 (M+1); ESI−: 624 (M−1); HPLC purity: 97.0%

| Example | Name | LC/MS (ES+) |
|---|---|---|
| 37 | 1-benzoyl-4-[(4-tert-butylphenyl)sulfonyl]-N-(2-furylmethyl)piperazine-2-carboxamide | 510.8 |
| 38 | 1-benzoyl-4-(biphenyl-4-ylsulfonyl)-N-(2-furylmethyl)piperazine-2-carboxamide | 530.8 |
| 39 | 1-benzoyl-N-benzyl-4-[(4-tert-butylphenyl)sulfonyl]piperazine-2-carboxamide | 520.9 |
| 40 | N-(2,3-dihydro-1H-inden-1-yl)-4-(diphenylacetyl)-1-(phenylsulfonyl)piperazine-2-carboxamide | 580.9 |
| 41 | N-(2-hydroxy-2-phenylethyl)-4-(phenoxyacetyl)-1-(phenylsulfonyl)piperazine-2-carboxamide | 524.8 |
| 42 | 1-benzoyl-N-(diphenylmethyl)-4-(quinolin-8-ylsulfonyl)piperazine-2-carboxamide | 591.9 |
| 43 | 1-benzoyl-4-(diphenylacetyl)-N-(diphenylmethyl)piperazine-2-carboxamide | 594.9 |
| 44 | 1-benzoyl-N-(diphenylmethyl)-4-[(4-methoxyphenyl)acetyl]piperazine-2-carboxamide | 548.9 |
| 45 | 1-benzoyl-N-(4-fluorobenzyl)-4-(4-phenoxybenzoyl)piperazine-2-carboxamide | 538.8 |

-continued

| Example | Name | LC/MS (ES+) |
|---|---|---|
| 46 | 1-benzoyl-4-(diphenylacetyl)-N-(4-fluorobenzyl)piperazine-2-carboxamide | 536.8 |
| 47 | 1-benzoyl-4-(diphenylacetyl)-N-(1-naphthylmethyl)piperazine-2-carboxamide | 568.9 |
| 48 | 1-benzoyl-4-[(4-methoxyphenyl)acetyl]-N-(1-naphthylmethyl)piperazine-2-carboxamide | 522.8 |
| 49 | 1-benzoyl-4-(cyclohexylcarbonyl)-N-(1-naphthylmethyl)piperazine-2-carboxamide | 484.8 |
| 50 | 1-benzoyl-N-(2,3-dihydro-1H-inden-1-yl)-4-(diphenylacetyl)piperazine-2-carboxamide | 544.9 |
| 51 | 1-benzoyl-4-(diphenylacetyl)-N-(2-phenylpropyl)piperazine-2-carboxamide | 546.9 |
| 52 | 1-benzoyl-4-(diphenylacetyl)-N-(4-methoxyphenyl)piperazine-2-carboxamide | 534.8 |
| 53 | 4-acetyl-N-(1,3-benzodioxol-5-ylmethyl)-1-(phenylsulfonyl)piperazine-2-carboxamide | 446.7 |
| 54 | 4-(diphenylacetyl)-N-(2-furylmethyl)-1-(phenylsulfonyl)piperazine-2-carboxamide | 544.8 |
| 55 | 4-acetyl-N-benzyl-1-(phenylsulfonyl)piperazine-2-carboxamide | 402.7 |
| 56 | 4-benzoyl-N-benzyl-1-(phenylsulfonyl)piperazine-2-carboxamide | 464.8 |
| 57 | N-benzyl-4-(diphenylacetyl)-1-(phenylsulfonyl)piperazine-2-carboxamide | 554.9 |
| 58 | 4-acetyl-1-(phenylsulfonyl)-N-(2-thienylmethyl)piperazine-2-carboxamide | 408.7 |
| 59 | 4-(diphenylacetyl)-1-(phenylsulfonyl)-N-(2-thienylmethyl)piperazine-2-carboxamide | 560.9 |
| 60 | N~1~-(2-cyanophenyl)-N~3~-(1-napthylmethyl)-4-(phenylsulfonyl)piperazine-1,3-dicarboxamide | 554.8 |
| 61 | N~1~-biphenyl-2-yl-N~3~-(2,3-dihydro-1H-inden-1-yl)-4-(phenylsulfonyl)piperazine-1,3-dicarboxamide | 581.9 |
| 62 | N-(2,3-dihydro-1H-inden-1-yl)-4-[(4-methoxyphenyl)sulfonyl]-1-(2-thienylsulfonyl)piperazine-2-carboxamide | 562.9 |
| 63 | (1-{[4-(diphenylacetyl)-1-(2-thienylsulfonyl)piperazine-2-yl]carbonyl}piperidin-2-yl)methanol | 568.9 |
| 64 | 4-(diphenylacetyl)-N-[4-(hydroxymethyl)phenyl]-1-(2-thienylsulfonyl)piperazine-2-carboxamide | 576.9 |
| 65 | 4-(diphenylacetyl)-N-(4-fluorobenzyl)-1-(2-thienylsulfonyl)piperazine-2-carboxamide | 578.9 |
| 66 | 1-benzoyl-4-[(3,4-dimethoxyphenyl)sulfonyl]-N-(2-phenylpropyl)piperazine-2-carboxamide | 552.9 |
| 67 | 1-benzoyl-4-[(4-nitrophenyl)sulfonyl]-N-(2-phenylpropyl)piperazine-2-carboxamide | 537.8 |
| 68 | N~1~,4-dibenzoyl-N~3~-(diphenylmethyl)piperazine-1,3-dicarboxamide | 547.8 |
| 69 | 4-benzoyl-N~3~-(2,2-diphenylethyl)-N~1~-(3-methoxyphenyl)piperazine-1,3-dicarboxamide | 563.9 |
| 70 | N~1~-benzoyl-N~3~-(diphenylmethyl)-4-(phenylsulfonyl)piperazine-1,3-dicarboxamide | 583.9 |
| 71 | N~1~-(3,4-dichlorophenyl)-N~3~-(2-hydroxy-2-phenylethyl)-N~3~-methyl-4-(phenylsulfonyl)piperazine-1,3-dicarboxamide | 592.7 |
| 72 | N~3~-(2-hydroxy-2-phenylethyl)-N~3~-methyl-N~1~-(4-phenoxyphenyl)-4-(phenylsulfonyl)piperazine-1,3-dicarboxamide | 615.9 |
| 73 | N~3~-[1,1-bis(hydroxymethyl)propyl]-N~1~-(2-cyanophenyl)-4-(2-thienylsulfonyl)piperazine-1,3-dicarboxamide | 522.8 |
| 74 | N~1~-[4-(benzyloxy)phenyl]-N~3~-(2-hydroxy-2-phenylethyl)-N~3~-methyl-4-(2-thienylsulfonyl)piperazine-1,3-dicarboxamide | 636 |
| 75 | N~3~-(2-hydroxy-2-phenylethyl)-N~3~-methyl-N~1~-(4-phenoxyphenyl)-4-(2-thienylsulfonyl)piperazine-1,3-dicarboxamide | 622 |
| 76 | N-butyl-4-(diphenylacetyl)-1-(2-thienylsulfonyl)piperazine-2-carboxamide | 526.9 |
| 77 | 4-(diphenylacetyl)-N-(2-furylmethyl)-1-(2-thienylsulfonyl)piperazine-2-carboxamide | 550.9 |
| 78 | N-benzyl-4-(diphenylacetyl)-1-(2-thienylsulfonyl)piperazine-2-carboxamide | 560.9 |
| 79 | 4-(diphenylacetyl)-N-(2-thienylmethyl)-1-(2-thienylsulfonyl)piperazine-2-carboxamide | 566.9 |
| 80 | N-(2,3-dihydro-1H-inden-1-yl)-4-(diphenylacetyl)-1-(2-thienylsulfonyl)piperazine-2-carboxamide | 586.9 |
| 81 | 4-(diphenylacetyl)-N-(2-phenylpropyl)-1-(2-thienylsulfonyl)piperazine-2-carboxamide | 589 |

-continued

| Example | Name | LC/MS (ES+) |
|---|---|---|
| 82 | N~1~-biphenyl-2-yl-N~3~-(3-ethoxypropyl)-4-(phenylsulfonyl)piperazine-1,3-dicarboxamide | 551.9 |
| 83 | N~3~-(2-furylmethyl)-N~1~-pentyl-4-(phenylsulfonyl)piperazine-1,3-dicarboxamide | 463.8 |
| 84 | 4-(biphenyl-4-ylsulfonyl)-N~3~-[(1-ethylpyrrolidin-2-yl)methyl]-N~1~-(3-methoxyphenyl)piperazine-1,3-dicarboxamide | 607 |
| 85 | N~1~-[4-(benzyloxy)phenyl]-4-(biphenyl-4-ylsulfonyl)-N~3~-[(1-ethylpyrrolidin-2-yl)methyl]piperazine-1,3-dicarboxamide | 683.1 |
| 86 | N~1~-biphenyl-2-yl-4-(biphenyl-4-ylsulfonyl)-N~3~-[2-(diethylamino)ethyl]piperazine-1,3-dicarboxamide | 641 |
| 87 | N~1~-biphenyl-2-yl-N~3~-(2,3-dihydro-1H-inden-1-yl)-4-(quinolin-8-ylsulfonyl)piperazine-1,3-dicarboxamide | 633 |
| 88 | N~1~-biphenyl-2-yl-N~3~-(2-phenylpropyl)-4-(quinolin-8-ylsulfonyl)piperazine-1,3-dicarboxamide | 635 |
| 89 | N~3~-(4-methoxyphenyl)-N~1~-phenyl-4-(quinolin-8-ylsulfonyl)piperazine-1,3-dicarboxamide | 546.8 |
| 90 | N~3~-(2-hydroxy-2-phenylethyl)-N~3~-methyl-N~1~-(4-phenoxyphenyl)-4-(quinolin-8-ylsulfonyl)piperazine-1,3-dicarboxamide | 667 |
| 91 | 4-benzoyl-N-(diphenylmethyl)-1-(quinolin-8-ylsulfonyl)piperazine-2-carboxamide | 591.9 |
| 92 | N-(diphenylmethyl)-4-(pyridin-2-ylcarbonyl)-1-(quinolin-8-ylsulfonyl)piperazine-2-carboxamide | 592.9 |
| 93 | N-(diphenylmethyl)-4-(3-piperidin-1-ylpropanoyl)-1-(quinolin-8-ylsulfonyl)piperazine-2-carboxamide | 627 |
| 94 | N-(diphenylmethyl)-4-(phenoxyacetyl)-1-(quinolin-8-ylsulfonyl)piperazine-2-carboxamide | 621.9 |
| 95 | N-(diphenylmethyl)-4-[(4-methoxyphenyl)acetyl]-1-(quinolin-8-ylsulfonyl)piperazine-2-carboxamide | 636 |
| 96 | 4-[4-(dimethylamino)benzoyl]-N-(diphenylmethyl)-1-(quinolin-8-ylsulfonyl)piperazine-2-carboxamide | 635 |
| 97 | 4-(cyclohexylcarbonyl)-N-(diphenylmethyl)-1-(quinolin-8-ylsulfonyl)piperazine-2-carboxamide | 598 |
| 98 | 4-acetyl-N-(2,4-dichlorobenzyl)-1-(quinolin-8-ylsulfonyl)piperazine-2-carboxamide | 522.6 |
| 99 | 4-benzoyl-N-(2,4-dichlorobenzyl)-1-(quinolin-8-ylsulfonyl)piperazine-2-carboxamide | 584.7 |
| 100 | N-(2,4-dichlorobenzyl)-4-(pyridin-2-ylcarbonyl)-1-(quinolin-8-ylsulfonyl)piperazine-2-carboxamide | 585.7 |
| 101 | N-(2,4-dichlorobenzyl)-4-(3-piperidin-1-ylpropanoyl)-1-(quinolin-8-ylsulfonyl)piperazine-2-carboxamide | 619.8 |
| 102 | N-(2,4-dichlorobenzyl)-4-(phenoxyacetyl)-1-(quinolin-8-ylsulfonyl)piperazine-2-carboxamide | 614.7 |
| 103 | N-(2,4-dichlorobenzyl)-4-[(2-oxo-6-pentyl-2H-pyran-3-yl)carbonyl]-1-(quinolin-8-ylsulfonyl)piperazine-2-carboxamide | 672.8 |
| 104 | N-(2,4-dichlorobenzyl)-4-(diphenylacetyl)-1-(quinolin-8-ylsulfonyl)piperazine-2-carboxamide | 674.8 |
| 105 | N-(2,4-dichlorobenzyl)-4-[(4-methoxyphenyl)acetyl]-1-(quinolin-8-ylsulfonyl)piperazine-2-carboxamide | 628.7 |
| 106 | N-(2,4-dichlorobenzyl)-4-[4-(dimethylamino)benzoyl]-1-(quinolin-8-ylsulfonyl)piperazine-2-carboxamide | 627.8 |
| 107 | 4-benzoyl-N-(2,2-diphenylethyl)-1-(quinolin-8-ylsulfonyl)piperazine-2-carboxamide | 605.9 |
| 108 | N-(2,2-diphenylethyl)-4-(pyridin-2-ylcarbonyl)-1-(quinolin-8-ylsulfonyl)piperazine-2-carboxamide | 606.9 |
| 109 | N-(2,2-diphenylethyl)-4-(3-piperidin-1-ylpropanoyl)-1-(quinolin-8-ylsulfonyl)piperazine-2-carboxamide | 641 |
| 110 | N-(2,2-diphenylethyl)-4-[(4-methoxyphenyl)acetyl]-1-(quinolin-8-ylsulfonyl)piperazine-2-carboxamide | 650 |
| 111 | 4-[4-(dimethylamino)benzoyl]-N-(2,2-diphenylethyl)-1-(quinolin-8-ylsulfonyl)piperazine-2-carboxamide | 649 |
| 112 | 4-(diphenylacetyl)-N-[(1-ethylpyrrolidin-2-yl)methyl]-1-(quinolin-8-ylsulfonyl)piperazine-2-carboxamide | 627 |
| 113 | N-allyl-4-(diphenylacetyl)-1-(quinolin-8-ylsulfonyl)piperazine-2-carboxamide | 555.9 |
| 114 | N-(1,3-benzodioxol-5-ylmethyl)-4-[(2E)-3-phenylprop-2-enoyl]-1-(quinolin-8-ylsulfonyl)piperazine-2-carboxamide | 585.9 |
| 115 | N-(1,3-benzodioxol-5-ylmethyl)-4-(diphenylacetyl)-1-(quinolin-8-ylsulfonyl)piperazine-2-carboxamide | 649.9 |
| 116 | N-(1,3-benzodioxol-5-ylmethyl)-4-[4-(dimethylamino)benzoyl]-1-(quinolin-8-ylsulfonyl)piperazine-2-carboxamide | 602.9 |
| 117 | 4-(diphenylacetyl)-N-(3-ethoxypropyl)-1-(quinolin-8-ylsulfonyl)piperazine-2-carboxamide | 601.9 |

-continued

| Example | Name | LC/MS (ES+) |
|---|---|---|
| 118 | N-(2-furylmethyl)-4-[(2-oxo-6-pentyl-2H-pyran-3-yl)carbonyl]-1-(quinolin-8-ylsulfonyl)piperazine-2-carboxamide | 593.9 |
| 119 | N-benzyl-4-(phenoxyacetyl)-1-(quinolin-8-ylsulfonyl)piperazine-2-carboxamide | 545.8 |
| 120 | N-benzyl-4-[(2-oxo-6-pentyl-2H-pyran-3-yl)carbonyl]-1-(quinolin-8-ylsulfonyl)piperazine-2-carboxamide | 603.9 |
| 121 | N-benzyl-4-[4-(dimethylamino)benzoyl]-1-(quinolin-8-ylsulfonyl)piperazine-2-carboxamide | 558.9 |
| 122 | 3-{[3-{[2-(hydroxymethyl)piperidin-1-yl]carbonyl}-4-(quinolin-8-ylsulfonyl)piperazin-1-yl]carbonyl}-6-pentyl-2H-pyran-2-one | 611.9 |
| 123 | 4-(diphenylacetyl)-N-[4-(hydroxymethyl)phenyl]-1-(quinolin-8-ylsulfonyl)piperazine-2-carboxamide | 621.9 |
| 124 | 4-(diphenylacetyl)-N-(4-fluorobenzyl)-1-(quinolin-8-ylsulfonyl)piperazine-2-carboxamide | 623.9 |
| 125 | 4-(diphenylacetyl)-N-(2-phenylpropyl)-1-(quinolin-8-ylsulfonyl)piperazine-2-carboxamide | 634 |
| 126 | 4-[(4-methoxyphenyl)acetyl]-N-(2-phenylpropyl)-1-(quinolin-8-ylsulfonyl)piperazine-2-carboxamide | 587.9 |
| 127 | N~1~-biphenyl-2-yl-N~3~-(4-fluorobenzyl)-4-(quinolin-8-ylsulfonyl)piperazine-1,3-dicarboxamide | 624.9 |
| 128 | 1-(3-chlorobenzoyl)-N-(diphenylmethyl)-4-(quinolin-8-ylsulfonyl)piperazine-2-carboxamide | 626.3 |
| 129 | 1-(3-chlorobenzoyl)-N-(2-phenylpropyl)-4-(quinolin-8-ylsulfonyl)piperazine-2-carboxamide | 578.3 |
| 130 | 4-(3-chlorobenzoyl)-N~1~-(3,4-dichlorophenyl)-N~3~-(2,3-dihydro-1H-inden-1-yl)piperazine-1,3-dicarboxamide | 573.1 |
| 131 | 4-(3-chlorobenzoyl)-N~3~-(2,3-dihydro-1H-inden-1-yl)-N~1~-(3-methoxyphenyl)piperazine-1,3-dicarboxamide | 534.2 |
| 132 | 4-(3-chlorobenzoyl)-N~1~-(3,4-dichlorophenyl)-N~3~-(2-phenylpropyl)piperazine-1,3-dicarboxamide | 575.1 |
| 133 | 4-(3-chlorobenzoyl)-N~1~-(2-cyanophenyl)-N~3~-(2-phenylpropyl)piperazine-1,3-dicarboxamide | 531.2 |
| 134 | 4-benzoyl-1-(3-chlorobenzoyl)-N-(diphenylmethyl)piperazine-2-carboxamide | 539.2 |
| 135 | 1-(3-chlorobenzoyl)-N-(diphenylmethyl)-4-(3-piperidin-1-ylpropanoyl)piperazine-2-carboxamide | 574.3 |
| 136 | 1-(3-chlorobenzoyl)-N-(diphenylmethyl)-4-(phenoxyacetyl)piperazine-2-carboxamide | 569.3 |
| 137 | 1-(3-chlorobenzoyl)-N-(diphenylmethyl)-4-[(4-methoxyphenyl)acetyl]piperazine-2-carboxamide | 583.3 |
| 138 | 1-(3-chlorobenzoyl)-4-(cycolohexylcarbonyl)-N-(diphenylmethyl)piperazine-2-carboxamide | 545.3 |
| 139 | 1-(3-chlorobenzoyl)-4-(diphenylacetyl)-N-(2,2-diphenylethyl)piperazine-2-carboxamide | 643.4 |
| 140 | N-(2,4-dichlorobenzyl)-4-[(3,4-dimethoxyphenyl)sulfonyl]-1-(2-thienylsulfonyl)piperazine-2-carboxamide | 635.8 |
| 141 | 1-(biphenyl-4-ylsulfonyl)-4-[(4-tert-butylphenyl)sulfonyl]-N-[(1-ethylpyrrolidin-2-yl)methyl]piperazine-2-carboxamide | 654.1 |
| 142 | 1-(biphenyl-4-ylsulfonyl)-4-[(5-{[(4-chlorobenzoyl)amino]methyl}-2-thienyl)sulfonyl]-N-[(1-ethylpyrrolidin-2-yl)methyl]piperazine-2-carboxamide | 771.6 |
| 143 | N-biphenyl-2-yl-4-(biphenyl-4-ylsulfonyl)-3-{[2-(hydroxymethyl)piperidin-1-yl]carbonyl}piperazine-1-carboxamide | 640 |
| 144 | N~1~-[4-(benzyloxy)phenyl]-4-(biphenyl-4-ylsulfonyl)-N~3~-(2-morpholin-4-ylethyl)piperazine-1,3-dicarboxamide | 685 |
| 145 | 4-(biphenyl-4-ylsulfonyl)-N~3~-(2-morpholin-4-ylethyl)-N~1~-(4-phenoxyphenyl)piperazine-1,3-dicarboxamide | 671 |
| 146 | N~1~-[4-(benzyloxy)phenyl]-4-(biphenyl-4-ylsulfonyl)-N~3~-[3-(1H-imidazol-1-yl)propyl]piperazine-1,3-dicarboxamide | 680 |
| 147 | 4-(biphenyl-4-ylsulfonyl)-N~3~-[3-(1H-imidazol-1-yl)propyl]-N~1~-(4-phenoxyphenyl)piperazine-1,3-dicarboxamide | 666 |
| 148 | 1-(biphenyl-4-ylsulfonyl)-N-[(1-ethylpyrrolidin-2-yl)methyl]-4-(4-phenoxybenzoyl)piperazine-2-carboxamide | 654 |
| 149 | N-allyl-4-[(4-tert-butylphenyl)sulfonyl]-1-(quinolin-8-ylsulfonyl)piperazine-2-carboxamide | 557.9 |
| 150 | N-allyl-4-(biphenyl-4-ylsulfonyl)-1-(quinolin-8-ylsulfonyl)piperazine-2-carboxamide | 577.9 |
| 160 | 4-[(4-tert-butylphenyl)sulfonyl]-N-(2-hydroxyethyl)-1-(quinolin-8-ylsulfonyl)piperazine-2-carboxamide | 561.9 |
| 161 | 4-[(4-tert-butylphenyl)sulfonyl]-N-(2-furylmethyl)-1-(quinolin-8-ylsulfonyl)piperazine-2-carboxamide | 597.9 |
| 162 | 4-[(4-tert-butylphenyl)sulfonyl]-N-(pyridin-4-ylmethyl)-1-(quinolin-8-ylsulfonyl)piperazine-2-carboxamide | 609 |
| 163 | N-(2-phenylpropyl)-4-(phenylsulfonyl)-1-(quinolin-8-ylsulfonyl)piperazine-2-carboxamide | 579.9 |

| Example | Name | LC/MS (ES+) |
|---|---|---|
| 164 | N-(2-phenylpropyl)-1,4-bis(quinolin-8-ylsulfonyl)piperazine-2-carboxamide | 631 |
| 165 | 4-[(4-methoxyphenyl)sulfonyl]-N-(2-phenylpropyl)-1-(quinolin-8-ylsulfonyl)piperazine-2-carboxamide | 609.9 |
| 166 | 4-[(3,4-dimethoxyphenyl)sulfonyl]-N-(2-phenylpropyl)-1-(quinolin-8-ylsulfonyl)piperazine-2-carboxamide | 640 |
| 167 | 4-[(4-methylphenyl)sulfonyl]-N-(2-phenylpropyl)-1-(quinolin-8-ylsulfonyl)piperazine-2-carboxamide | 593.9 |
| 170 | 4-[(4-nitrophenyl)sulfonyl]-N-(2-phenylpropyl)-1-(quinolin-8-ylsulfonyl)piperazine-2-carboxamide | 624.9 |
| 171 | 4-(biphenyl-4-ylsulfonyl)-N-(2-hydroxy-2-phenylethyl)-1-(quinolin-8-ylsulfonyl)piperazine-2-carboxamide | 658 |
| 172 | 4-[(4-tert-butylphenyl)sulfonyl]-N-cyclopropyl-1-(quinolin-8-ylsulfonyl)piperazine-2-carboxamide | 557.9 |
| 173 | N~1~-(2-cyanophenyl)-N~3~-(diphenylmethyl)-4-(quinolin-8-ylsulfonyl)piperazine-1,3-dicarboxamide | 631.9 |
| 174 | N~1~-biphenyl-2-yl-N~3~-(2-furylmethyl)-4-(quinolin-8-ylsulfonyl)piperazine-1,3-dicarboxamide | 596.9 |
| 175 | N~3~-benzyl-N~1~-biphenyl-2-yl-4-(quinolin-8-ylsulfonyl)piperazine-1,3-dicarboxamide | 606.9 |
| 176 | N~1~-biphenyl-2-yl-4-(quinolin-8-ylsulfonyl)-N~3~-(2-thienylmethyl)piperazine-1,3-dicarboxamide | 612.9 |
| 177 | 4-(diphenylacetyl)-N-(pyridin-3-ylmethyl)-1-(quinolin-8-ylsulfonyl)piperazine-2-carboxamide | 606.9 |
| 178 | 4-(biphenyl-4-ylsulfonyl)-N~1~-(3,4-dichlorophenyl)-N~3~-[2-(dimethylamino)ethyl]piperazine-1,3-dicarboxamide | 605.8 |

Example 179

Preparation of a Pharmaceutical Formulation

Formulation 1—Tablets

A piperazine-2-carboxamide compound of formulae (I), (II) or (III) is admixed as a dry powder with a dry gelatin binder in an approximate 1:2 weight ration. A minor amount of magnesium stearate is added as a lubricant. The mixture is formed into 240-270 mg tablets (80-90 mg of active piperazine-2-carboxamide compound per tablet) in a tablet press.

Formulation 2—Capsules

A piperazine-2-carboxamide compound of formulae (I), (II) or (III) is admixed as a dry powder with a starch diluent in an approximate 1:1 weight ratio. The mixture is filled into 250 mg capsules (125 mg of active piperazine-2-carboxamide compound per capsule).

Formulation 3—Liquid

A piperazine-2-carboxamide compound of formulae (I), (II) or (III) sucrose and xanthan gum are blended, passed through a No. 10 mesh U.S. sieve, and then mixed with a previously prepared solution of microcrystalline cellulose and sodium carboxymethyl cellulose (11:89) in water. Sodium benzoate, flavor, and color are diluted with water and added with stirring. Sufficient water is then added.

Formulation 4—Tablets

A piperazine-2-carboxamide compound of formulae (I), (II) or (III) is admixed as a dry powder with a dry gelatin binder in an approximate 1:2 weight ratio. A minor amount of magnesium stearate is added as a lubricant. The mixture is formed into 450-900 mg tablets (150-300 mg of active piperazine-carboxamide compound) in a tablet press.

Formulation 5—Injection

A piperazine-2-carboxamide compound of formulae (I), (II) or (III) is dissolved in a buffered sterile saline injectable aqueous medium to provide a satisfactory concentration.

Example 180

Biological Assays

The compounds of formula (I), were be subjected to the following in vitro and in vivo biological assays:

In vitro competition binding assay with Scintillating Proximity Assay (SPA) (see *Pharmaceutical Manufacturing International*, 1992, p. 49-53 by Cook, N. D. et al)

This assay allows to determine the binding affinity of the test compounds of formula (II) for the human Prostaglandin $F_{2\alpha}$ receptor a) Preparation of Prostaglandin $F_{2\alpha}$ Receptor:

Human Prostaglandin $F_{2\alpha}$ receptor (full-length cDNA) was subcloned into the pCEP4 (Invitrogen) vector and transfected together with the hygromycin resistance gene into HEK 293 EBNA cells by Calcium-phosphate co-precipitation method. Antibiotic resistant cells were grown under constant selection pressure in DMEM/F-12 medium supplemented with 2% fetal calf serum, 4 mM L-Glutamine and 8 ml/l Insulin-Transferrin-Selenium-mix (all Invitrogen) and 300 µg/ml hygromycin at 37° C. in a humidified atmosphere of 5% $CO_2$ in air. At 48 h before harvesting, receptor expression was enhanced by adding 5 mM of Na-butyrate. Cells were washed twice with phosphate buffer saline, harvested and pelleted by centrifugation.

Cell pellet was lysed by Dounce homogenisation in 250 mM sucrose, 25 mM Tris-HCl pH 7.5, 10 mM $MgCl_2$, 1 mM EDTA containing proteases inhibitors according to the manufacturer (Boehringer Mannheim) at 4° C. The lysate was centrifuged at 1000 g, 4° C. for 10 min and the supernatant was centrifuged at 160000 g, 4° C. for 60 min. The membranes pellets were resuspended in binding buffer (10 mM MES pH 6.2, 10 mM $MgCl_2$, 1 mM EDTA containing proteases inhibitors), frozen in dry ice ethanol and stored at −80° C.

b) Determination of the Binding Affinity Values for Test Compounds (PGF2α Receptor):

In vitro competition binding with Scintillation proximity assay (SPA) was performed in Corning NBS 96 wells plates. Briefly, 100 µl of binding buffer containing 15 to 30 µg of purified membranes, 4 mg/ml of wheat-germ agglutinin (WGA) SPA beads and 1 to 2 nM of $^3$H PGF2-alpha (determined by Scatchard analysis) in 1% DMSO was incubated for 2 hours at room temperature. Non-specific binding was determined in the presence of 1 µM of non-radioactive Prostaglandin F$_{2\alpha}$. The concentrations of compounds (antagonist) used to compete with the radioactive ligand (agonist) were 10 µM, 3 µM, 1 µM, 300 nM, 100 nM, 30 nM, 10 nM, 1 nM, 100 pM, 10 pM. The radioactivity was counted on a Microbeta plate counter and the binding data were analysed using the iterative, non-linear, curve-fitting program, "Prism" (GraphPad Software, Inc).

c) Results

The tested compounds according to formula (I) induced an inhibition (illustrated by K$_i$ values) of the binding of Prostaglandin F$_{2\alpha}$ to its receptor of preferably less than 10 µM. The binding affinity of preferred compounds of formula (I) to human and Prostaglandin F$_{2\alpha}$ receptor is illustrated in the below Table 1 by means of the corresponding inhibition constants K$_i$.

Table 1. Binding affinities of test compounds of general formula (I) to human Prostaglandin F$_{2\alpha}$ receptor, as determined in the scintillation proximity competition binding assay (against Prostaglandin F$_{2\alpha}$ as radioligand).

| Structure | IUPAC-Name | Binding affinity for human Prostaglandin F2α receptor Ki (µM) |
|---|---|---|
| 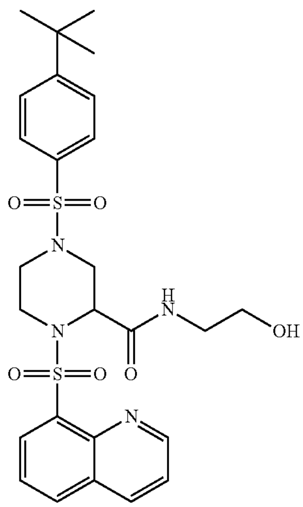 [SMILES: CC(C)(C)c1ccc(S(=O)(=O)N2CCN(S(=O)(=O)c3cccc4cccnc34)C(C(=O)NCCO)C2)cc1] | (2S)-4-[(4-tert-butylphenyl)-sulfonyl]-N-prop-2-enyl-1-(quinolin 8-yl-sulfonyl)piperazine-2-carboxamide | 0.582 |
| 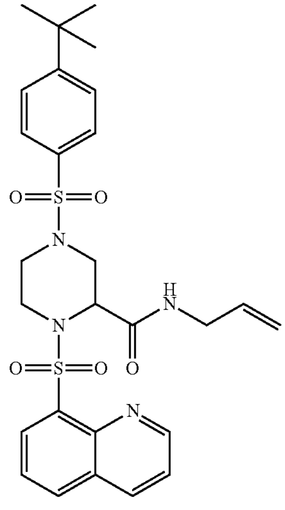 [SMILES: C=CCNC(=O)C1CN(S(=O)(=O)c2ccc(C(C)(C)C)cc2)CCN1S(=O)(=O)c1cccc2cccnc12] | (2S)-4-[(4-tert-butylphenyl)-sulfonyl]-N-prop-2-enyl-1-(quinolin-8-yl-sulfonyl)piperazine-2-carboxamide | 0.125 |

-continued

| Structure | IUPAC-Name | Binding affinity for human Prostaglandin F2α receptor Ki (μM) |
|---|---|---|
| 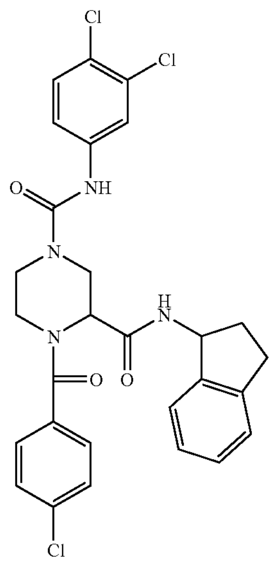 [SMILES: O=C(NC1CCc2ccccc21)C1CN(C(=O)Nc2ccc(Cl)c(Cl)c2)CCN1C(=O)c1ccc(Cl)cc1] | (3S)-4-(3-chlorobenzoyl)-N-1-(3,4-dichlorophenyl)-N-3-[(1S)-2,3-dihydro-1H-inden-1-yl]-piperazine-1,3-dicarboxamide | 0.816 |
| 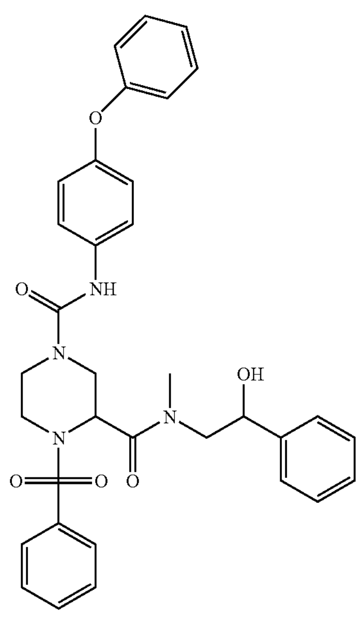 | (3R)-N-3-(2-hydroxy-2-phenyl-ethyl)-N-3-methyl-N-1-(4-phenoxyphenyl)-4-(phenyl-sulfonyl)piperazine-1,3-dicarboxamide | 1.15 |

1) In Vitro Functional Assay 1: Inhibition of Prostaglandin $F_{2\alpha}$ Induced IP3 (Inositol Triphosphate) Synthesis in HEK/EBNA-Cells Expressing the Prostaglandin $F_{2\alpha}$ Receptor The interaction of Prostaglandin $F_{2\alpha}$ with its receptor leads to IP3 synthesis, a second messenger for $Ca^{2+}$ release from sarcoplasmatic reticulum, involved in the process triggering uterine contractions. The present assay described hereinafter can be used to show the inhibition of the Prostaglandin $F_{2\alpha}$/Prostaglandin $F_{2\alpha}$ receptor mediated IP3 synthesis by test compounds of formula (I).

a) Materials:

293-EBNA cells and pCEP4 vector were purchased from Invitrogen; Fetal Bovine Serum from Cansera; Hygromycin B from Roche Molecular Biochemicals; DMEM-F12 medium, L-Glutamine from Life Technologies Inc.; [$^3$H] Inositol from Perkin Elmer Life Sciences; Prostaglandin F$_{2\alpha}$ (PGF$_{2\alpha}$) from Sigma, AG1-X8 chromatography columns from BioRad, 96 well black/white plates from Corning Inc.

b) Constructs:

The cDNAs of the human Prostaglandin F$_{2\alpha}$ receptor (hFP) and of the rat Prostaglandin F$_{2\alpha}$ receptor (rFP) receptors were subcloned into the expression vector pCEP4 to generate pCEP4hFPuno and pCEP4rFP respectively.

c) Cell Culture and Transfection:

293-EBNA cells were grown in DMEM-F12 medium supplemented with 2% fetal bovine serum and 4 mM L-glutamine. Cells were transfected by the calcium phosphate precipitation method with the appropriate plasmid and selected for hygromycinB resistance. The surviving colonies were assayed for their ability to retain specific [$^3$H] PGF$_{2\alpha}$ binding. Selected clones were maintained in DMEM-F12 medium supplemented with 4 mM L-glutamine, 300 µg/ml hygromycinB and 2% fetal bovine serum (10% for cells expressing rFP).

d) Inositol Phosphate Measurements:

Cells were detached with PBS/EDTA, washed with inositol-free DMEM-F12 medium and seeded at 80000 cells/well in a Poly-L-Lysine precoated 12 well plate. Cells were labelled with myo-[$^3$H] Inositol at 4 µCi/ml in inositol-free DMEM-F12 supplemented with 1% fetal bovine serum, 4 mM L-glutamine and 300 µg/ml hygromycinB. After 24 hours (rFP expressing cells) or 40 hours (hFP expressing cells), the medium was removed and cells were pre-incubated for 10 min in assay buffer (DMEM-F12 without Inositol, 20 mM Hepes, 0.1% BSA) containing 20 mM LiCl at 37° C. For agonist dose response, cells were then stimulated for 1 hour at room temperature with increasing concentration of PGF$_{2\alpha}$, in assay buffer. For IC$_{50}$ determination of the compounds, cells were incubated with increasing concentrations of compounds for 10 min at room temperature prior to addition of 30 nM PGF$_{2\alpha}$ (about 2× the EC$_{50}$) and further incubation for 1 hour. For agonist activity determination of the test compounds themselves, the test compounds were added to the cells at 10 µM and 1 µM for 1 hour at room temperature.

In the course of the three above mentioned experiments, the reaction was stopped by addition of 1 ml of stop solution (2.4% perchloric acid) for 10 min. 800 µl were then transferred to 400 µl of neutralising solution (0.72N KOH, 0.6 M KHCO$_3$), vortexed, and sedimented for at least 2 hours at 4° C. After centrifugation of 15 min. at 2500 g, 1 ml of the supernatant was loaded on a chromatography column, followed by two washes with 10 ml of water. The IP3 to be quantified were eluted with 3 ml elution buffer (1M ammonium formate, 0.1 M formic acid) and radioactivity was counted on a Beckman LS6000TA scintillation counter to measure the amount of phosphorylated [$^3$H] inositol.

e) Results

The activities of the piperazine-2-carboxamide derivatives of formula (I) were assessed using the above-described in vitro biological assay. For instance, the compound ((2S)-4-[(4-tert-butylphenyl)sulfonyl]-N-prop-2-enyl-1-(quinolin-8-yl-sulfonyl)piperazine-2-carboxamide) displays an EC$_{50}$ value of 24 nM when tested on human Prostaglandin F$_{2\alpha}$. The value refers to the capacity of the test compounds to effectively antagonize Prostaglandin F$_{2\alpha}$-induced IP3-synthesis mediated by the Prostaglandin F$_{2\alpha}$ receptor.

2) In Vitro Functional Assay 2: Inhibition of Prostaglandin F$_{2\alpha}$ Induced Ca$^{2+}$-Mobilization in HEK/EBNA-Cell Expressing the Prostaglandin F$_{2\alpha}$ Receptor, as Measured by FLIPR® (Fluorimetric Imaging Plate Reader).

a) Calcium Mobilisation Measurements by FLIPR (Fluorometric Imaging Plate Reader)

HEK EBNA cells were seeded at 60000 cells/well in a Poly-L-Lysine precoated black/white bottom 96 well plate. 24 hours later cells were loaded with 4.5 nM Fluo-4 in DMEM-F12 without fetal calf serum for 1-2 hours at 37° C. For Prostaglandin F$_{2\alpha}$ dose response or agonist activity measurement of compounds—after a wash with FLIPR buffer (10 mM Hepes, 145 mM NaCl, 5 mM KCl, 1 mM MgCl$_2$, 10 mM glucose, pH 7.4)—cells were stimulated with increasing concentration of Prostaglandin F$_{2\alpha}$ or test compounds of formulae (I), (II) and (III).

Calcium mobilisation was then measured on the FLIPR for 4 min. For IC$_{50}$ determination of the molecules, increasing concentrations of test compounds were added to the cells 30 min prior to the washing step. After the wash with FLIPR buffer, increasing concentrations of test compounds were added to the cells in FLIPR buffer and calcium mobilisation was measured for 1 min. Then the cells were stimulated with a concentration of 2 times the EC$_{50}$ of Prostaglandin F$_{2\alpha}$ and calcium mobilisation was measured for 4 min.

b) Results

The activities of the piperazine-2-carboxamide derivatives according to formulae (I), (II) and (III) were assessed using the above-described in vitro biological assay. Representative values for some example compounds are given in Table 3 below. The values refer to the capacity of the example compounds according to formula (I) to effectively antagonize Prostaglandin F$_{2\alpha}$-induced intracellular Ca$^{2+}$-mobilization mediated by the Prostaglandin F$_{2\alpha}$-receptor.

TABLE 3

Inhibition of Ca$^{2+}$-mobilization in HEK EBNA cells expressing the human Prostaglandin F$_{2\alpha}$ receptor, by piperazine-2-carboxamide antagonists of formula (I).

| Structure | IUPAC-Name | Inhibition of human Prostaglandin F2α induced Ca$^{2+}$-mobilization IC$_{50}$ (μM) |
|---|---|---|
| 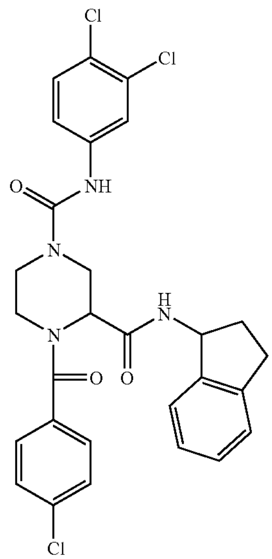 [SMILES: O=C(NC1CCc2ccccc21)C1CN(C(=O)Nc2ccc(Cl)c(Cl)c2)CCN1C(=O)c1ccc(Cl)cc1] | (3S)-4-(3-chlorobenzoyl)-N-1-(3,4-dichlorophenyl)-N-3-[(1S)-2,3-dihydro-1H-inden-1-yl]piperizine-1,3-dicarboxamide | 0.495 |
| 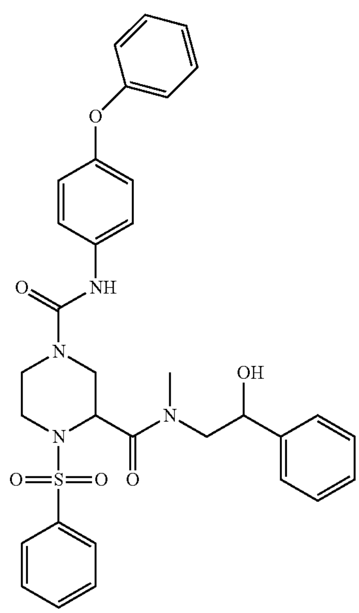 [SMILES: CN(CC(O)c1ccccc1)C(=O)C1CN(C(=O)Nc2ccc(Oc3ccccc3)cc2)CCN1S(=O)(=O)c1ccccc1] | (3R)-N-3-(2-hydroxy-2-phenylethyl)-N-3-methyl-N-1-(4-phenoxyphenyl)-4-(phenylsulfonyl)piperazine-1,3-dicarboxamide | 4.75 |

3) In Vivo Assay: Reduction of Uterine Contractile Activity in Rats

Spontaneous Uterine Contractions in Late-Term Pregnant Rats:

a) Preparation of the Experiment:

Late-term pregnant (19-21 days of gestation) Sprague Dawley female rats (Charles River, Calco, Italy) weighing 350-400 g were anesthetised with urethane (1.05 g/kg, i.p.) and placed on a homeothermic operating table. The trachea was isolated and cannulated with a suitable polyethylene (PE) tubing. A midline incision at the hypogastrium level was made, one pregnant uterine horn exposed and its tubal end closed (near the ovary) by a ligature with surgical silk. In the correspondence of the last foetus near the above-mentioned ovary, the uterine horn wall was incided taking care not to injure the adjacent placenta, and a PE240 tubing with a latex balloon (9 mm length when empty, capacity 0.1 ml; Radnoti, Monrovia, Calif., USA) on the top was inserted into the lumen and secured with surgical silk. After filling the internal cavity of the latex balloon with 0.1 ml of sterile physiological saline solution, the catheter was connected to an amplifying/recording system (MacLab, AD Instruments Pty Ltd, Castle Hill, Australia) via a P23ID Gould Statham pressure transducer. One jugular vein was then isolated and cannulated with a PE60 catheter connected to a butterfly needle for the intravenous administration of the vehicle or test compounds.

After a suitable stabilization period, vehicle or increasing doses of the test compound were administered by a 10-min intravenous infusion. Each dose administration was followed by a 30-min recovery period.

b) Results

The spontaneous contractile response of the uterus was quantified by evaluating the area under the curve (AUC) of the changes in the intra-luminal uterine pressure over time (by Chart V4.04 for Windows software, PowerLab AD Instruments, Castle Hill, Australia). The effect of the test compound on the spontaneous uterine contraction was evaluated as the percent variation of the AUC calculated in a 10-min interval following the administration of each dose of test compound as compared to the AUC in a 10-min interval before the administration of the first dose of test compound (basal value). When possible, a dose-response curve (of peak effect) was plotted and the relative ED50 value calculated (by S-Plus 2000 v. 4.6 statistical software, Mathsoft, Inc. Seattle, Wash., USA).

For instance the test compound [5-(tert-butyl)-2-(8-quinolylsulfonyl)phenyl]-N-prop-2-enylcarboxamide, upon administration by i.v. route (infusion over 10 minutes), caused inhibition of uterine contractions of 56.1% at a dose of 3 mg/kg/min in the experiment outlined above.

REFERENCE LIST

*Journal of Endocrinology* 157, p. 343-359 (1998))
*Science* vol. 277 p. 681-687 (1997)
*Res. Reprod.* 16:1-2 by McCracken (1984)
*Prostaglandins,* 12(6) p. 1053-9 (1976)
*J. Reprod. Fertil.,* 116(1), p. 103-111 (1999)
*Rev. Reprod.,* 5(1), p. 38-45 (2000)
*Biochem. Biophys. Res. Commun.,* 288(5), p. 1155-1161 (2001)
*Tetrahedron Letters,* 30 (39), p. 5193-96 (1989)
*J. Med. Chem,* 43(3), p. 369 (2000)
*Tetrahedron Letters,* 39, p. 1295-98 (1998)
*Biochemica at Biophysica Acta* 1258/2, p. 215-223 (1995
*Cancer Research,* Vol 58, Issue 11 p. 2323-2327
JP01050818
U.S. Pat. No. 6,271,201
WO 02/058546

The invention claimed is:

1. A piperazine-2-carboxamide compound defined by formula (II):

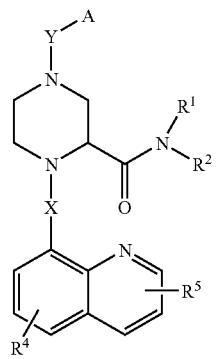

(II)

or its enantiomers, diastereomers, racemate, or its pharmaceutically acceptable salts, wherein A is aryl or heteroaryl; and X is selected from the group consisting of —CO— and —SO$_2$—;

Y is selected from the group consisting of —SO$_2$—, —CO—, and —CO—NR$^3$, wherein R$^3$ is as defined below;

R$^1$ and R$^2$ are each independently from each other selected from the group consisting of hydrogen, hydroxy, sulfonyl, amino, C$_1$-C$_6$-alkyl, C$_2$-C$_6$-alkenyl, C$_2$-C$_6$-alkynyl, aryl, heteroaryl, (C$_3$-C$_8$)-cycloalkyl, and heterocycloalkyl, an acyl moiety, C$_1$-C$_6$-alkyl aryl, C$_1$-C$_6$-alkyl heteroaryl, C$_2$-C$_6$-alkenyl aryl, C$_2$-C$_6$-alkenyl heteroaryl, C$_2$-C$_6$-alkynyl aryl, C$_2$-C$_6$-alkynyl heteroaryl, C$_1$-C$_6$-alkyl cycloalkyl, C$_1$-C$_6$-alkyl hetero-cycloalkyl, C$_2$-C$_6$-alkenyl cycloalkyl, C$_2$-C$_6$-alkenyl heterocycloalkyl, C$_2$-C$_6$-alkynyl cycloalkyl, C$_2$-C$_6$-alkynyl heterocycloalkyl, alkoxycarbonyl, aminocarbonyl, C$_1$-C$_6$-alkyl carboxy, C$_1$-C$_6$-alkyl acyl, aryl acyl, heteroaryl acyl, C$_3$-C$_8$-(hetero)-cycloalkyl acyl, C$_1$-C$_6$-alkyl acyloxy, C$_1$-C$_6$-alkyl alkoxy, C$_1$-C$_6$-alkyl alkoxycarbonyl, C$_1$-C$_6$-alkyl aminocarbonyl, C$_1$-C$_6$-alkyl acylamino, acylamino, C$_1$-C$_6$-alkyl ureido, C$_1$-C$_6$-alkyl carbamate, C$_1$-C$_6$-alkyl amino, C$_1$-C$_6$-alkyl ammonium, C$_1$-C$_6$-alkyl sulfonyloxy, C$_1$-C$_6$-alkyl sulfonyl, C$_1$-C$_6$-alkyl sulfinyl, C$_1$-C$_6$-alkyl sulfanyl, C$_1$-C$_6$-alkyl sulfonylamino and C$_1$-C$_6$-alkyl aminosulfonyl, provided R$^1$ and R$^2$ cannot simultaneously be hydrogen and hydroxyl, wherein R$^1$ and R$^2$ optionally form together a 3-8 membered heterocycle optionally comprising a heteroatom selected from the group consisting of 0, N and S;

R$^3$ is selected from the group consisting of H, and straight or branched C$_1$-C$_6$-alkyl;

R$^4$ and R$^5$ are each independently from each other selected from the group consisting of straight or branched C$_1$-C$_6$-alkyl, C$_2$-C$_6$-alkenyl, C$_2$-C$_6$-alkynyl, aryl, heteroaryl, C$_3$-C$_8$-cycloalkyl or heterocycloalkyl, C$_1$-C$_6$-alkyl aryl, C$_1$-C$_6$-alkyl heteroaryl, C$_1$-C$_6$-alkyl cycloalkyl, C$_1$-C$_6$-alkyl heterocycloalkyl, C$_2$-C$_6$-alkenyl-aryl or -heteroaryl, C$_2$-C$_6$-alkynyl aryl or -heteroaryl, carboxy, cyano, halogen, hydroxy, C$_1$-C$_6$-alkoxy, nitro, acylamino, ureido, sulfonylamino, sulfanyl and sulfonyl.

2. The piperazine-2-carboxamide compound according to claim 1, wherein X is —SO$_2$—.

3. The piperazine-2-carboxamide compound according to claim 1, wherein X and Y are each independently from each other —SO$_2$— or —CO.

4. The piperazine-2-carboxamide compound according to claim 1, wherein X is —SO$_2$—, Y is —SO$_2$—, —CO— or —CO—NR$^3$—, wherein R$^3$ is H or straight or branched (C$_1$-C$_6$)-alkyl, A is aryl or heteroaryl, R$^1$ is H or —CH$_3$, R$^2$ is straight or branched (C$_1$-C$_6$)-alkyl, (C$_2$-C$_6$)-alkenyl, aryl, (C$_1$-C$_6$)-alkyl aryl, heteroaryl, (C$_1$-C$_6$)-alkyl-heteroaryl, cycloalkyl, (C$_1$-C$_6$)-alkyl-cycloalkyl, 3-8-membered heterocycloalkyl, (C$_1$-C$_6$)-alkyl-3-8-membered heterocycloalkyl, R$^1$ and R$^2$ together optionally form a 3-8-membered heterocycle, and R$^4$ and R$^5$ are both H.

5. The piperazine-2-carboxamide compound according to claim 1, wherein X is —SO$_2$—, Y is —CO—, —CONH—, —SO$_2$—, A is tert-butoxy carbonyl, phenoxyphenyl, dimethylamino-phenyl, diphenylmethyl, phenyl prop-2-enyl, 6 pentyl-2-one pyranyl, R$^1$ is H or —CH$_3$, R$^2$ is hydroxyethyl, propen-2-enyl, 3-hydroxy-1-phenyl propyl, 2-hydroxy-1-phenyl ethyl, prop-2-enyl, methoxy phenyl, 2-hydroxy-2-phenyl ethyl, 2,2 diphenylethyl, 1-ethyl pyrrolidin-1-2-yl, 1,3 benzodioxol-5-yl-methyl, 2-furylmethyl, benzyl, pyridin-4-yl-methyl, 2-(hydroxymethyl)piperidin-1-yl, 2-hydroxyethyl, 2-hydroxy-2-phenyl ethyl or cyclopropyl, and $R^2$ together optionally form a piperidine, and $R^4$ and $R^5$ are both hydrogen.

6. The piperazine-2-carboxamide compound according to claim 1 selected from the group consisting of:

- (2S)-4-[(4-tert-butylphenyl)sulfonyl]-N-(2-hydroxyethyl)-1-(quinolin-8-yl-sulfonyl)piperazine-2-carboxamide;
- (2R)-4-[(4-tert-butylphenyl)sulfonyl]-N-(2-hydroxyethyl)-1-(quinolin-8-yl-sulfonyl)piperazine-2-carboxamide;
- (2S)-4-[(4-tert-butylphenyl)sulfonyl]-N-prop-2-enyl-1-(quinolin-8-yl-sulfonyl)piperazine-2-carboxamide;
- (2R)-4-[(4-tert-butylphenyl)sulfonyl]-N-prop-2-enyl-1-(quinolin-8-yl-sulfonyl)piperazine-2-carboxamide;
- (2R)-4-[(4-tert-butylphenyl)sulfonyl]-N-[(1S)-3-hydroxy-1-phenylpropyl]-1-(quinolin-8-yl-sulfonyl)piperazine-2-carboxamide;
- (2R)-4-[(4-tert-butylphenyl)sulfonyl]-N-[(1R)-3-hydroxy-1-phenylpropyl]-1-(quinolin-8-yl-sulfonyl)piperazine-2-carboxamide;
- (2R)-4-[(4-tert-butylphenyl)sulfonyl]-N-[(1R)-2-hydroxy-1-phenylethyl]-1-(quinolin-8-yl-sulfonyl)piperazine-2-carboxamide;
- (2R)-4-[(4-tert-butylphenyl)sulfonyl]-N-[(1S)-2-hydroxy-1-phenylethyl]-1-(quinolin-8-yl-sulfonyl)piperazine-2-carboxamide;
- 4-(diphenylacetyl)-N-(2-furylmethyl)-1-(quinolin-8-yl-sulfonyl)piperazine-2-carboxamide;
- 4-Diphenylacetyl-1-(quinolin-8-sulfonyl)-piperazine-2-carboxylic acid (pyridin-4-ylmethyl)-amide;
- 4-Diphenylacetyl-1-(quinoline-8-sulfonyl)-piperazine-2-carboxylic acid benzylamide;
- 4-Diphenylacetyl-1-(quinoline-8-sulfonyl)-piperazine-2-carboxylic acid (thiophen-2-ylmethyl)-amide;
- 4-Diphenylacetyl-1-(quinoline-8-sulfonyl)-piperazine-2-carboxylic acid (pyridin-2-ylmethyl)-amide;
- (R)—N-1-biphenyl-2-yl-N-3-[3-(1H-imidazol-1-yl)propyl]-4-(quinolin-8-ylsulfonyl)piperazine-1,3-dicarboxamide;
- (S)—N-1-biphenyl-2-yl-N-3-[3-(1H-imidazol-1-yl)propyl]-4-(quinolin-8-ylsulfonyl)piperazine-1,3-dicarboxamide;
- N-1-biphenyl-2-yl-N-3-(2,3-dihydro-1H-inden-1-yl)-4-(quinolin-8-ylsulfonyl)piperazine-1,3-dicarboxamide;
- N-1-biphenyl-2-yl-N-3-(2-phenylpropyl)-4-(quinolin-8-ylsulfonyl)piperazine-1,3-dicarboxamide;
- N-3-(4-methoxyphenyl)-N-1-phenyl-4-(quinolin-8-ylsulfonyl)piperazine-1,3-dicarboxamide;
- N-3-(2-hydroxy-2-phenylethyl)-N-3-methyl-N-1-(4-phenoxyphenyl)-4-(quinolin-8-ylsulfonyl)piperazine-1,3-dicarboxamide;
- 4-benzoyl-N-(diphenylmethyl)-1-(quinolin-8-ylsulfonyl)piperazine-2-carboxamide;
- N-(diphenylmethyl)-4-(pyridin-2-ylcarbonyl)-1-(quinolin-8-ylsulfonyl)piperazine-2-carboxamide;
- N-(diphenylmethyl)-4-(3-piperidin-1-ylpropanoyl)-1-(quinolin-8-ylsulfonyl)piperazine-2-carboxamide;
- N-(diphenylmethyl)-4-(phenoxyacetyl)-1-(quinolin-8-ylsulfonyl)piperazine-2-carboxamide;
- N-(diphenylmethyl)-4-[(4-methoxyphenyl)acetyl]-1-(quinolin-8-ylsulfonyl)piperazine-2-carboxamide;
- 4-[4-(dimethylamino)benzoyl]-N-(diphenylmethyl)-1-(quinolin-8-ylsulfonyl)piperazine-2-carboxamide;
- 4-(cyclohexylcarbonyl)-N-(diphenylmethyl)-1-(quinolin-8-ylsulfonyl)piperazine-2-carboxamide;
- 4-acetyl-N-(2,4-dichlorobenzyl)-1-(quinolin-8-ylsulfonyl)piperazine-2-carboxamide;
- 4-benzoyl-N-(2,4-dichlorobenzyl)-1-(quinolin-8-ylsulfonyl)piperazine-2-carboxamide;
- N-(2,4-dichlorobenzyl)-4-(pyridin-2-ylcarbonyl)-1-(quinolin-8-ylsulfonyl)piperazine-2-carboxamide;
- N-(2,4-dichlorobenzyl)-4-(3-piperidin-1-ylpropanoyl)-1-(quinolin-8-ylsulfonyl)piperazine-2-carboxamide;
- N-(2,4-dichlorobenzyl)-4-(phenoxyacetyl)-1-(quinolin-8-ylsulfonyl)piperazine-2-carboxamide;
- N-(2,4-dichlorobenzyl)-4-[(2-oxo-6-pentyl-2H-pyran-3-yl)carbonyl]-1-(quinolin-8-ylsulfonyl)piperazine-2-carboxamide;
- N-(2,4-dichlorobenzyl)-4-(diphenylacetyl)-1-(quinolin-8-ylsulfonyl)piperazine-2-carboxamide;
- N-(2,4-dichlorobenzyl)-4-[(4-methoxyphenyl)acetyl]-1-(quinolin-8-ylsulfonyl)piperazine-2-carboxamide;
- N-(2,4-dichlorobenzyl)-4-[4-(dimethylamino)benzoyl]-1-(quinolin-8-ylsulfonyl)piperazine-2-carboxamide;
- 4-benzoyl-N-(2,2-diphenylethyl)-1-(quinolin-8-ylsulfonyl)piperazine-2-carboxamide;
- N-(2,2-diphenylethyl)-4-(pyridin-2-ylcarbonyl)-1-(quinolin-8-ylsulfonyl)piperazine-2-carboxamide;
- N-(2,2-diphenylethyl)-4-(3-piperidin-1-ylpropanoyl)-1-(quinolin-8-ylsulfonyl)piperazine-2-carboxamide;
- N-(2,2-diphenylethyl)-4-[(4-methoxyphenyl)acetyl]-1-(quinolin-8-ylsulfonyl)piperazine-2-carboxamide;
- 4-[4-(dimethylamino)benzoyl]-N-(2,2-diphenylethyl)-1-(quinolin-8-ylsulfonyl)piperazine-2-carboxamide;
- 4-(diphenylacetyl)-N-[(1-ethylpyrrolidin-2-yl)methyl]-1-(quinolin-8-ylsulfonyl)piperazine-2-carboxamide;
- N-allyl-4-(diphenylacetyl)-1-(quinolin-8-ylsulfonyl)piperazine-2-carboxamide;
- N-(1,3-benzodioxol-5-ylmethyl)-4-[(2E)-3-phenylprop-2-enoyl]-1-(quinolin-8-ylsulfonyl)piperazine-2-carboxamide;
- N-(1,3-benzodioxol-5-ylmethyl)-4-(diphenylacetyl)-1-(quinolin-8-ylsulfonyl)piperazine-2-carboxamide;
- N-(1,3-benzodioxol-5-ylmethyl)-4-[4-(dimethylamino)benzoyl]-1-(quinolin-8-ylsulfonyl)piperazine-2-carboxamide;
- 4-(diphenylacetyl)-N-(3-ethoxypropyl)-1-(quinolin-8-ylsulfonyl)piperazine-2-carboxamide;
- N-(2-furylmethyl)-4-[(2-oxo-6-pentyl-2H-pyran-3-yl)carbonyl]-1-(quinolin-8-ylsulfonyl)piperazine-2-carboxamide;
- N-benzyl-4-(phenoxyacetyl)-1-(quinolin-8-ylsulfonyl)piperazine-2-carboxamide;
- N-benzyl-4-[(2-oxo-6-pentyl-2H-pyran-3-yl)carbonyl]-1-(quinolin-8-ylsulfonyl)piperazine-2-carboxamide;
- N-benzyl-4-[4-(dimethylamino)benzoyl]-1-(quinolin-8-ylsulfonyl)piperazine-2-carboxamide;
- 3-{[3-{[2-(hydroxymethyl)piperidin-1-yl]carbonyl}-4-(quinolin-8-ylsulfonyl)piperazin-1-yl]carbonyl}-6-pentyl-2H-pyran-2-one;
- 4-(diphenylacetyl)-N-[4-(hydroxymethyl)phenyl]-1-(quinolin-8-ylsulfonyl)piperazine-2-carboxamide;
- 4-(diphenylacetyl)-N-(4-fluorobenzyl)-1-(quinolin-8-ylsulfonyl)piperazine-2-carboxamide;
- 4-(diphenylacetyl)-N-(2-phenylpropyl)-1-(quinolin-8-ylsulfonyl)piperazine-2-carboxamide;
- 4-[(4-methoxyphenyl)acetyl]-N-(2-phenylpropyl)-1-(quinolin-8-ylsulfonyl)piperazine-2-carboxamide;
- N-1-biphenyl-2-yl-N-3-(4-fluorobenzyl)-4-(quinolin-8-ylsulfonyl)piperazine-1,3-dicarboxamide;

1-(3-chlorobenzoyl)-N-(diphenylmethyl)-4-(quinolin-8-ylsulfonyl)piperazine-2-carboxamide;
1-(3-chlorobenzoyl)-N-(2-phenylpropyl)-4-(quinolin-8-ylsulfonyl)piperazine-2-carboxamide;
N-allyl-4-[(4-tert-butylphenyl)sulfonyl]-1-(quinolin-8-ylsulfonyl)piperazine-2-carboxamide;
N-allyl-4-(biphenyl-4-ylsulfonyl)-1-(quinolin-8-ylsulfonyl)piperazine-2-carboxamide;
4-[(4-tert-butylphenyl)sulfonyl]-N-(2-hydroxyethyl)-1-(quinolin-8-ylsulfonyl)piperazine-2-carboxamide;
4-[(4-tert-butylphenyl)sulfonyl]-N-(2-furylmethyl)-1-(quinolin-8-ylsulfonyl)piperazine-2-carboxamide;
4-[(4-tert-butylphenyl)sulfonyl]-N-(pyridin-4-ylmethyl)-1-(quinolin-8-ylsulfonyl)piperazine-2-carboxamide;
N-(2-phenylpropyl)-4-(phenylsulfonyl)-1-(quinolin-8-ylsulfonyl)piperazine-2-carboxamide;
N-(2-phenylpropyl)-1,4-bis(quinolin-8-ylsulfonyl)piperazine-2-carboxamide;
4-[(4-methoxyphenyl)sulfonyl]-N-(2-phenylpropyl)-1-(quinolin-8-ylsulfonyl)piperazine-2-carboxamide;
4-[(3,4-dimethoxyphenyl)sulfonyl]-N-(2-phenylpropyl)-1-(quinolin-8-ylsulfonyl)piperazine-2-carboxamide;
4-[(4-methylphenyl)sulfonyl]-N-(2-phenylpropyl)-1-(quinolin-8-ylsulfonyl)piperazine-2-carboxamide;
4-[(4-nitrophenyl)sulfonyl]-N-(2-phenylpropyl)-1-(quinolin-8-ylsulfonyl)piperazine-2-carboxamide;
4-(biphenyl-4-ylsulfonyl)-N-(2-hydroxy-2-phenylethyl)-1-(quinolin-8-ylsulfonyl)piperazine-2-carboxamide;
4-[(4-tert-butylphenyl)sulfonyl]-N-cyclopropyl-1-(quinolin-8-ylsulfonyl)piperazine-2-carboxamide;
N-1-(2-cyanophenyl)-N-3-(diphenylmethyl)-4-(quinolin-8-ylsulfonyl)piperazine-1,3-dicarboxamide;
N-1-biphenyl-2-yl-N-3-(2-furylmethyl)-4-(quinolin-8-ylsulfonyl)piperazine-1,3-dicarboxamide;
N-3-benzyl-N-1-biphenyl-2-yl-4-(quinolin-8-ylsulfonyl)piperazine-1,3-dicarboxamide;
N-1-biphenyl-2-yl-4-(quinolin-8-ylsulfonyl)-N-3-(2-thienylmethyl)piperazine-1,3-dicarboxamide; and
4-(diphenylacetyl)-N-(pyridin-3-ylmethyl)-1-(quinolin-8-ylsulfonyl)piperazine-2-carboxamide.

7. A medicament comprising the piperazine-2-carboxamide compound according to claim 1.

8. A method of preparing a medicament for the treatment of dysmenorrhea, preterm labor, premature birth and for stopping labor prior to cesarean delivery comprising combining a piperazine-2-carboxamide compound according to claim 1, and a pharmaceutically acceptable carrier, diluent or excipient thereof.

9. A pharmaceutical composition comprising at least one piperazine-2-carboxamide compound according to claim 1 and a pharmaceutically acceptable carrier, diluent or excipient thereof.

10. A method for the treatment of dysmenorrhea, preterm labor, premature birth and for stopping labor prior to cesarean delivery, which comprises:
administering an effective amount of the piperazine-2-carboxamide compound, its racemate forms, or its pharmaceutically acceptable salts according to claim 1, to a mammal in need thereof.

* * * * *

UNITED STATES PATENT AND TRADEMARK OFFICE
CERTIFICATE OF CORRECTION

PATENT NO. : 8,404,690 B2  Page 1 of 1
APPLICATION NO. : 10/545296
DATED : March 26, 2013
INVENTOR(S) : Page et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1914 days.

Signed and Sealed this

First Day of September, 2015

Michelle K. Lee
*Director of the United States Patent and Trademark Office*